United States Patent [19]

Menard et al.

[11] 4,406,834
[45] Sep. 27, 1983

[54] 2,6 DISUBSTITUTED PENEMS AND INTERMEDIATES THEREFOR

[75] Inventors: Marcel Menard, Candiac; Alain Martel, Delson, both of Canada

[73] Assignee: Bristol-Myers Company, New York, N.Y.

[21] Appl. No.: 253,982

[22] Filed: Apr. 13, 1981

Related U.S. Application Data

[60] Division of Ser. No. 77,886, Sep. 21, 1979, Pat. No. 4,282,150, which is a continuation-in-part of Ser. No. 968,663, Dec. 1, 1978, abandoned.

[51] Int. Cl.³ .................. C07D 205/08; C07D 499/04
[52] U.S. Cl. .................................................. 260/239 A
[58] Field of Search .................................... 260/239 A

[56] References Cited

U.S. PATENT DOCUMENTS

| | | | |
|---|---|---|---|
| 4,070,477 | 1/1978 | Ernest | 260/239 A |
| 4,155,912 | 5/1979 | Menard | 260/239 A |
| 4,192,801 | 3/1980 | Ueda | 260/239 A |
| 4,272,437 | 6/1981 | Menard | 260/239 A |

FOREIGN PATENT DOCUMENTS

| | | |
|---|---|---|
| 2210 | 6/1979 | European Pat. Off. |
| 2819655 | 11/1978 | Fed. Rep. of Germany |

OTHER PUBLICATIONS

Woodward et al., Acta Chem. Suecica 14 (supl.) 23 (197).
Clarke, Ed., "Annual Reports in Medranol Chemistry, vol. 13", 1978, pp. 239–248.
Bristol Myers, Chem. Abs. 94, 30747g (1980).

*Primary Examiner*—Mark L. Berch
*Attorney, Agent, or Firm*—David M. Morse

[57] ABSTRACT

This invention relates to 2-substituted and 2,6-disubstituted penem compounds of the formula

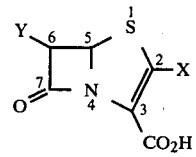

wherein Y is hydrogen, halo or certain organic radicals and X represents certain hetero-interrupted substituted alkyl radicals. Also included in the invention are pharmaceutically acceptable salts of the above compounds and derivatives of the above compounds in which the carboxyl group at the 3-position is protected as by an easily removable ester protecting group. The compounds of the present invention are potent antibacterial agents or are of use as intermediates in the preparation of such agents.

3 Claims, No Drawings

2,6 DISUBSTITUTED PENEMS AND INTERMEDIATES THEREFOR

CROSS-REFERENCE TO RELATED APPLICATION

This application is a division of our co-pending application Ser. No. 77,886 filed Sept. 21, 1979 now 4,282,150 which is a continuation-in-part application of application Ser. No. 968,663 filed Dec. 1, 1978, now abandoned.

BACKGROUND OF THE INVENTION

1. Field of the Invention

Novel 2-substituted and 2,6-disubstituted penem compounds are prepared by totally synthetic chemical processes and found to be potent β-lactam antibiotics.

2. Description of the Prior Art

Penicillins and cephalosporins comprise a group of well-known antibacterial agents commonly grouped together as a class called β-lactam antibiotics. Most of the work in this field has been done, broadly speaking, with 6-aminopenicillanic acid (6-APA), 7-aminocephalosporanic acid (7-ACA) and derivatives thereof produced by fermentation or chemical transformation of the natural products. Despite the extensive progress made in preparing active derivatives of 6-APA and 7-ACA, there is a continuing search for synthetic and semi-synthetic routes to new families of β-lactam antibiotics which may possess more advantageous properties than those derived from the known penicillin and cephalosporin nuclei.

Considerable work has been done on total chemical synthesis of both known β-lactams and nuclear analogs of such known compounds. Literature publications relating to non-conventional bicyclic β-lactams include the following:

(a) Belgian Pat. No. 846,933 discloses the compound of the formula

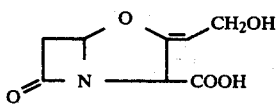

which has been isolated from fermentation of *Streptomyces clavuligerus*. This compound, named clavulanic acid, possesses a low order of antibacterial activity but inhibits the action of certain β-lactamases and reportedly enhances the in vitro and in vivo activity of some penicillins and cephalosporins.

(b) U.K. Pat. No. 1,467,413 discloses the fermentation product having the formula

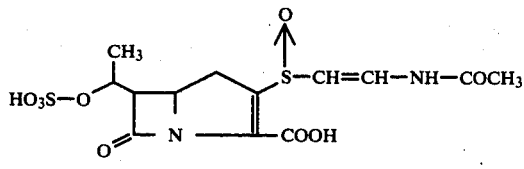

which is reported to possess some antibacterial activity and to be a β-lactamase inhibitor.

(c) Brown, et al. in J.C.S. Chem. Comm., 359–360 (1977) disclose preparation of the compound of the formula

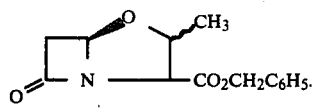

There is no indication from the publication that the compound possesses any antibacterial activity.

(d) Eglington in J.C.S. Chem. Comm., 720 (1977) discloses preparation of the ester of the formula

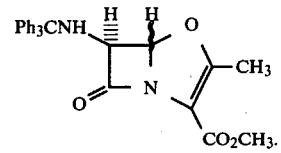

The compound is reported to be a weak inhibitor of β-lactamases.

(e) U.S. Pat. No. 3,950,357 describes a fermentation process for producing thienamycin, the compound of the formula

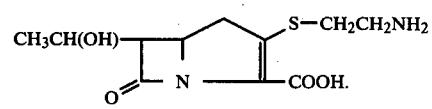

Thienamycin is reported to be a highly potent broad-spectrum antibiotic.

(f) Belgian Pat. No. 849,118 (equivalent U.S. Pat. No. is 4,118,566) discloses a series of 6-amino-2-penem-3-carboxylic acid derivatives of the formula

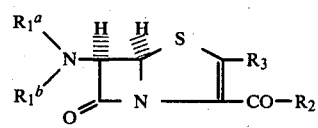

wherein $R_1^a$ is hydrogen or an N-protecting group, $R_1^b$ is hydrogen or acyl (or $R_1^a$ and $R_1^b$ taken together are a divalent N-protecting group), —CO—$R_2$ is carboxyl or a protected carboxyl group and $R_3$ is hydrogen or a C-bonded organic group. The compounds and their salts are said to possess antibacterial activity. No compounds are disclosed which do not contain the amino or acylamido moiety at the 6-position of the β-lactam ring.

(g) Acta Pharmaceutica Suecica, 14 (Suppl.), 23–25 (1977) discloses 2,6-disubstituted penems of the formula

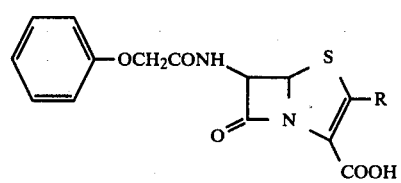

(R not defined)

and reports such penems to be considerably less active than the penicillin and cephalosporin analogs. Also disclosed as antibacterial agents (again without definition of R) are 2-substituted penems of the formula

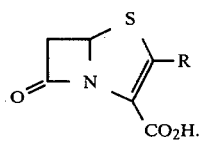

(h) Annual Reports in Medicinal Chemistry, 13, 239–248 (1978) discloses the unsubstituted penem of the formula

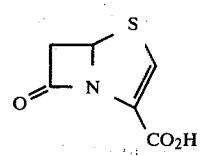

as having no β-lactamase inhibitory activity.

(i) South African Pat. No. 77/6594 discloses 1-carba-2-penem-3-carboxylic acids of the formula

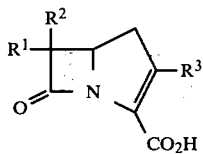

wherein $R^1$, $R^2$ and $R^3$ are independently selected from the group consisting of hydrogen, substituted and unsubstituted: alkyl, alkenyl, cycloalkyl, cycloalkylalkyl, alkylcycloalkyl, aryl, aralkyl, aralkenyl, aralkynyl, heteroaryl, heteroaralkyl, heterocycyl and heterocycylalkyl wherein the substituent or substituents relative to the above-named radicals are selected from the group consisting of amino, hydroxy, alkoxyl, mercapto, alkylthio, arylthio, sulfamoyl, amidino, guanidino, nitro, chloro, bromo, fluoro, cyano and carboxy and wherein the hetero atom in the above-named heterocyclic moiety is selected from the group consisting of oxygen, nitrogen and sulfur. The compounds are reported to have antibiotic activity.

(j) Belgian Pat. No. 866,845 discloses 2-penem compounds of the formula

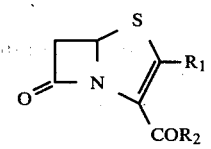

wherein $R_1$ = hydrogen or an organic radical (bonded to the ring carbon atom via a carbon atom) or an etherified mercapto group and $R_2$ is hydrogen or a group $R_2^A$ which forms with CO a protected carboxylic group. The disclosed compounds are reported to be antibacterial agents and β-lactamase inhibitors.

SUMMARY OF THE INVENTION

The present invention provides certain novel 2-substituted and 2,6-disubstituted penem compounds which possess potent antibiotic activity. Also provided are various novel intermediates useful in preparing the biologically active penem derivatives and various processes for the production of the intermediates and active compounds.

The penem ring system has the formula

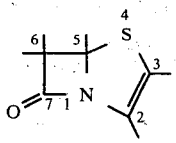

and systematically can be designated as 7-oxo-4-thia-1-azabicyclo[3.2.0]hept-2-ene. For the sake of simplicity, it is named "2-penem" in the present application and the numbering system used is as follows:

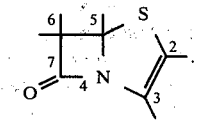

There is thus provided by the present invention the novel 2,6-disubstituted penems having the formula

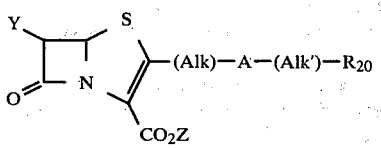

wherein Z is hydrogen or an easily cleavable ester protecting group; Alk represents a $C_1$–$C_2$ alkylene group optionally substituted by a $C_1$–$C_4$ alkyl radical; A is O, S, SO, $SO_2$ or $NR_{21}$ in which $R_{21}$ is hydrogen, (lower)alkyl, phenyl or phenyl(lower)alkyl; Alk' is a $C_2$–$C_4$ alkylene group; $R_{20}$ is a polar substituent selected from the group consisting of —NHOH, —$NR_{22}R_{23}$ in which $R_{22}$ and $R_{23}$ are each independently hydrogen or (lower)alkyl and —$NO_2$; and Y is hydrogen or a radical selected from the group consisting of (a) optionally substituted (lower)aliphatic, (lower)cycloaliphatic or (lower)cycloaliphatic(lower)aliphatic, the substituents being one or more of hydroxy, (lower)alkoxy, optionally substituted phenyloxy, optionally substituted heterocyclicoxy, optionally substituted (lower)alkylthio, optionally substituted phenylthio, optionally substituted heterocyclicthio, mercapto, amino, (lower)alkylamino, di(lower)alkylamino, (lower)alkanoyloxy, (lower)alkanoylamino, optionally substituted phenyl, optionally substituted heterocyclic, carboxy, carb(lower)alkoxy, carbamoyl, N-(lower)alkylcarbamoyl, N,N-di(lower)alkylcarbamoyl, halo, cyano, oxo, thioxo, —$SO_3H$, —O-$SO_3H$, —$SO_2$-(lower)alkyl, (lower)alkylsulfinyl, nitro, phosphono or

in which $R_e$ and $R_r$ are as defined above, the substitutents on the (lower)alkylthio group being one or more of halo, hydroxy, (lower)alkoxy, amino, (lower)alkanoylamino or optionally substituted phenyl or heterocyclic and the phenyl or heterocyclic substituents above being one or more of hydroxy, (lower)alkoxy, halo, (lower)alkyl, halo(lower)alkyl, methanesulfonyl, (lower)alkylthio, amino, (lower)alkanoylamino, (lower)alkanoyloxy, carboxy, carboxy(lower)alkyl, sulfo or sulfo(lower)alkyl;

(b) —OR$_s$ in which R$_s$ is optionally substituted (lower)alkyl or (lower)alkanoyl or optionally substituted phenyl or heterocyclic, the substituents on the alkyl and alkanoyl being one or more of halo, hydroxy, (lower)alkoxy, (lower)alkylamino, di(lower)alkylamino, amino, oxo, (lower)alkanoylamino or optionally substituted phenyl or heterocyclic and the substituents on the phenyl or heterocyclic being one or more of hydroxy, (lower)alkoxy, halo, (lower)alkyl, halo(lower)alkyl, methanesulfonyl, (lower)alkylthio, (lower)alkylamino, di(lower)alkylamino, amino, (lower)alkanoylamino, (lower)alkanoyloxy, carboxy, carboxy(lower)alkyl, sulfo or sulfo(lower)alkyl;

(c) —S(O)$_n$R$_s$ in which n is 0, 1 or 2 and R$_s$ is as defined above;

(d) halo; and (e) optionally substituted phenyl or heterocyclic in which the substituents are one or more of hydroxy, (lower)alkoxy, halo, (lower)alkyl, halo(lower)alkyl, methanesulfonyl, (lower)alkylthio, amino, (lower)alkylamino, di(lower)alkylamino, (lower)alkanoylamino, (lower)alkanoyloxy, carboxy, carboxy(lower)alkyl, sulfo or sulfo(lower)alkyl; or a pharmaceutically acceptable salt thereof.

The compounds of formula I wherein Z is hydrogen (and their pharmaceutically acceptable salts and physiologically hydrolyzed esters) are potent antibacterial agents. The remaining compounds are useful intermediates for preparation of the biologically active penems.

Substituent groups disclosed above for the 2- and 6-positions of the penem ring may be further defined as follows:

(a) Halo includes chlorine, bromine, fluorine and iodine. Preferred halo substituents are chlorine and fluorine;

(b) (Lower)alkyl includes both straight and branched chain saturated aliphatic hydrocarbon radicals having from 1-6 carbon atoms inclusive, e.g. methyl, ethyl, n-propyl, isopropyl, n-butyl, isobutyl, sec-butyl, tert-butyl, n-pentyl, isopentyl, n-hexyl, etc. Preferred (lower)alkyl substituents have from 1-4 carbons and most preferably 1-2 carbons;

(c) (Lower)aliphatic is intended to include acyclic straight and branched chain saturated and unsaturated hydrocarbon radicals having from 1-6 carbon atoms inclusive. The unsaturated radicals may contain one or more double or triple bonds, but preferably contain either one double bond or one triple bond. Examples of (lower)aliphatic are methyl, ethyl, n-propyl, isopropyl, n-butyl, t-butyl, sec-butyl, n-pentyl, isobutyl, vinyl, 1-propenyl, 2-propenyl, isopropenyl, 2-methyl-2-propenyl, ethynyl and 2-propynyl. The most preferred aliphatic radicals are (lower)alkyl as in (b);

(d) (Lower)cycloaliphatic is intended to represent alicyclic saturated and unsaturated hydrocarbon radicals having from 3-8 ring carbon atoms, preferably 3-6 carbon atoms. The unsaturated ring may contain one or more (preferably one) double bond. Examples of this group include cyclopropyl, cyclobutyl, cyclopentyl, cyclohexyl, cycloheptyl, cyclooctyl, cyclopropenyl, cyclopentenyl, 1,3-cyclohexadienyl and cyclohexenyl;

(e) (Lower)cycloaliphatic(lower)aliphatic represents cycloaliphatic-aliphatic radicals having 3-8 carbon atoms (preferably 3-6) in the cycloaliphatic ring and 1-6 carbon atoms (preferably 1-4 and most preferably 1-2) in the aliphatic portion. Examples include cyclopropylmethyl, cyclopropylethyl, cyclopropylpentyl, cyclobutylethyl, cyclopentylmethyl, cyclohexylmethyl, cyclopropenylmethyl, cyclopentenylethyl, cyclopropylethenyl, cyclopropylethynyl, etc. The most preferred radicals of this type are cycloalkyl-alkyl in which the cycloalkyl portion contains 3-6 carbons and the alkyl portion contains 1-2 carbons;

(f) (Lower)alkoxy includes $C_1$-$C_6$ alkoxy radicals, the alkyl portion of which being defined as in (b). Examples include methoxy, ethoxy, n-propoxy, isopropoxy, n-butoxy, isobutoxy, sec-butoxy, n-pentyloxy, etc. Preferred are $C_1$-$C_4$ alkoxy and most preferred are $C_1$-$C_2$ alkoxy;

(g) (Lower)alkylthio includes $C_1$-$C_6$ alkylthio radicals in which the alkyl portion is as defined under (b). Examples include methylthio, ethylthio and n-butylthio;

(h) (Lower)alkylamino includes $C_1$-$C_6$ alkylamino radicals in which the alkyl portion is as under (b). Examples are methylamino, ethylamino, n-propylamino and n-butylamino;

(i) Di(lower)alkylamino represents di $C_1$-$C_6$ alkylamino in which each alkyl is as defined under (b). Examples are dimethylamino and diethylamino;

(j) (Lower)alkanoyloxy represents radicals of the formula

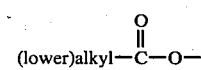

in which alkyl is as defined under (b);

(k) (Lower)alkanoylamino includes radicals of the formula

in which alkyl is as under (b);

(l) Carb(lower)alkoxy represents

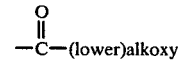

in which (lower)alkoxy is as under (f);

(m) Halo(lower)alkyl represents alkyl radicals in which one or more hydrogen atoms are replaced by a halogen atom;

(n) Sulfo(lower)alkyl represents —$(CH_2)_n SO_3 H$ in which n is 1-6;

(o) Carboxy(lower)alkyl represents —$(CH_2)_n COOH$ in which n is 1-6;

(p) Phenyl(lower)alkyl represents

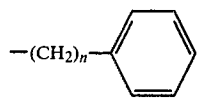

in which n is 1-6;
(q) (Lower)alkanoyl represents

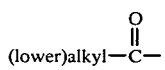

in which alkyl is as under (b);
(r) N-(Lower)alkylcarbamoyl represents

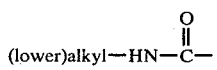

in which alkyl is as under (b);
(s) N,N-Di(lower)carbamoyl represents

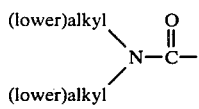

in which each alkyl is as under (b);
(t) (Lower)alkylsulfinyl represents

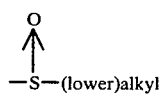

in which (lower)alkyl is as defined above under (b).

The term "heterocyclic" as used herein is intended to include heteromonocyclic and heterobicyclic residues of aromatic character as well as appropriate partially or wholly saturated residues, said heterocyclic residues containing at least one heteroatom selected from oxygen, sulfur and nitrogen and being bonded to the penem ring carbon atom via a ring carbon atom. The preferred heterocyclic groups are either 5- or 6-membered monocyclic radicals or fused 6,6 or 5,6 bicyclic radicals. Illustrative of suitable heterocyclic radicals are the following:

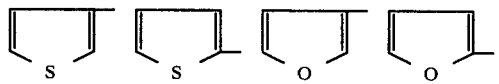

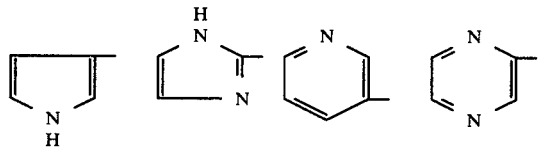

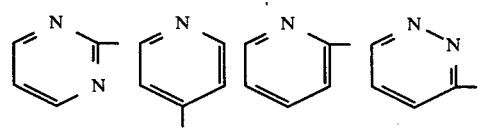

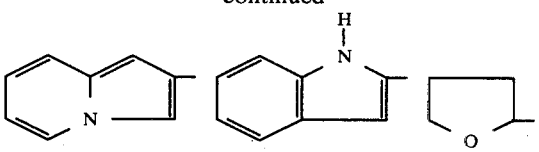

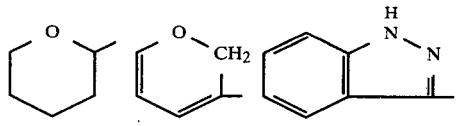

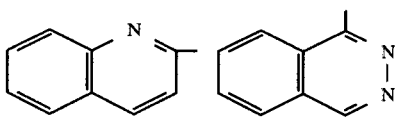

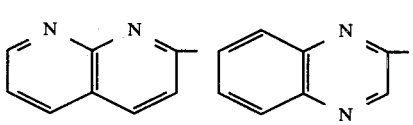

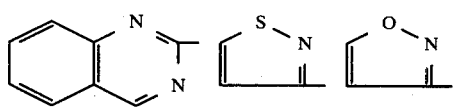

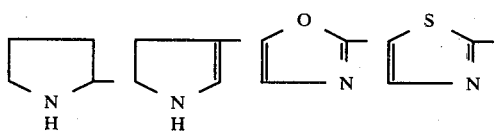

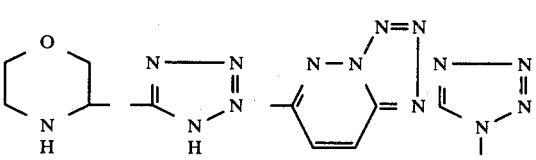

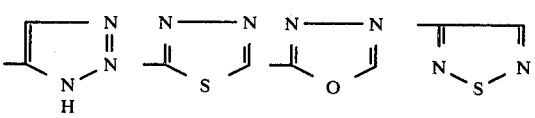

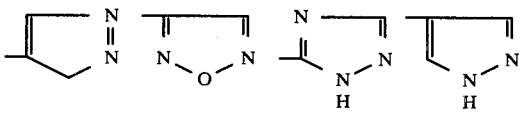

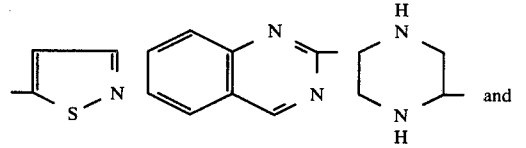 and

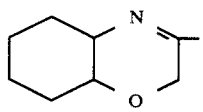

Similarly, the terms heterocyclic-(lower)alkyl, heterocyclic-thio-(lower)alkyl, heterocyclicoxy and heterocyclic-thio represent —(CH$_2$)$_n$-Heterocyclic, —(CH$_2$)$_n$—S-Heterocyclic, —O-Heterocyclic and —S-Heterocyclic, respectively, in which n is 1–6 (preferably 1 or 2).

Since an asymmetric carbon atom is present in the 2-substituted compounds of formula I, such compounds may exist either in the form of racemic mixtures (R,S form) or as the individual dextrorotatory and levorotatory (R- and S-forms) optical isomers. Preferred are the compounds in which the configuration of the 5-carbon atom corresponds to that of natural penicillin (5R-configuration). Substituents at the 5- and 6-positions of the 2,6-disubstituted penems may be in the cis or trans position in relation to one another. Where the penem 6-substituent contains an asymmetric carbon atom, the resulting isomers are identified herein as isomers A, B, C and D (see Example 5 for stereochemistry). The preferred isomer in compounds of this type is isomer B. Separation of the various optical and geometric isomers may be carried out by conventional separation and resolution procedures well-known to those skilled in the art.

The present invention is intended to include the compounds of formula I in the form of isomer mixtures and also in the form of the individual separated and resolved isomers.

The pharmaceutically acceptable salts referred to above include the nontoxic carboxylic acid salts, e.g. nontoxic metallic salts such as sodium, potassium, calcium, aluminum and magnesium, the ammonium salt and salts with nontoxic amines such as trialkylamines (triethylamine), procaine, dibenzylamine, N-benzyl-$\beta$-phenethylamine, 1-ephenamine, N,N'-dibenzylethylenediamine, N-alkylpiperidine and other amines which have been used to form salts of penicillins and cephalosporins. When a basic group is present, the present invention also includes the pharmaceutically acceptable acid addition salts, e.g. salts with mineral acids such as hydrochloric, hydrobromic, hydroiodic, phosphoric, sulfuric or with suitable organic carboxylic acids or sulfonic acids such as trifluoroacetic, p-toluenesulfonic, maleic, acetic, citric, oxalic, succinic, benzoic, tartaric, fumaric, mandelic, ascorbic and malic. Compounds containing an acid group and a basic group can also be in the form of inner salts, i.e. a zwitterion. Preparation of the above-described salts may be carried out according to conventional procedures for forming salts of $\beta$-lactam antibiotics such as penicillins and cephalosporins.

The term "easily removable ester protecting group" is one which has acquired a definite meaning within the $\beta$-lactam and peptide art. Many such groups are known which are used to protect the carboxyl group during subsequent chemical reactions and which may later be removed by standard methods to give the free carboxylic acid. Known ester protecting groups include 2,2,2-trichloroethyl, tertiary alkyl of from 4–6 carbon atoms, tertiary alkenyl of from 5–7 carbon atoms, tertiary alkynyl of from 5–7 carbon atoms, alkoxymethyl, alkanoylmethyl of from 2–7 carbon atoms, N-phthalimidomethyl, benzoylmethyl, halobenzoylmethyl, benzyl, p-nitrobenzyl, o-nitrobenzyl, benzhydryl, trityl, trimethylsilyl, triethylsilyl, $\beta$-trimethylsilylethyl, and the like. Choice of an ester protecting group is dependent on the subsequent reaction conditions the group must withstand and the conditions desired for removing it. Selection of a suitable group is well within the ability of one skilled in the art. For use as a chemical intermediate the most preferred ester is the p-nitrobenzyl ester which can be readily removed by catalytic hydrogenation. For preparation of compounds containing functional groups reducible under such removal conditions, a preferred alternative is the $\beta$-trimethylsilylethyl ester removable by treatment with fluoride ions. Also included within the scope of easily removable ester protecting groups are physiologically cleavable esters, i.e. those esters known in the penicillin and cephalosporin art to be easily cleaved within the body to the parent acid. Examples of such physiologically cleavable esters include indanyl, phthalidyl, methoxymethyl, glycyloxymethyl, phenylglycyloxymethyl, thienylglycyloxymethyl or acyloxymethyl of the formula

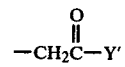

in which Y' is $C_1$–$C_4$ alkyl or phenyl. Particularly preferred esters of this type are methoxymethyl, acetoxymethyl, pivaloyloxymethyl, phthalidyl and indanyl.

It will be appreciated that the compounds of formula I may exist in various states of solvation and the anhydrous as well as solvated (including hydrates) forms are intended to be within the scope of the invention.

With respect to the compounds of formula I, the preferred compounds are those wherein Y is hydrogen or (lower)alkyl optionally substituted (preferably at the $\alpha$-carbon) by hydroxy. More preferred compounds within the above group are those wherein Y is hydrogen, ethyl or $\alpha$-hydroxyethyl. Still more preferred compounds of formula I are those wherein Y is hydrogen or $\alpha$-hydroxyethyl. The most preferred compounds are those wherein Y is $\alpha$-hydroxyethyl.

A preferred embodiment of the present invention consists of the compounds of formula I wherein the 2-substituent is

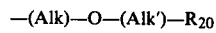

in which Alk, Alk' and $R_{20}$ are as defined above. Examples of substituents included within this class include
—CH$_2$OCH$_2$CH$_2$NH$_2$, —CH$_2$CH$_2$OCH$_2$CH$_2$NH$_2$, —CH$_2$OCH$_2$CH$_2$NHCH$_3$, —CH$_2$OCH$_2$CH$_2$N(CH$_3$)$_2$, —CH$_2$OCH$_2$CH$_2$NHC$_2$H$_5$, —CH$_2$OCH$_2$CH$_2$N(C$_2$H$_5$)$_2$, —CH$_2$OCH$_2$CH$_2$NHC$_3$H$_7$, —CH$_2$OCH$_2$CH$_2$N(C$_3$H$_7$)$_2$, —CH$_2$OCH$_2$CH$_2$CH$_2$NH$_2$, —CH$_2$OCH$_2$CH$_2$CH$_2$NH$_2$, —CH$_2$OCH$_2$CH$_2$CH$_2$NHCH$_3$, —CH$_2$OCH$_2$CH$_2$CH$_2$N(CH$_3$)$_2$, —CH$_2$CH$_2$OCH$_2$CH$_2$NHCH$_3$, —CH$_2$CH$_2$OCH$_2$CH$_2$N(CH$_3$)$_2$, —CH$_2$CH$_2$OCH$_2$CH$_2$CH$_2$NH$_2$, —CH$_2$CH$_2$OCH$_2$CH$_2$CH$_2$NHCH$_3$, —CH$_2$CH$_2$OCH$_2$CH$_2$CH$_2$N(CH$_3$)$_2$, —CH$_2$CH—OCH$_2$CH$_2$NH$_2$,

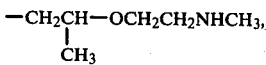

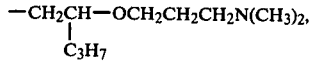

—CH$_2$OCH$_2$CH$_2$NHOH, —CH$_2$OCH$_2$CH$_2$CH$_2$NHOH, —CH$_2$CH$_2$OCH$_2$CH$_2$NHOH, —CH$_2$OCH$_2$CH$_2$NO$_2$, —CH$_2$OCH$_2$CH$_2$CH$_2$NO$_2$, —CH$_2$CH$_2$OCH$_2$CH$_2$NO$_2$,

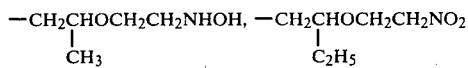

and —CH$_2$OCH$_2$CH$_2$CH$_2$CH$_2$NHOH. Within this class of compounds, the preferred members are those wherein Y is hydrogen, ethyl or α-hydroxyethyl. Most preferred members have Y=hydrogen or α-hydroxyethyl and especially Y=α-hydroxyethyl.

Another preferred embodiment of the present invention consists of the compounds of formula I wherein the 2-substituent is —(Alk)—S—(Alk')—R$_{20}$ in which Alk, Alk' and R$_{20}$ are as defined above. Examples of substituents within this class include
—CH$_2$SCH$_2$CH$_2$NH$_2$, —CH$_2$CH$_2$SCH$_2$CH$_2$NH$_2$,
—CH$_2$SCH$_2$CH$_2$CH$_2$NH$_2$,
—CH$_2$SCH$_2$CH$_2$CH$_2$CH$_2$NH$_2$,
—CH$_2$SCH$_2$CH$_2$NHCH$_3$, —CH$_2$SCH$_2$CH$_2$N(CH$_3$)$_2$,
—CH$_2$SCH$_2$CH$_2$NHC$_2$H$_5$, —CH$_2$SCH$_2$CH$_2$N(C$_2$H$_5$)$_2$,
—CH$_2$SCH$_2$CH$_2$NHC$_4$H$_9$, —CH$_2$SCH$_2$CH$_2$N(C$_4$H$_9$)$_2$,
—CH$_2$SCH$_2$CH$_2$CH$_2$NHCH$_3$,
—CH$_2$SCH$_2$CH$_2$CH$_2$N(CH$_3$)$_2$,
—CH$_2$SCH$_2$CH$_2$CH$_2$N(C$_3$H$_7$)$_2$,
—CH$_2$SCH$_2$CH$_2$CH$_2$CH$_2$NHCH$_3$,
—CH$_2$CH$_2$SCH$_2$CH$_2$CH$_2$NH$_2$,
—CH$_2$CH$_2$SCH$_2$CH$_2$NH$_2$,

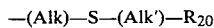

—CH$_2$SCH$_2$CH$_2$NHOH, —CH$_2$SCH$_2$CH$_2$CH$_2$NHOH, —CH$_2$SCH$_2$CH$_2$CH$_2$CH$_2$NHOH,
—CH$_2$CH$_2$SCH$_2$CH$_2$NHOH,
—CH$_2$CH$_2$SCH$_2$CH$_2$CH$_2$NHOH,

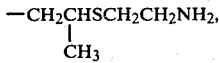

—CH$_2$SCH$_2$CH$_2$NO$_2$, —CH$_2$SCH$_2$CH$_2$CH$_2$NO$_2$,
—CH$_2$SCH$_2$CH$_2$CH$_2$CH$_2$NO$_2$, —CH$_2$CH$_2$SCH$_2$CH$_2$NO$_2$ and —CH$_2$CH$_2$SCH$_2$CH$_2$CH$_2$NO$_2$. Within this class of compounds, the preferred members are those wherein Y is hydrogen, ethyl or α-hydroxyethyl. Most preferred members have Y=hydrogen or α-hydroxyethyl and especially Y=α-hydroxyethyl.

An especially preferred embodiment of the present invention consists of the following compounds included within formula I:
(a) Y=H; 2-CH$_2$OCH$_2$CH$_2$NH$_2$;
(b) Y=α-hydroxyethyl; 2-CH$_2$OCH$_2$CH$_2$NH$_2$;
(c) Y=H; 2-CH$_2$OCH$_2$CH$_2$NHOH;
(d) Y=α-hydroxyethyl; 2-CH$_2$OCH$_2$CH$_2$NHOH;
(e) Y=H; 2-CH$_2$SCH$_2$CH$_2$NH$_2$;
(f) Y=α-hydroxyethyl; 2-CH$_2$SCH$_2$CH$_2$NH$_2$;
(g) Y=H; 2-CH$_2$SCH$_2$CH$_2$NHOH;
(h) Y=α-hydroxyethyl; 2-CH$_2$SCH$_2$CH$_2$NHOH;
(i) Y=H;

(j) Y=α-hydroxyethyl;

(k) Y=H;

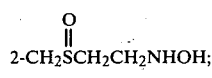

(l) Y=α-hydroxyethyl;

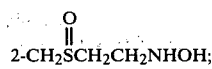

(m) Y=H; 2-CH$_2$OCH$_2$CH$_2$NO$_2$;
(n) Y=α-hydroxyethyl; 2-CH$_2$OCH$_2$CH$_2$NO$_2$;
(o) Y=H; 2-CH$_2$SCH$_2$CH$_2$NO$_2$;
(p) Y=α-hydroxyethyl; 2-CH$_2$SCH$_2$CH$_2$NO$_2$;
(q) Y=H;

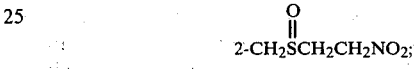

and
(r) Y=α-hydroxyethyl;

Especially preferred are the above-described compounds where Z in formula I is hydrogen, pharmaceutically acceptable salts thereof and physiologically cleavable esters thereof such as acetoxymethyl, methoxymethyl, pivaloyloxymethyl, phthalidyl and indanyl.

Most preferred compounds of the present invention are those where Y=hydrogen or, more preferably, α-hydroxyethyl, and the 2-substituent is —CH$_2$OCH$_2$CH$_2$NH$_2$, most especially the free acids, pharmaceutically acceptable salts thereof and physiologically cleavable esters thereof.

In another aspect the present invention comprises novel intermediates of the formula

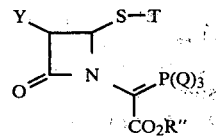

wherein Y is as defined above in regard to compounds of formula I, Q is phenyl or (lower)alkyl, R" is an easily removable ester protecting group and T is

wherein X is —(Alk)—A—(Alk')—R$_{20}$.

In the intermediates of formula II, Q is preferably phenyl, R" is preferably p-nitrobenzyl and X and Y are preferably those substituent groups mentioned as being preferred in connection with the compounds of formula I. Reactive functional groups such as mercapto, amino and hydroxy in substituents X and Y may be protected by conventional blocking groups during conversion of the intermediates to biologically active end-products. For example, $R_{20}$ in intermediate II may be $-N_3$ which on catalytic hydrogenation will be converted to a free amino group.

Compound I may be prepared by one or more of the reaction routes discussed below. The various synthetic routes may be divided into three main processes depending on the stage of incorporation of the 6-substituent, i.e. Y. Thus, in Process I, the 6-substituent is incorporated in the basic starting material; Process II involves incorporation of Y at the end of the synthesis and in Process III substituent Y is incorporated in mid-synthesis. Each of the three main processes in turn can vary in the procedure for incorporating the desired 2-substituent, i.e. X in the schemes shown below. In general, it is preferred to incorporate substituent Y in mid-synthesis and to incorporate substituent X by acylation of the mercaptide intermediates III or $III_a$ shown below since these procedures have been found to be the most generally useful.

The steps of Process I may be seen from the following scheme:

Process I (Variation 1): Early incorporation of 2-substituent

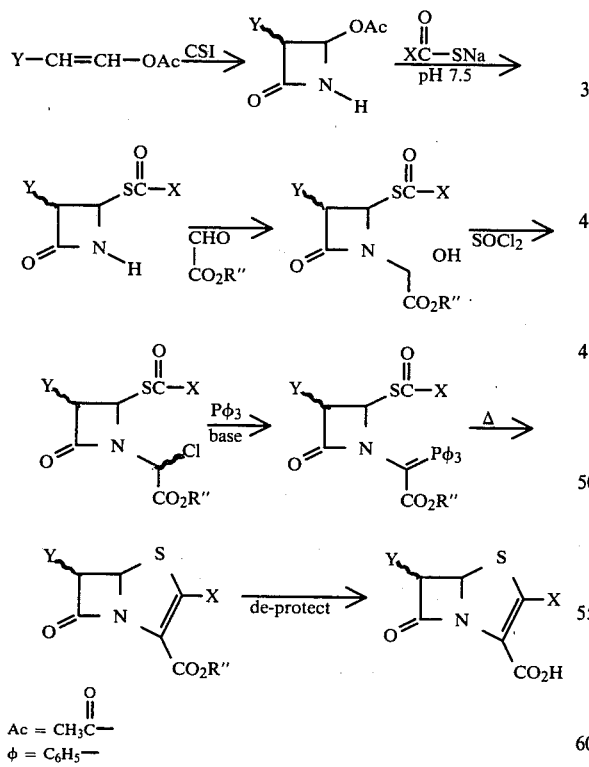

Ac = $CH_3C-\overset{O}{\underset{\|}{}}$
φ = $C_6H_5-$

Process I (Variation 2): Late incorporation of 2-substituent

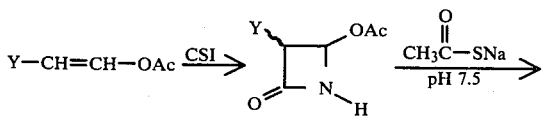

Process I (Variation 3): Late incorporation of 2-substituent

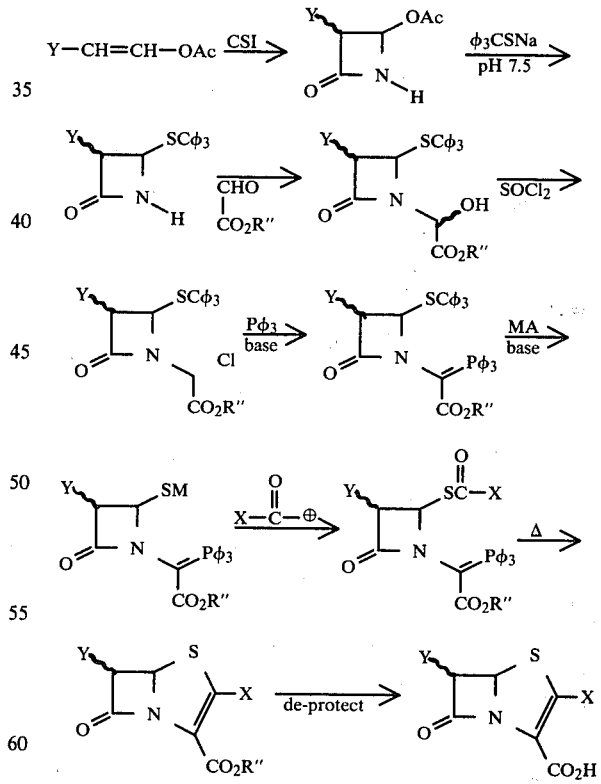

$X-\overset{O}{\underset{\|}{C}}-\oplus$ = acylating agent
MA = heavy metal salt In Process I a vinyl ester (Y=H or a radical as defined in connection with compounds I) containing the desired 6-substituent is converted to the optionally 1-substituted 4-acetoxy-2-azetidinone by a cycloaddition reaction with chloro sulfonyl isocyanate (CSI) followed by reduction with an organic reducing agent such as sodium sulfite. The CSI reaction is conventionally carried out in an inert organic solvent such as diethyl ether at a temperature of 0° C. or below. The reduction step may be conducted in an aqueous or aqueous-organic reaction mixture at a temperature of 0° or below and at a slightly basic pH.

Following formation of the 4-acetoxy-2-azetidinone, Process I may be separated into three different paths. In one route (Variation 1) the azetidinone is reacted with a thiolic acid

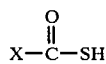

wherein X is as defined in connection with compounds I, or a salt thereof, in a suitable solvent (e.g. aqueous or aqueous organic). Displacement of the acetoxy group results in incorporation of the desired 2-substituent in the azetidinone at this stage. The displacement reaction is preferably carried out at room temperature or below and at a slightly basic pH ($\sim$7.5). When Y$\neq$H, cis and trans isomers of the resulting azetidinone are preferably separated (e.g. by chromatography) at this point in the process. Variations 2 and 3 depicted above convert the 4-acetoxy-2-azetidinone into the 4-acetylthio-2-azetidinone and 4-tritylthio-2-azetidinone products, respectively, by nucleophic displacement with thioacetic acid or triphenylmethyl mercaptan (or a salt thereof such as the sodium salt), respectively.

The 4-thio azetidinone is next reacted with a glyoxylate ester

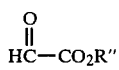

wherein R" is an easily removable ester protecting group such as p-nitrobenzyl or trimethylsilylethyl, or a reactive oxo derivative thereof such as a hydrate, in an inert organic solvent (e.g. benzene, toluene, xylene, and the like) and preferably at an elevated temperature (e.g. 50° C. up to most preferably reflux temperature). When a hydrate of the ester is employed, resulting water may be removed azeotropically or with molecular sieves. The hydroxy ester product is formed as a mixture of epimers which can be optionally purified as by chromatography or used directly in the next step.

Conversion of the hydroxy ester to the corresponding chloro ester is achieved by reaction with a chlorinating reagent (e.g. SOCl$_2$, POCl$_3$, PCl$_5$, and the like) in an inert organic solvent (e.g. tetrahydrofuran, diethyl ether, methylene chloride, dioxane, and the like) in the presence or absence of a base, preferably an aliphatic tertiary amine (e.g. triethylamine) or a heterocyclic tertiary amine (e.g. pyridine or collidine). The reaction is advantageously run at from about $-10°$ C. to room temperature. Chloro ester products is obtained as a mixture of epimers which can optionally be purified before use in the next step.

The phosphorane intermediate may be obtained by reaction of the chloro ester with a suitable phosphine (preferably triphenylphosphine or a tri(lower)alkyl phosphine such as triethylphosphine or tri-n-butyl phosphine) in an inert organic solvent such as dimethylformamide, dimethylsulfoxide, tetrahydrofuran, dimethoxyethane, dioxane or an aliphatic, cycloaliphatic or aromatic hydrocarbon (e.g. hexane, cyclohexane, benzene, toluene, and the like) in the presence of a base, preferably an organic tertiary amine such as triethylamine, pyridine or 2,6-lutidine. The reaction is advantageously carried out at temperatures from room temperature to the reflux temperature of the solvent system.

At this stage the process again diverges into two routes. In Variation I (where the 2-substituent has already been incorporated), the phosphorane intermediate is converted to the desired penem by thermally cyclizing in an inert organic solvent at a temperature of from just above room temperature to the reflux temperature of the solvent system. Most conveniently, the cyclization is carried out under reflux conditions. Suitable inert organic solvents include aliphatic, cycloaliphatic or aromatic hydrocarbons (e.g. benzene, toluene, hexane, cyclohexane), halogenated hydrocarbons (e.g. methylene chloride, chloroform, carbon tetrachloride), ethers (diethyl ether, dioxane, tetrahydrofuran, dimethoxyethane), carboxylic acid amides (e.g. dimethylformamide), di $C_1$–$C_6$ alkylsulfoxides (e.g. dimethylsulfoxide) or a $C_1$–$C_6$ alkanol (e.g. methanol, ethanol, t-butanol), or a mixture thereof.

In variations 2 and 3 the phosphorane is converted to a heavy metal mercaptide of the formula

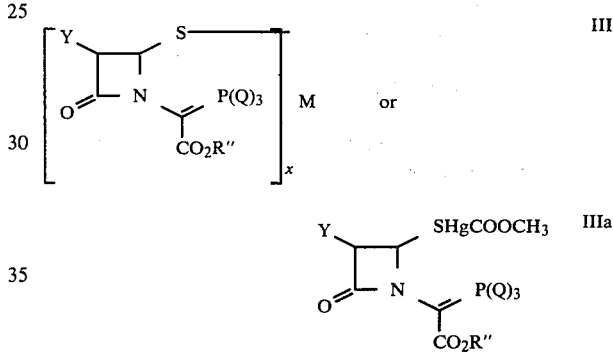

wherein Y is as defined above with respect to compounds of formula I, R" is an easily removable ester group, Q is preferably phenyl or (lower)alkyl, x is 1 or 2 and M is Cu(II), Pb(II) or Hg(II) when x is 2 or Ag(I) when x is 1. Mercaptide formation is accomplished by reaction of the phosphorane with a salt of Hg(II), Pb(II), Cu(II) or Ag(I) or with (methoxycarbonyl)mercury(II) acetate in a methanol-containing solvent and in the presence of an organic or inorganic base such as aniline, pyridine, collidine, 2,6-lutidine, an alkali metal carbonate, and the like. A preferred base is pyridine. The reaction may be carried out at room temperature or, if desired, with moderate cooling or heating. The anion (A) of the heavy metal salt may be any anion which gives a soluble salt in the selected solvent, e.g. NO$_3^-$, CH$_3$COO$^-$, BF$_4^-$, F$^-$, ClO$_4^-$, NO$_2^-$, CNO$^-$, etc. The mercaptide intermediate is then reacted with an acylating agent capable of introducing the moiety

wherein X is the desired penem 2-substituent. The acylating agent

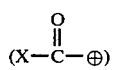

may be the acid $$X-\overset{O}{\underset{\|}{C}}-OH \quad \quad 5$$

or a reactive functional derivative thereof such as an acid halide (preferably acid chloride), acid azide, acid anhydride, mixed acid anhydride, active ester, active thioester, etc. Acylation is conducted in an inert solvent (e.g. a halogenated hydrocarbon such as methylene chloride or an ether such as dioxane, tetrahydrofuran or diethyl ether) and, when an acid derivative is used, in the presence of an acid acceptor such as a tri(lower)alkylamine (e.g. triethylamine) or a tertiary organic base such as pyridine, collidine or 2,6-lutidine. When the free acid is employed, the acylation is conducted in the presence of a suitable condensing agent, for example a carbodiimide such as N,N'-dicyclohexylcarbodiimide. Acylation of the mercaptide can be achieved over a wide temperature range, but is preferably carried out from about $-20°$ to $+25°$ C. Following acylation, the resulting phosphorane is cyclized as described above to give the desired penem ester.

Formation of the phosphorane via the mercaptide intermediate (Variations 2 and 3) has been found to result in product of much better purity than that obtained by the more conventional route of Variation 1.

Once the carboxyl-protected penem is formed, the protecting group may be removed by conventional de-blocking procedures (e.g. hydrolysis, hydrogenation or photolysis) to give the de-blocked penem. Removal of the p-nitrobenzyl ester, for example, may be achieved by catalytic hydrogenation in the presence of a noble metal catalyst such as palladium or rhodium, including derivatives thereof such as oxides, hydroxides or halides, said catalyst being optionally supported on a conventional carrier such as carbon or diatomaceous earth. A non-reducible aqueous or non-aqueous inert solvent such as water, ethanol, methanol, ethyl acetate, tetrahydrofuran, diethyl ether or dioxane is used. Hydrogenation may be conducted at atmospheric or elevated pressure and is conveniently run at room temperature for a period of from about 1-5 hours depending on the solvent and catalyst used. If an equivalent weight of a base such as an alkali metal or alkaline earth metal hydroxide or an amine is employed during the hydrogenation, the product may be recovered in the form of a carboxylic acid salt. Removal of the β-trimethylsilylethyl ester, another useful protecting group, is conveniently achieved by treatment with a source of fluoride ions. Other ester protecting groups can be similarly removed by methods well-known to those skilled in the art.

In a second main process (Process II), the reaction sequence is as shown below:

Process II (Variation 1):
Early incorporation of 2-substituent

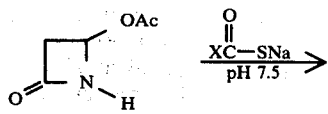

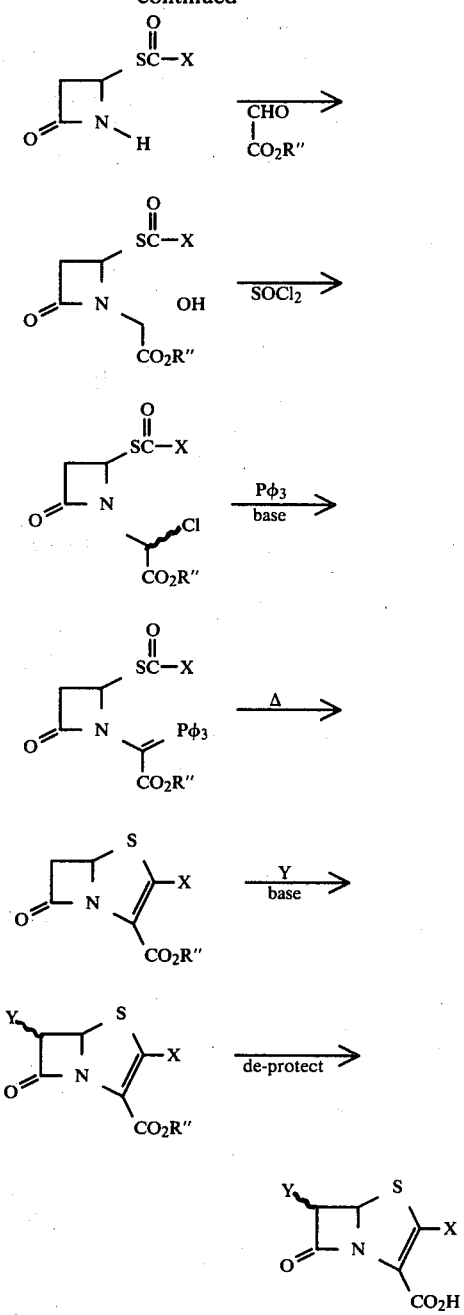

Process II (Variation 2):
Late incorporation of 2-substituent

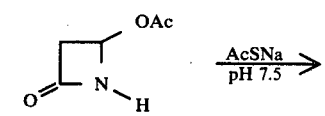

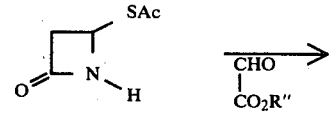

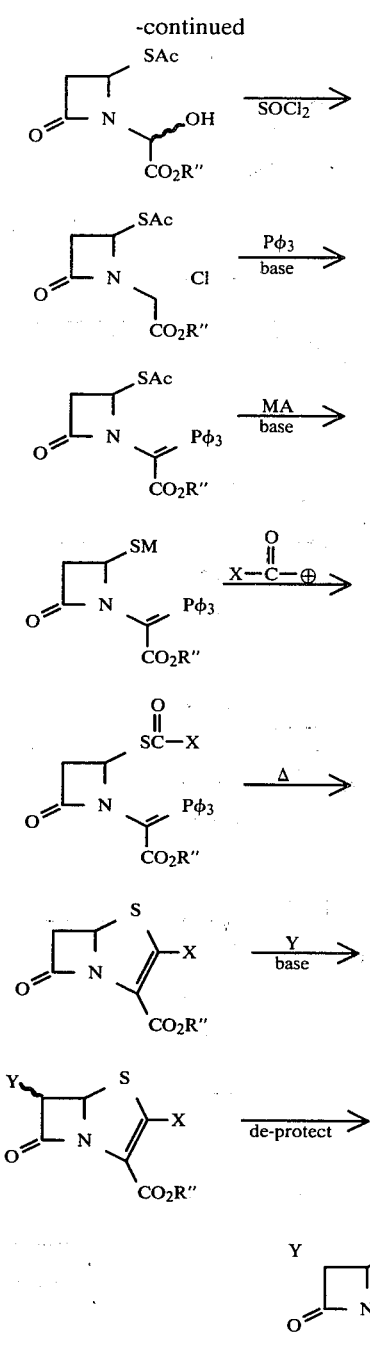

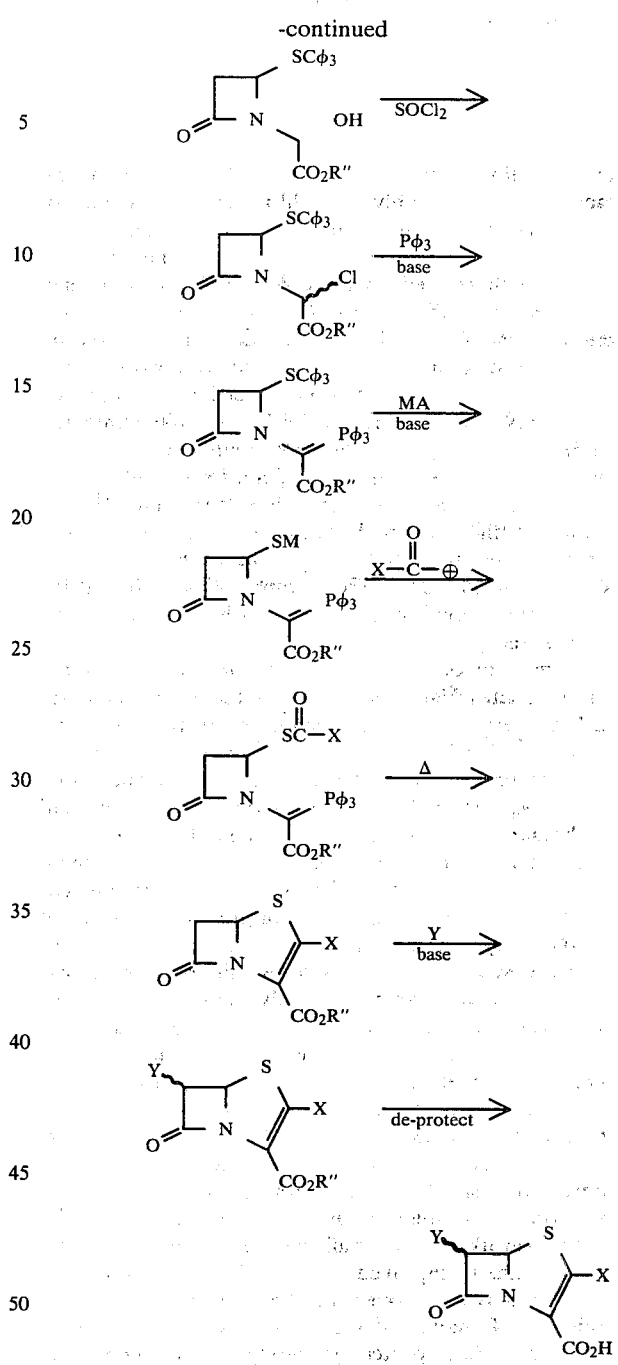

Process II (Variation 3):
Late incorporation of 2-substituent

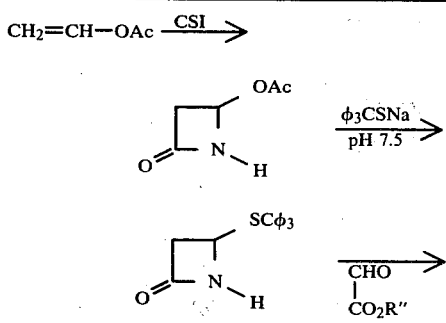

As can be seen Process II is substantially the same as Process I (except that Y must be H) up through the thermal cyclization step which produces the 2-substituted penem. A 6-substituent, however, if desired, is now incorporated at this stage by reaction of the 2-penem with a suitable electrophile in an inert solvent (e.g. tetrahydrofuran, diethyl ether, dimethoxyethane, and the like) and in the presence of a strong base. In this procedure the 2-penem can be reacted in the form of the free acid (obtained by de-blocking as described above) in the presence of about two equivalents of base or, alternatively, a suitable 2-penem ester may be used in the presence of about the equivalent of base. Any ester inert to anion chemistry (the reaction involves anion formation with base followed by reaction of the electrophile with the penem anion) may be employed, e.g. (lower)alkyl such as methyl, ethyl, n-propyl or t-butyl, phenyl, trichloroethyl, methoxymethyl, silyl such as trimethylsilyl or t-butyldimethylsilyl, and the like. Penem esters having activated methylene groups such as p-nitrobenzyl are not suitable and, if the 2-penem ester is of this type, it must be first de-blocked and either used as the free acid or converted to a suitable ester. The particular base used is not critical and the usual strong bases such as sodium hydride, phenyl lithium or butyl lithium are suitable. Most preferably, however, a lithium disilylamide or a lithium dialkylamide such as lithium dicyclohexylamide (LDCA), lithium diethylamide, lithium dimethylamide or lithium di-isopropylamide (LDA) is used. The electrophile is selected so as to generate the desired Y-substituent upon reaction with the anion and may be, for example, a halogen (e.g. Br$_2$, I$_2$), an alkyl halide (e.g. CH$_3$I) or a similar halide such as an aliphatic, cycloaliphatic, cycloaliphatic-aliphatic, phenyl(lower)alkyl, heterocyclic, heterocyclic-thio, heterocyclicthio-(lower)alkyl, or heterocyclic-(lower)alkyl, halide, a tosylate or mesylate (e.g.

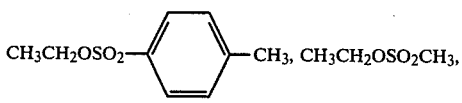

$\phi$CH$_2$CH$_2$CH$_2$OSO$_2$CH$_3$, etc.), an epoxide (e.g.

), an episulfide (e.g.

), an aldehyde (e.g. CH$_3$CHO, C$_6$H$_5$CH$_2$CHO), a ketone (e.g. CH$_3$COCH$_3$,

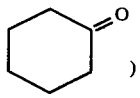)

or an ester (e.g. CH$_3$CH$_2$COOCH$_3$ or C$_6$H$_5$COOCH$_3$). Representative examples of other suitable electrophiles are shown below:

CH$_2$=CH—CH$_2$Br

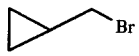

O
||
CH$_3$CCH=CH$_2$

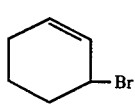

Br
||
CH$_3$CH—CH$_3$

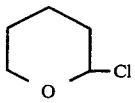

HCHO

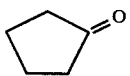

CH$_3$SSO$_2$CH$_3$ $\phi$CH=CHCHO

O
||
CH$_3$CCH$_2$Cl $\phi$CH$_2$Br $\phi$C≡CCH$_2$Br

CH$_2$SCH$_2$Cl $\phi$OCH$_2$Cl

A most preferred electrophile is acetaldehyde which gives rise to the hydroxyethyl 6-substituent. Introduction of the 6-substituent by this process is preferably carried out with cooling (e.g. −80° to 0° C.) according to the general procedure described in *Canadian Journal of Chemistry*, 50(19), 3196–3201 (1972).

After formation of the desired 2,6-penem, any ester protecting group may be removed as discussed above to give the de-protected product.

The third main reaction process (Process III) can be understood from the following scheme:

Process III (Variations 1 and 2):

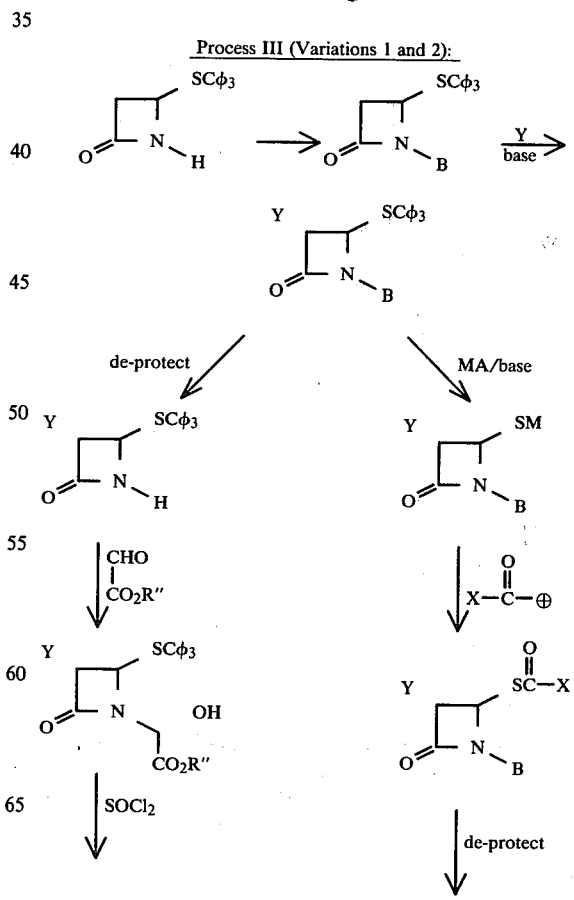

-continued
Process III (Variations 1 and 2):

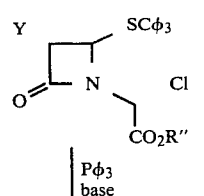
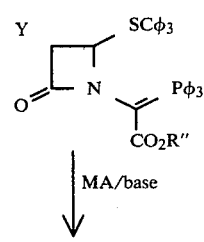
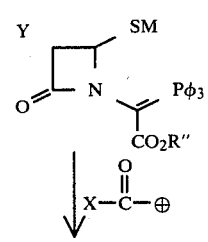
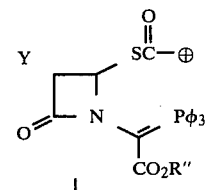
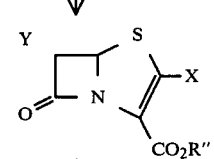
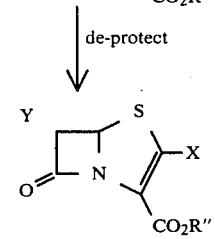

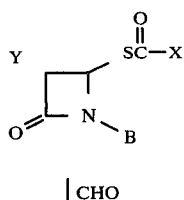
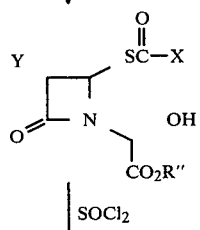
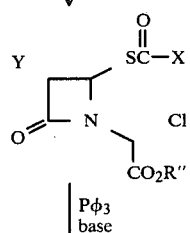
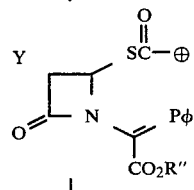
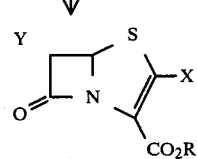
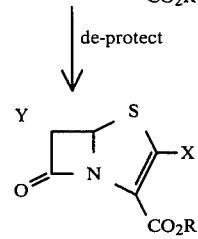

B = blocking group for ring nitrogen

The 4-tritylthio-2-azetidinone of Process III is formed as described in Process II (Variation 3). The ring nitrogen of the azetidinone is then protected by a conventional easily removable blocking group such as triorganosilyl (e.g. trimethylsilyl or t-butyldimethylsilyl), methoxymethyl, methoxyethoxymethyl, tetrahydropyranyl, and the like. Introduction of the desired Y-substituent at the 1-position of the azetidinone is then achieved by reaction of an appropriate electrophile with the N-protected azetidinone in the presence of a strong base (reaction conditions as described above in connection with Process II). At this point the process diverges into two routes depending on the time of deblocking the azetidinone.

In one route the N-protected intermediate is deblocked by conventional procedures (e.g. acid hydrolysis) and then converted to the 2,6-penem via ester formation, chlorination of the hydroxy ester, conversion of the chloro ester to a phosphorane, conversion of the phosphorane to a heavy metal mercaptide, acylation of the mercaptide with

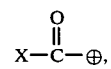

thermal cyclization of the resulting phosphorane to give the 2,6-penem ester and removal of the carboxyl-protecting group. Reaction conditions for these steps are as disclosed in connection with Process II (Variation 3).

An alternative route involves the steps of converting the N-protected azetidinone to a heavy metal mercaptide, acylating the mercaptide with the moiety

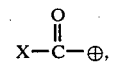

removing the N-protecting group, reacting the deprotected azetidinone with the glyoxylate ester, chlorinating, reacting the chloro ester with the phosphine to give the phosphorane, cyclizing the phosphorane to give the penem ester and removing the carboxyl-protecting group to give the 2,6-penem. Reaction conditions for these steps are as disclosed previously.

In preparing the 2-penem of 2,6-penem compounds according to the above processes, free functional groups in substituents X or Y which do not participate in the reaction may be temporarily protected in a manner which is itself known, such as free amino groups by acylation, tritylation or silylation, free hydroxyl groups, for example, by etherification or esterification, mercapto groups by esterification, and free carboxyl or sulfo groups, for example, by esterification, including silylation. After the reaction has taken place, these groups can, if desired, be liberated, individually or jointly, in a manner which is itself known.

Additionally, it is possible in compounds of formula I to functionally modify the 2- and/or 2,6-substituents during or at the conclusion of the reaction procedures according to known processes to obtain other substituents included within the scope of the present invention. Thus, for example, carbonyl groups can be reduced to alcohol groups, unsaturated aliphatic groups can be halogenated, amino groups can be alkylated or acylated, nitro groups can be converted to hydroxyamino and amino groups, hydroxyl groups can be etherified or esterified, etc.

The penem free acid compounds may be converted to pharmaceutically acceptable salts thereof or to easily removable esters thereof (particularly physiologically cleavable esters). Salts may be formed by reaction of the free acid with a stoichiometric amount of a suitable non-toxic acid or base in an inert solvent followed by recovery of the desired salt as by lyophilization or precipitation. Esters (in particular physiologically cleavable esters) may be prepared in an analogous manner to preparation of the corresponding esters of penicillins and cephalosporins. Resulting mixtures of isomers can be separated into the individual isomers according to known methods. Mixtures of diastereomeric isomers, for example, can be separated by fractional crystallization, adsorption chromatography (column or thin-layer) or other suitable separation methods. Resulting racemates can be resolved into the antipodes in the customary manner, for example by forming a mixture of diastereomeric salts with optically active salt-forming reagents, separating the diasteromeric salts and converting the salts into the free compounds, or by fractional crystallization from optically active solvents.

The present invention also comprises those embodiments according to which compounds used as intermediate products are used as starting materials and the remaining process steps are carried out with these, or the process is discontinued at any stage. Furthermore, starting materials can be used in the form of derivatives or can be formed during the reaction.

The free acid penem compounds provided by the present invention and pharmaceutically acceptable salts and physiologically cleavable esters of said acids have been found to be potent broad-spectrum antibacterial agents useful in the treatment of infectious diseases in animals, including man, caused by both Gram-negative and Gram-positive organisms. The compounds are also of value as nutritional supplements in animal feeds and as agents for the treatment of mastitis in cattle.

The 2-penem acids (and physiologically cleavable esters and pharmaceutically acceptable salts thereof) provided according to the present invention (i.e. compounds of general formula I wherein Y=H) possess antibacterial activity per se and are also useful intermediates (preferably in their carboxyl-protected form) for preparing the 2,6-disubstituted penems I via anion formation and reaction with an electrophile.

The active compounds provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered orally or parenterally in an amount of from about 5 to 200 mg./kg./day and preferably about 5 to 20 mg./kg./day in divided dosage, e.g. three or four times a day. They are administered in dosage units containing, for example, 125, 250 or 500 mg. of active ingredient with suitable physiologically acceptable carriers or diluents.

The present invention also provides a method of combatting bacterial infections in animals, particularly warm-blooded animals, which comprises administering an acid of formula I or a physiologically cleavable ester thereof or a pharmaceutically acceptable salt thereof, or a pharmaceutical composition thereof, to an infected host in an amount sufficient to combat such infection.

Illustrative examples of the preparation of starting materials and end-products of the present invention follow. All temperatures are in degrees Centigrade. For the sake of convenience, certain abbreviations are employed in the examples. Definitions of the less obvious of these abbreviations are as follows:

| | |
|---|---|
| CSI | chlorosulfonyl isocyanat |
| pet. ether | petroleum ether |
| b.p. | boiling point |
| n.m.r. | nuclear magnetic resonance |
| h | hour |
| ether | diethyl ether (unless otherwise indicated) |
| Celite | Trademark of Johns-Manville Products Corporation for diatomaceous earth |
| psi | pounds per square inch |
| r.t. | room temperature |
| PNB | p-nitrobenzyl |
| m.p. | melting point |
| LAH | lithium aluminum hydride |
| n-BuLi | n-butyl lithium |
| MIBK | methyl isobutyl ketone |
| Et | $C_2H_5-$ |
| Tr | $-C(C_6H_5)_3$ |
| Me | $CH_3-$ |
| THF | tetrahydrofuran |
| Ph | phenyl |
| DMF | dimethylformamide |
| TEA | triethylamine |
| PNBG | p-nitrobenzyl glyoxylate |
| THP | tetrahydropyranyl |
| TFA | trifluoroacetic acid |
| HMPT (or HMPA) | hexamethylphosphorus triamide |
| LDA | lithium diisopropyl amide |
| Ac | $CH_3CO-$ |
| Ms | $CH_3SO_2-$ |
| DMAP | 4-dimethylaminopyridine |

PREPARATION OF STARTING MATERIALS

Preparation of 4-Tritylthio-2-azetidinone Intermediates 1. 1-(Trimethylsilyl)-4-tritylthio-2-azetidinone

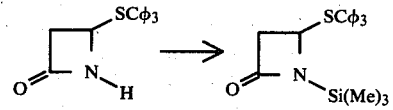

A solution of 4-tritylthio-2-azetidinone (345 mg, 1 mmole), 1,1,1,3,3,3,-hexamethyldisilazane (80 mg, 0.5 mmole) and chlorotrimethylsilane (55 mg, 0.5 mmole) in dichloromethane (20 ml) was heated under reflux for 18 h. Concentration of the reaction mixture left virtually pure title compound. δ(ppm, CDCl₃): 7.32 (15H, m, aromatics), 4.22 (1H, dd, H-4), 2.67 (1H, dd, J=4.1, J=16, H-3), 2.22 (1H, dd, J=2.2, J=16, H-3), 0.3 (9H, s, CH₃).

2. 1-(t-Butyldimethylsilyl)-4-tritylthio-2-azetidinone

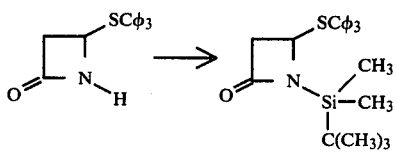

Triethylamine (1.62 ml, 11.6 mmoles) was added dropwise in 5 min to a cooled (0°) and stirred solution of 4-tritylthio-2-azetidinone (3.5 g, 10.1 mmoles) and chloro-t-butyldimethylsilane (1.68 g, 12.7 mmoles) in DMF (35 ml). The reaction mixture was stirred at room temperature for 18 h, diluted with water (250 ml) and ether (200 ml). The organic phase was washed with water (3×50 ml), dried and concentrated to leave an oil (4.33 g). Crystallization from pentane gave a total of 4.1 g(89%) of the title compound as a white solid, m.p. 113°-4°. δ(ppm, CDCl₃): 7.45 (15H, m, aromatics), 4.2

(1H, dd, H-4), 2.63 (1H, dd, J=4, J=16, H-3), 2.13 (1H, dd, J=2, J=16, H-3), 1.0 (9H, s, t-Bu), 0.35 (6H, s, Me). $\nu_{C=O}$ 1735 cm$^{-1}$. Anal. calc'd for $C_{28}H_{33}NOSSi$: C, 73.15; H, 7.24; N, 3.05; S, 6.97%. Found: C, 73.27; H, 7.32; N, 2.97; S 6.94%.

3. 1-Methoxymethyl-4-tritylthio-2-azetidinone

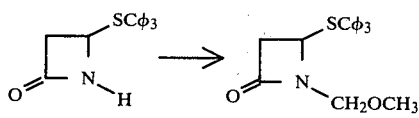

A solution of 4-tritylthio-2-azetidinone (1.38 g, 4.0 mmoles) in THF (10 ml) was added to a well stirred suspension of sodium hydride (200 mg of commercial 50%, 4.1 mmoles, washed with pentane) in THF (10 ml) maintained at −15°. Methanol (12 drops) was added and the mixture was stirred at −15° for 0.5 h. Methoxymethyl bromide (0.58 g, 4.6 mmoles) was added and the mixture was stirred for 2 h, diluted with ether, washed with water and brine, dried and concentrated to leave an oil (1.72 g). Crystallization from pentane gave a white solid (1.41 g) m.p. 72-76 δ(ppm, CDCl$_3$): 7.3 (15H, m, aromatics), 4.4 (3H, m, NCH$_2$O and H-4), 3.22 (3H, s, CH$_3$), 2.76 (2H, m, H-3).

4. 1-(Methoxyethoxymethyl)-4-tritylthio-2-azetidinone

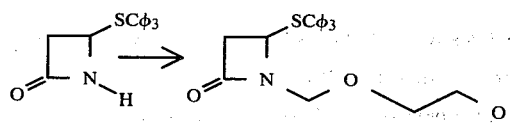

To a suspension of tetrabutylammonium bromide (322 mg, 1 mmole) and potassium hydroxide (85%, 70 mg, 1.1 mmole) in dichloromethane (10 ml) cooled to 5° was added with vigorous stirring 4-tritylthio-2-azetidinone (345 mg, 1 mmole) and methoxyethoxymethyl chloride (187 mg, 1.5 mmoles). The mixture was stirred at room temperature for 2 h, the solvent was evaporated and the residue partitioned between water and ethyl acetate. The dried organic phase was concentrated to leave a viscous oil (415 mg). Purification by column chromatography on silica gel eluting with ether (5%)-dichloromethane gave the title compound (206 mg, 48%) as an oil. δ(ppm, CDCl$_3$): 7.30 (15H, m, aromatics), 4.57 (2H, AB quartet, N—CH$_2$O), 4.46 (1H, dd, H-4), 3.50 (4H, s, OCH$_2$CH$_2$O), 3.30 (3H, s, CH$_3$), 2.75 (2H, m, H-3).

5. 1-(2′-Tetrahydropyranyl)-4-tritylthio-2-azetidinone

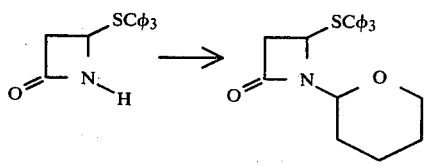

n-Butyl lithium (1.6 M, 1.6 ml, 2.56 mmoles) was added dropwise to a solution of 4-tritylthio-2-azetidinone (863 mg, 2.5 mmoles) in THF maintained at −78°. After stirring for 15 min, 2-chlorotetrahydropyran (560 mg, 4.7 mmoles) was added and the reaction mixture was allowed to come to room temperature in 1.5 h. The reaction solution was diluted with ethylacetate, washed with brine, dried and concentrated to leave an oil (635 mg). Column chromatography on silica gel eluting with dichloromethane-ether gave a mixture of the isomeric title compounds contaminated with a little starting material. δ(ppm, CDCl$_3$): 7.28 (15H, m, aromatics), 4.4 (H, dd, H-4), 2.9-2.2 (2H, m, H-3), 4.1-3.2 and 2.2-0.7 (tetrahydropyranyl).

6. Preparation of 4-Tritylthio-1-(p-nitrobenzyl-2′-triphenylphosphoranylidene-2′-acetate)-2-azetidinone

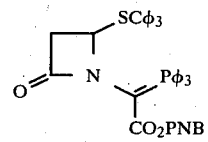

1-(1′-carboxy-1′-hydroxymethyl)-4-tritylthio-2-azetidinone triethylamine salt

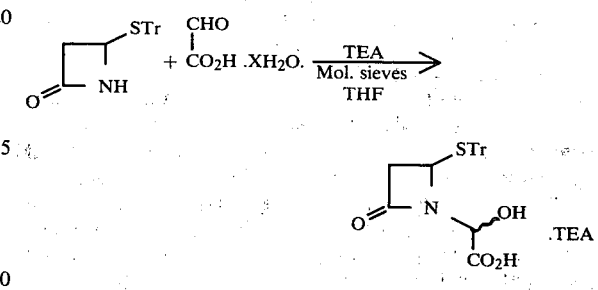

To a solution of 4-tritylthio-2-azetidinone (3.5 g, 10.15 mmol) in tetrahydrofuran (8 ml) was added triethylamine (1.42 ml, 10.15 mmol) and glyoxylic acid hydrate (1.02 g, 10.15 mmol). The mixture was stirred at room temperature with 4 Å mol. sieves* (volume of 8 ml) for 1 h and allowed to stand at room temperature overnight. The solidified mixture was diluted with methylene chloride and filtered; the filtrate was evaporated and the residue crystallized from pentane to give 5.18 g (98%) of title compound as a white solid mp 112°-5° C.; ir $\nu_{max}$: 3100-3600, and 1755 cm$^{-1}$; $^1$Hmr (CDCl$_3$)δ: 7.3 (15H, m), 4.92 and 5.10 (1H, 2s), 4.50 (1H, dd, J=8 Hz, J=3 Hz), 3.0 (1H, dd, J=15 Hz, J=7 Hz), 3.1 (6H, q, J=7 Hz), 2.70 (1H, dd, J=15 Hz, J=3 Hz), 2.0-3.5 (2H, m) and 1.21 ppm (9H, t, J=7 Hz).

*Mol sieves were dried at 150° C. for 18 h.

1-(1′-carboxy-1′-chloromethyl)-4-tritylthio-2-azetidinone

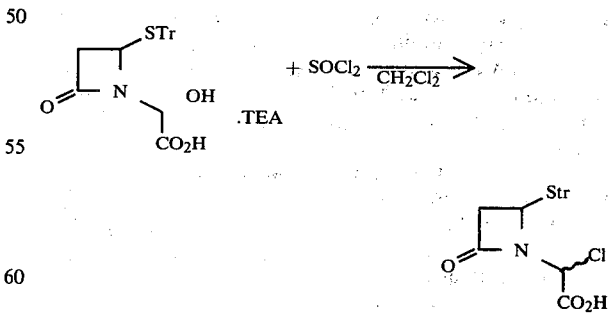

A cooled (ice bath) solution of the triethylamine salt of 1-(1′-carboxy-1′-hydroxymethyl)-4-tritylthio-2-azetidinone (1.04 g, 2.0 mmol) in methylene chloride (5 ml) was treated dropwise, under N$_2$, with thionyl chloride (0.16 ml, 2.2 mmol) in methylene chloride (2 ml). The solution was stirred at room temperature for 20 min and concentrated. The residue was diluted with benzene and filtered over a Celite/charcoal bed. The filtrate was evaporated in vacuo to give 870 mg (quantitative) of the title compound as an amorphous solid. It was used in the next step without further purification. ir $\nu_{max}$: 1775 cm$^{-1}$; $^1$Hmr (CDCl$_3$)δ: 9.22 (1H, bs), 7.27 (15H, m), 5.3 and 5.2 (1H, 2d, J=2 Hz), 4.6 (1H, m) and 2.8 ppm (2H, m).

1-(1'-carbo-p-nitrobenzyloxy-1'-chloromethyl)-4-tritylthio-2-azetidinone

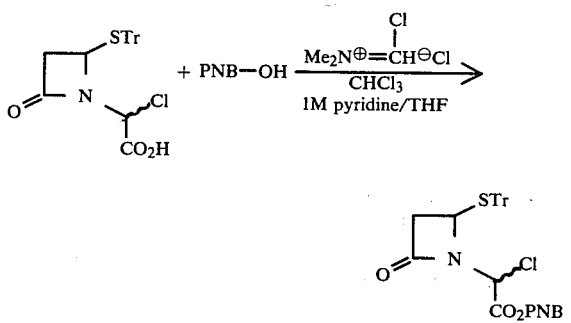

To a cooled (ice bath) solution of DMF (0.17 ml, 2.2 mmol) in *chloroform (4.4 ml) was added dropwise chloride (0.19 ml, 2.2 mmol). The mixture was stirred 5 min in ice, then 20 min at room temperature. The solution was cooled in an ice bath and treated dropwise with 1-(1'-carboxy-1'-chromethyl)-4-tritylthio-2-azetidinone (854 mg, 2 mmol) in chloroform (2 ml) followed by a 1 M solution of pyridine in tetrahydrofuran (2.2 ml, 2.2 mmol); the solution was stirred at room temperature for 30 min, cooled to 0° C. and treated dropwise with paranitrobenzyl alcohol (370 mg, 2.2 mmol) in tetrahydrofuran/chloroform (1:1, 2 ml) and triethylamine (0.31 ml, 2.2 mmol). The solution was stirred at room temperature for 30 min, then evaporated. The residue was diluted with benzene and filtered over a Celite/charcoal bed and the filtrate was evaporated in vacuo. The crude chloro ester was purified on a silica gel pad (5 g) and eluted with methylene chloride to give 790 mg (70%) of the title compound as a beige powder. Trituration in ether gave a white solid, mp 168°-9° C., ir $\nu_{max}$: 1780, 1760 cm$^{-1}$, $^1$Hmr (CDCl$_3$)δ: 8.15 (2H, d, J=9 Hz), 7.49 (2H, d, J=9 Hz), 7.3 (15H, m), 5.75 and 5.35 (1H, 2s), 5.3 (2H, s), 4.55 (1H, m), 2.8 (2H, m). This compound was identical to an authentic sample prepared by reaction of 4-tritylthio-2-azetidinone with p-nitrobenzyl glyoxylate followed by a thionyl chloride treatment.

*chloroform was left on mol sieves. (3 Å) for 18 h before reaction (to remove any trace of alcohol)

EXAMPLE 1

1-(p-Nitrobenzyloxycarbonylmethyltriphenylphosphoranyl)-4-(silver mercaptidyl)-2-azetidinone

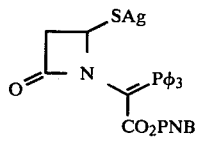

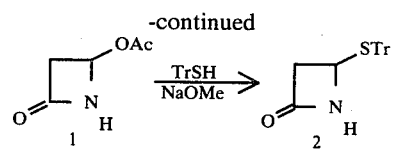

A methanol (90 cc) suspension of triphenylmethyl mercaptan (13.8 g., 0.05 mmole) was degassed for 0.5 hour with a nitrogen stream. The mixture was cooled down at 0° and sodium hydride (2.4 g, 0.05 mole, 50% oil dispersion) was added portionwise. The resulting solution was stirred for 5 min and 4-acetoxyazetidinone (7.7 g, 0.059 mole) in water (55 cc) was added rapidly. Precipitation of 4-triphenylmethyl mercaptoazetidinone (2) occurred immediately. The mixture was stirred for 4 h at room temperature. The solid was filtered off, washed with water and dissolved in methylene chloride. The methylene chloride solution was washed with diluted HCl, water, aqueous sodium bicarbonate water and brine and dried over MgSO$_4$ (89.8%, m.p.: 146.5°-147.5° C.)

Anal. Calc'd for C$_{22}$H$_{19}$NOS: C, 76.49; H, 5.54; N, 4.05; S, 9.28 Found: C, 7.54; H, 5.60; N, 4.00; S, 9.36.

δ(ppm, CDCl$_3$) 7.60-7.10 (15H, m, H-trityl), 4.62 (1H, bs, NH), 4.40 (1H, dd, J$_{4-3\ trans}$=3.0, J$_{4-3\ cis}$=5, H-4), 3.24 (1H, ddd, J$_{gem}$=15, J$_{3-4\ cis}$=5, J$_{3-NH}$=1.8, H-3), 2.81 (1H, ddd, J$_{gem}$=15, J$_{3-4\ trans}$=3.0, J$_{3-NH}$=1.2, H-3) $\nu_{c=o}$ (CHCl$_3$) 1760, $\nu_{NH}$ 3340.

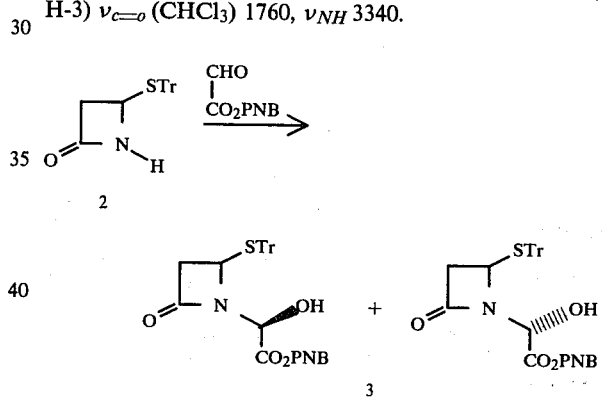

Hydrated p-nitrobenzyl glyoxylate (4.54 g, 0.02 mole) and azetidinone 2 (6.90, 0.02 mole) were refluxed in benzene through a Dean Stark condenser filled with 3 Å molecular sieves for 24 h. Further glyoxylate (2×454 mg, 2 mmoles) was added with reflux period (18 h) after each addition. The mixture was diluted with ether, washed with 5% aqueous HCl, water, aqueous 5% NaHCO$_3$ water and brine. It was dried over MgSO$_4$ (12 g, quantitative). A small fraction of the epimeric mixture was separated on a silica gel plate (CH$_2$Cl$_2$-ether 6:4)

Isomer A:

Rf=0.87, m.p.=170.5°-171.5° δ(ppm, CDCl$_3$) 8.07 (2H, d, J=9, Hm aromatic), 7.45 (part of d, Ho aromatic), 7.40-7.00 (15H, m, Trityl), 5.25 (2H, s, CH$_2$-PNB), 4.75 (1H, s, H—C—O), 4.37 (1H, dd, J$_{3-4\ trans}$=3, J$_{3-4\ cis}$=4, H-3), 2.83 (1H, dd, J$_{gem}$=16, J$_{4-3\ cis}$=4, H-4), 2.10 (1H, dd, J$_{gem}$=16, J$_{4-3\ trans}$=3, H-4), 1.42 (b.s., OH). $\nu_{c=o}$ (CHCl$_3$) 1770, 1760 (shoulder), $\nu_{NO2}$ 1525, $\nu_{OH}$ 3475.

Isomer B:

Rf=0.75, m.p.=152°-153° δ(ppm, CDCl$_3$), 8.13 (2H, d, J=9, Hm aromatic), 7.47 (2H, d, J=9, Ho aromatic), 7.40–7.00 (15H, m, trityl), 5.30 (3H, s, CH$_2$-PNB, H—C—O), 4.45 (1H, t, J=3.5, H-4), 2.90–2.70 (2H, AB part of ABX, H-4), 1.55 (b.s., OH). $\nu_{c=o}$ (CHCl$_3$) 1767, 1755 (shoulder), $\nu_{NO_2}$ 1525, $\nu_{OH}$ 3500.

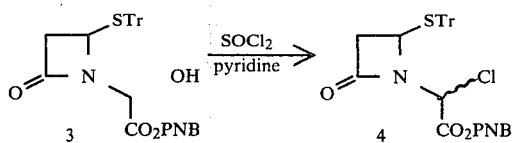

A cold (−15°) THF (150 cc, dried over molecular sieves) solution of azetidinone 3 (12 g, 21.7 mmoles) was treated with pyridine (1.9 g, 24.1 mmoles, 1.94 cc) and dropwise with thionyl chloride (2.86 g, 24 mmoles, 1.88 cc) under a nitrogen atmosphere. The mixture was stirred for 45 min at −15°. The precipitate was filtered off and washed with benzene. Evaporation of solvent gave a residue which was taken up in benzene and treated with activated charcoal (11.7 g, 94%, crystallized out from chloroform).

δ(ppm, CDCl$_3$) 8.17 (2H, d, J=8, Hm aromatic), 7.67–7.00 (17H, m, Ho aromatic, Tr-H), 5.80 (s, H—C—Cl), 5.37, 5.33 (2s, H—C—Cl, CH$_2$-PNB), 4.81 (1H, m, H-4), 3.27–2.40 (2H, m, H-3) $\nu_{c=o}$ (KBr film) 1785, 1770 $\nu_{NO_2}$ 1525.

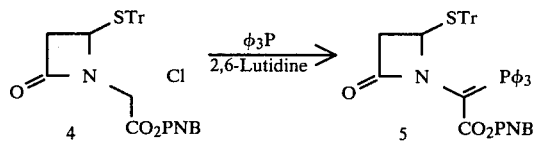

A THF (100 cc, distilled over LAH) solution of chloroazetidinone 4 (11.6 g, 20.2 mmoles) was treated with triphenyl phosphine (7.86 g, 30.0 mmoles) and 2,6-lutidine (2.36 g, 2.56 cc, 22.0 mmoles). The mixture was refluxed for 72 h. The precipitate was filtered off and washed with ether. The organic solution was washed with 2% aqueous HCl and 5% aqueous bicarbonate and dried over MgSO$_4$. Evaporation of solvent gave a residue which was purified through silica gel pad (200 g). The desired phosphorane was eluted with 30, 40 and 50% ether-benzene (11.4 g, 70.4%, m.p.: 201°–202°).

Anal. Calc'd for C$_{49}$H$_{40}$N$_2$O$_5$SP: C, 73.57; H, 5.04; N, 3.50; S, 4.01. Found: C, 73.58; H, 4.91; N, 3.44; S, 3.87. $\nu_{c=o}$ (CHCl$_3$) 1740, $\nu$ phosphorane (1620, 1610), $\nu_{NO_2}$ 1525.

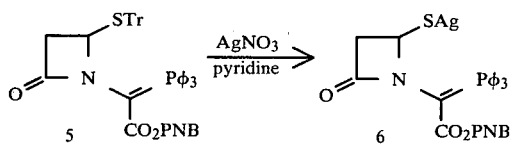

4-Tritylmercapto azetidinone 5 (1.6 g, 2 mmoles) was dissolved in CH$_2$Cl$_2$ (20 cc) and the solvent was flushed down at 55°–60°. Phosphorane 5 at 55°–60° was dissolved in preheated (55°–60°) methanol (32 cc). Immediately after the obtention of a methanolic solution of 6 it was treated with a preheated (55°–60°) mixture of methanolic 0.15 M silver nitrate solution (16 cc, 1.2 eq) and pyridine (174 mg, 178 μl, 2.2 mmoles, 1.1 eq). The warming bath was then immediately removed. The mixture was stirred at room temperature for 2 h and at 0° C. for 1 h. The silver mercaptide 6 was filtered off, washed twice with cold (0°) methanol and three times with ether. (1.12 g, 84.5%, m.p.: 130–135 dec.).

$\nu_{c=o}$ (CHCl$_3$) 1795, 1725 (shoulder), $\nu$ phosphorane (1620, 1605), $\nu_{NO_2}$ 1530.

EXAMPLE 2

1-(p-Nitrobenzyloxycarbonylmethyltriphenylphosphoranyl)-4-(silver mercaptidyl)-2-azetidinone

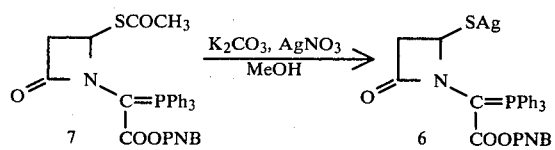

A solution of phosphorane 7 (1.796 g, 3.0 mmoles) in chloroform (3 ml) was diluted with methanol (90 ml), cooled at 0° C. under nitrogen atmosphere and treated successively with silver nitrate (0.51 g, 3.0 mmoles) and potassium carbonate (0.33 g, 2.4 mmoles). The reaction mixture (protected from light) was stirred at 0° C. for 15 min., then the cooling bath was removed and stirring was continued for 3 h. The reaction mixture was cooled down to −10° C., stirred for 1 h and filtered; the silver mercaptide was successively washed with cold methanol and ether; 1.91 g. M.P.: 138°–145° C. dec, 96%. I.R. (nujol) cm$^{-1}$: 1748, 1620 and 1605. An analytical sample was obtained by preparative TLC (ethyl acetate); M.P.: 140°–5° C. dec, calc'd for C$_{30}$H$_{24}$N$_2$O$_5$SPAg: C, 54.31; H, 3.65; N, 4.22; S, 4.83. Found: C, 54.11; H, 3.48; N, 3.92; S, 4.62.

EXAMPLE 3

1-(p-Nitrobenzyloxycarbonylmethyltriphenylphosphoranyl)-4-(silver mercaptidyl)-2-azetidinone A. Use of aniline as base

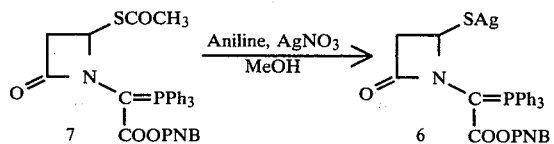

A solution of phosphorane 7 (1.8 g, 3.0 mmoles) in chloroform (4 ml) was diluted with methanol (90 ml), cooled to −15° C. under nitrogen atmosphere and treated successively with silver nitrate (0.56 g, 3.3 mmoles) and aniline (1.5 ml, 16.5 mmoles). The reaction mixture (protected from light) was stirred at −15° C. for 0.5 h and then the cooling bath was removed and stirring was continued for 24 h. The reaction mixture was cooled to −10° C. and stirred for 1 h before being filtered; the silver mercaptide was successively washed with cold methanol and ether; 1.55 g, M.P. 114°–5° C. dec. 77.9%. IR (nujol) cm$^{-1}$; identical to compound of Example 2.

Silver 1-(paranitrobenzyl 2′-triphenylphosphoranylidene-2′-acetate)-2-azetidinone-4-thiolate B. Use of 4-dimethylaminopyridine (DMAP) as base

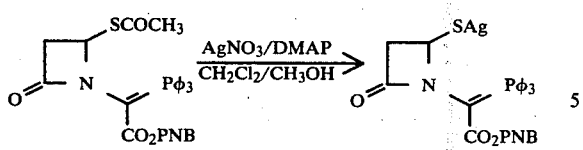

A solution of the above S-acetyl phosphorane (17.96 g, 30 mmol) in methanol and dichloromethane (1:2, 450 ml) was purged with nitrogen (5-10 min), cooled to 5° C. and treated successively with silver nitrate (5.35 g, 31.5 mmol) and 4-dimethylaminopyridine (3.85 g, 31.5 mmol). The ice-bath was removed and the solution refluxed vigorously for 2 h and then stirred at room temperature for 1 h. The colored reaction mixture was treated with charcoal, filtered and evaporated. The residue was redissolved in the minimum amount of dichloromethane and added dropwise, with stirring to cold methanol (300 ml). The precipitated silver salt was collected by filtration, washed with ether and dried; 18.1 g (91%); ir (CHCl$_3$) $\nu_{max}$: 1745 (C=O of $\beta$-lactam) and 1607 cm$^{-1}$ (C=O of ester).

Silver-1-(paranitrobenzyl 2'-triphenylphosphoranylidene-2"-acetate)-2-azetidinone-4-thiolate C. Use of diazabicycloundecene (DBU) as base

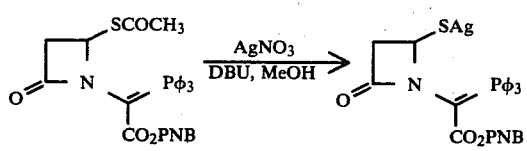

The above S-acetylphosphorane (36.0 g, 0.060 mol) was dissolved in methylene chloride 120 ml. The solvent was evaporated in order to obtain an oil. The resulting oily residue was dissolved in warm (35° C.) methanol (240 ml) and treated rapidly with a methanolic (420 ml) solution of silver nitrate (10.68 g, 0.0628 mol). The resulting solution (or suspension) was stirred at room temperature for 5 min, cooled down (ice bath) and a DBU (8.96 ml, 0.060 mol) solution in methanol (20 ml) was added over a 5 min period. The mixture was stirred for 5 min. The solid was filtered, washed once with cold (0° C.) methanol and ether and dried under vacuum; 37.0 g (93%); ir (nujol mull) $\nu_{max}$ 1745 (c=O) and 1600 cm$^{-1}$ (phosphorane)

D. Use of pyrrolidine as base Silver 1-(paranitrobenzyl 2'-triphenylphosphoranylidene-2"-acetate)-2-azetidinone-4-thiolate

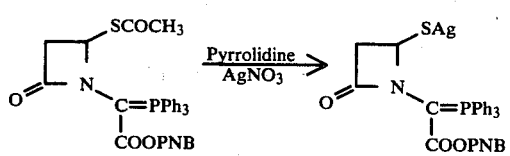

To a cold (0° C.) solution of 4-acetylthio-1-(paranitrobenzyl 2"-triphenylphosphoranylidene-2"-acetate)-2-azetidinone (0.60 g, 1.0 mmol) in CH$_2$Cl$_2$ (2 ml) was added MeOH (4 ml), a solution of AgNO$_3$ in MeOH (0.14 N, 7.86 ml, 1.1 mmol) and a solution of pyrrolidine (0.92 ml, 1.1 mmol) in MeOH (2 ml). The cooling bath was removed and the reaction mixture was stirred for 1.75 h, cooled to −10° C., stirred for 0.25 h and filtered. The solid was washed with cold MeOH and dried in vacuo; 0.548 g, m.p. 115° C., 82.4%. ir (nujol) $\nu_{max}$: 1755 (C=O) and 1600 cm$^{-1}$ (aromatics).

EXAMPLE 4

Mercuric (II)-[2'-Triphenylphosphoranylidene-2'-acetate]-2-azetidinone-4-thiolate

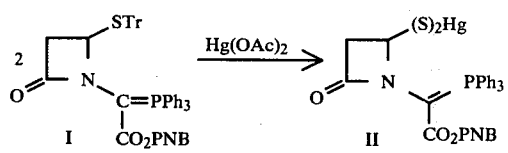

A solution of I (2.4 g, 3 mmoles) in dichloromethane (15 ml) was cooled to 5° C. and treated with a solution of mercuric acetate (0.525 g, 1.65 mmole) dissolved in methanol (15 ml). After stirring at 5° C. for 2 h, the solvent was evaporated and the residue redissolved in dichloromethane and washed with cold water. The organic solution after being dried (MgSO$_4$) and treated with charcoal, was evaporated to give a foam which crystallized when triturated in ether. Yield: 1.73 g (91%) M.P. 123°-127° C., I.R. (CHCl$_3$) 1745 cm$^{-1}$ ($\nu_{c=o}$ $\beta$-lactam) 1608 cm$^{-1}$ (phenyl)

EXAMPLE 5

A. Preparation of 3-(1'-Hydroxy-1'-ethyl)-1-methoxymethyl-4-tritylthio-2-azetidinones

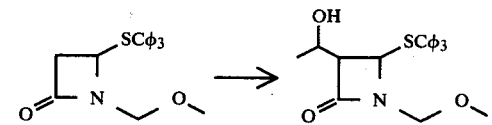

(a) (1'S,3S,4R and 1'R,3R,4S)isomer (isomer C)

A solution of lithium diisopropyl amide was prepared in THF (5 ml) at −78° C. from n-butyl lithium (1.6 M, 1.0 ml, 1.6 mmol) and diisopropylamine (0.25 ml, 1.84 mmol). After 30 min a solution of 1-methoxymethyl-4-tritylthio-2-azetidinone (491 mg, 1.42 mmol) in THF (6 ml) was added dropwise and the solution was stirred for 15 min. Acetaldehyde (3.0 ml) was added dropwise, followed, after 20 min, by water (30 ml). The mixture was acidified to pH 3 with 2% HCl and extracted with ethyl acetate (5×20 ml). The combined organic phases were washed with brine, dried and concentrated to leave an oil which crystallized upon trituration with ether: 440 mg, 80%, mp 188.5°-9° C.; $^1$Hmr (CDCl$_3$) $\delta$: 7.3-(15H, m, aromatics), 4.37 (2H, ABq, N—CH$_2$O), 4.32 (1H, d, J=2, H-4), 3.17 (3H, s, OCH$_3$), 3.32-2.70 (2H, m, H-3 and H-5), and 1.12 ppm (3H, d, J=7, CH$_3$); Anal. calcd for C$_{26}$H$_{27}$NO$_3$S: C 72.02; H 6.28, N 3.23, S 7.39; found: C 71.99, H 6.02, N 3.21, S 7.40%.

(b) (1'S,3S,4R and 1'R,3R,4S) and (1'R,3S,4R and 1'S,3R,4S) (isomers C and B).

A solution of lithium diisopropyl amide (0.482 mmol) is prepared at −78° C. in dry ether (3 ml) from butyl lithium 0.191 ml of 2.52 M solution in hexane, 0.482 mmol) and diisopropyl amine (0.067 ml, 0.482 mmol). After 20 min, a solution of (4R and 4S) 1-methoxymethyl-4-tritylthio-2-azetidinone (0.171 g, 0.439 mmol) in a mixture of dry ether (1 ml) and dry THF (1 ml) was added dropwise and the resulting clear solution was stirred at −78° C. for 15 min. A solution of tetrabutyl ammonium fluoride (0.96 ml of a 0.5 M solution in THF, 0.48 mmol) was then added. A precipitate was formed with the generation of a slight pink colour. After 5 min at −78° C., the reaction mixture was quenched with freshly distilled acetaldehyde (0.2 ml, excess), and the stirring continued for 15 more min. The work-up was done by adding to a saturated solution of ammonium chloride and extracting with ethyl acetate (2×25 ml). The combined organic phases were washed with brine and dried over anhydrous magnesium sulfate. Evaporation of the solvent under vacuum gave an oil (0.228 g) which was chromatographed on 10 g of silica gel A mixture of benzene and ethyl acetate (6:4) gave 0.106 g (62% recovery) of substrate and a mixture of the two isomer alcohols which were separated by chromatography on thick layer plates (same solvent-system). The alcohol with the high Rf (0.033 g, 17%) was identical to the above isomer (isomer C): mp 188.5°–189° C. (Ether-dichloromethane); The alcohol with low Rf (0.030 g, 16%) (isomer B), was obtained as an oil which crystallized with difficulty from hexanes: mp 94°–95° C. ir (CH$_2$Cl$_2$) $\nu_{max}$: 3600 (OH), 1760 cm$^{-1}$ (C=O); $^1$Hmr (CDCl$_3$) δ: 6.9–7.5 (15H, m, aromatics), 4.2 (2H, center of ABq, J=11.5, CH$_2$—O—CH$_3$), 4.28 (1H, d, J=2.0, 4-H), 3.65 (1H, center of a broad sextet, H-1'), 3.3 (1H, dd, J$_{3,4\ trans}$=2.5, J$_{3,1'}$=5.5, H$_3$), 3.15 (3H, s, O—CH$_3$), 1.55 (1H, broad s, OH-1'), 1.05 (3H, d, J=6.5, H-2'); Anal. calcd for C$_{26}$H$_{27}$NO$_3$S: C 72.02, H 6.28, N 3.23, S 7.39; found: C 71.77, H 6.36, N 3.15, S 7.43%.

B. Preparation of trans 3-Acetyl-1-methoxymethyl-4-tritylthio-2-azetidinone

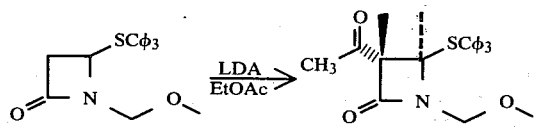

Lithium diisopropylamide was prepared under a nitrogen atmosphere at −78° C. in the usual manner from diisopropylamine (0.34 ml, 2.4 mmol) and n-butyl lithium (1.1 ml of a 2.2 M solution in hexane, 2.4 mmol) in THF (3 ml). A solution of 1-methoxymethyl-4-tritylthio-2-azetidinone (0.78 g, 2 mmol) in THF (3 ml) was added dropwise and, after stirring at −78° C. for 20 min, ethylacetate (0.53 g, 6 mmol) was added in one portion and stirring continued for 0.75 h at −78° C. The reaction mixture was diluted with ether and washed with an ammonium chloride solution, water and brine, dried and concentrated to give an oil (0.7 g). Purification was achieved by chromatography over silica gel (20 g) eluting with increasing amounts of ether in benzene. The pertinent fractions were concentrated to give the title material as a colorless oil (0.32 g, 37%); $^1$Hmr (CDCl$_3$) δ: 7.7–6.8 (15H, aromatics), 4.85 (1H, d, J=2, H-4), 4.5 (2H, s, N—CH$_2$—O), 3.9 (1H, d, J=2, H-3), 3.22 (3H, s, CH$_3$) and 2.0 ppm (3H, s, CH$_3$); ir $\nu_{max}$: 1770, 1710 cm$^{-1}$.

C. Preparation of trans 3-Acetyl-1-(t-butyldimethylsilyl)-4-tritylthio-2-azetidinone

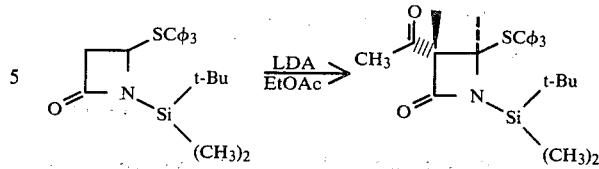

Diisopropyl lithium amide was prepared in the usual manner from diisopropylamine (0.18 ml, 1.24 mmol) and n-butyllithium (0.78 ml of a 1.6 M solution in hexane, 1.24 mmol) in THF (8 ml). A solution of 1-(t-butyldimethylsilyl)-4-tritylthio-2-azetidinone (0.46 g, 1 mmol) in THF (8 ml) was added dropwise at −78° C. After a 5 min stirring period, ethyl acetate (1 ml) was added in one portion and the mixture was stirred 3 h at −78° C. The mixture was acidified with cold hydrochloric acid (0.5 N) to pH 6 and extracted with ethyl acetate (2×20 ml). The combined organic phases were dried and concentrated to give an oil (0.5 g) which crystallized from pentane: 200 mg total, 40%; mp 122°–4° C.; ir $\nu_{max}$: 1750, 1710 cm$^{-1}$; $^1$Hmr (CDCl$_3$) δ: 8–7.1 (15H, m, aromatics), 4.83 (1H, d, J=2, H-4), 3.38 (1H, d, J=2, H=3), 1.80 (3H, s, CH$_3$), 0.92 (9H, s, Bu and 0.3 ppm (6H, s, CH$_3$).

D. Preparation of trans-1-(t-Butyldimethylsilyl)-3-formyl-4-tritylthio-2-azetidinone

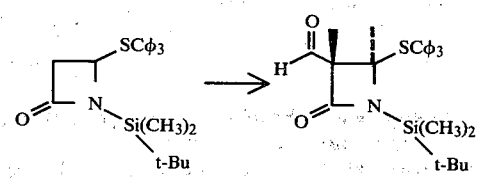

To a cooled (−78° C.) solution of diisopropylamine (0.34 ml, 2.4 mmol) in tetrahydrofuran (5 ml) was added dropwise, under N$_2$, a solution of 1.5 M n-BuLi (1.6 ml, 2.4 mmol). After stirring for 30 min, a solution of 1-(t-butyldimethylsilyl)-4-tritylthio-2-azetidinone (1.0 g, 2.18 mmol) in tetrahydrofuran (5 ml) was added dropwise and stirring was maintained for 30 min. Ethyl formate (0.8 ml, 9.9 mmol) was added and the cooled solution was stirred for 10 min. The reaction mixture was washed successively with cold 1 N hydrochloric acid (5 ml), 1 M sodium bicarbonate (6 ml), water (10 ml) and brine. The organic layer was dried (MgSO$_4$), evaporated and crystallized from pentane to give 810 mg (76%) of formate as a white solid mp 132°–3° C.; ir (CHCl$_3$) $\nu_{max}$: 1760, 1715 cm$^{-1}$; $^1$Hmr (CDCl$_3$) δ: 9.0 (1H, d, J=1.25 Hz), 7.30 (15H, m), 4.7 (1H, d, J=1.5 Hz) and 3.5 ppm (1H, t, J=1.5 Hz).

NOTE:
(a) diisopropyl amine was distilled over CaH and stored on KOH
(b) tetrahydrofuran was distilled over L.A.H. and stored on molecular sieves 3 A
(c) ethyl formate was stirred at room temperature with K$_2$CO$_3$, then distilled over P$_2$O$_5$
(d) n-BuLi was titrated with 1 N hydrochloric acid E. Preparation of 1-(t-Butyldimethylsilyl)-3-(1'-hydroxy-1'-ethyl)-4-tritylthio-2-azetidinones. (4 isomers).

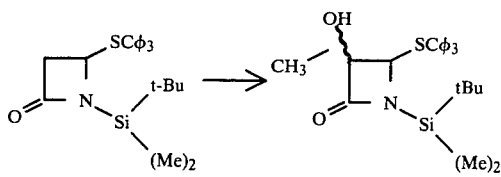

n-Butyllithium (1.6 M, 3.4 ml, 5.44 mmol) was added in 5 min to a solution of diisopropylamine (0.847 ml, 6.23 mmol) in THF (30 ml) maintained at −78° C. After 0.5 h a solution of 1-(t-butyldimethylsilyl)4-tritylthio-2-azetidinone (2.0 g, 4.4 mmol) in THF (20 ml) was added; after 15 min acetaldehyde (10 ml) was added in one portion; after another 15 min water (100 ml) was added. The mixture was acidified (pH 5-6) with dilute hydrochloric acid and extracted with ethyl acetate (3×30 ml). The organic phases were washed with brine, dried and concentrated to leave an oil which was found to consist of a mixture of four isomers by tlc (labelled isomers A,B,C,D by decreasing order of polarity).

Crystallization of the oily residue in ethyl acetate-pentane gave isomers B and C as a white solid and left A and D in the mother-liquors. The four pure compounds were obtained by preparative chromatography (Waters, 500) of the above solid and mother-liquors. The relative properties were: A, 17%; B, 32%; C, 39%; D, 12%. In the above reaction, when ether was substituted for THF and the reaction quenched after 1 min at −78° C., the relative proportions of A,B,C, and D were: 12.9, 30.5, 38.2 and 18.4%. In ether, when the reaction was allowed to come to 20° C. in 2 h before quenching, the proportions were: 13.4, 24.6, 44, and 18%. When one molar equivalent of anhydrous magnesium bromide was added to the reaction mixture, the proportions changed to: 19.2, 19.7, 30.1 and 31%.

Isomer A: This isomer possesses a cis-stereochemistry at $C_3$-$C_4$. It is a racemic mixture composed of the 1'S, 3R, 4R) and the 1'R, 3S, 4S) enantiomers. Compounds later derived from compound A are referred to as "Isomer A". They consist of an enantiomeric mixture and possess the same configuration at $C_{1'}$, $C_3$ and $C_4$. Compounds derived from compound A, through a reaction that proceeds with inversion of configuration, will be referred to as "Isomer D" if the inversion takes place at $C_1$, and as "isomer C" for the inversion, at $C_3$ mp 152°-3° C.; $^1$Hmr (CDCl$_3$) δ: 8.0-6.8 (15H, m, aromatics), 4.30 (1H, d, J=5.5, H-4), 3.78 (1H, m, H-1'), 3.10 (1H, dd, J=5.5, J=10, H-3), 1.22 (3H, d, J=6.5, CH$_3$), 0.95 (9H, s, Bu), 0.27 (6H, 2s, CH$_3$). Anal. calcd for: C$_{30}$H$_{37}$NO$_2$Si: C 71.52, H 7.40, N 2.78, S 6.36%. found: C 71.28, H 7.41, N 2.48, S 6.19%.

Isomer B: This isomer possesses a trans-stereochemistry at $C_3$-$C_4$. It is a racemic mixture composed of the (1'R,3S,4R) and the (1'S,3R,4S) enantiomers. Compounds with the same configuration at $C_{1'}$, $C_3$ and $C_4$ are referred to as "Isomer B"; ir (CHCl$_3$) $\nu_{max}$: 1745 cm$^{-1}$ (C=O); mp 158°-9° C.; $^1$Hmr (CDCl$_3$) δ: 7.60-7.10 (15H, m, aromatics), 4.02 (1H, d, J=0.8 H-4), 3.32 (1H, dd, J=3.0, J=0.8, H-3), 3.55-3.15 (1H, m, H-1'), 0.88 (12H, CH$_3$, and t-Bu), 0.16 (6H, s, CH$_3$);

Isomer C: This isomer possesses a trans-stereochemistry at $C_3$-$C_4$. It is a racemate formed of the (1'S,3S,4R) and the (1'R,3R,4S) enantiomers. Compounds with the same configuration at $C_{1'}$, $C_3$ and $C_4$ are referred to as "Isomer C". mp 134°-6° C.; $^1$Hmr (CDCl$_3$) δ: 7.60-7.10 (15H, m, aromatics), 4.32 (1H, d, J=1.8, H-4), 3.02 (1H, dd, J=2.7, J=1.8, H-3), 3.0-2.5 (1H, dq, J=2.7, J=6, H-1'), 1.02 (3H, d, J=6, CH$_3$), 0.95 (9H, s, t-Bu), 0.27 (6H, s, CH$_3$); ir (CHCl$_3$) $\nu_{max}$: 1735 cm$^{-1}$ (C=O).

Isomer D: This isomer possesses a cis-stereochemistry at $C_3$-$C_4$. It is a racemate composed of the (1'R,3R,4R) and the (1'S,3S,4S) enantiomers. Compounds with the same configuration at $C_{1'}$, $C_3$ and $C_4$ are referred to as "Isomer D". mp 171°-2° C.; Hmr (CDCl$_3$): 7.80-6.90 (15H, m, aromatics), 4.70 (1H, d, J=4.5, H-4), 3.02 (1H, dd, J=4.5, J=0.5, H-3), 2.39 (1H, dq, J=0.5, J=6.5, H-1'), 1.0 (3H, d, J=6.5, CH$_3$), 0.97 (9H, s, t-Bu), 0.32 (6H, s, CH$_3$). Anal. calcd for C$_{30}$H$_{37}$NO$_2$SSi: C 71.52, H 7.40, N 2.78, S 6.36%. found: C 71.27, H 7.43, N 2.51, S 6.31%.

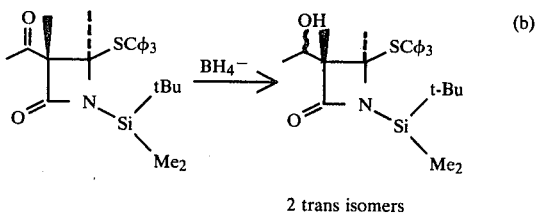

2 trans isomers

A solution of trans 3-acetyl-1-(t-butyldimethylsilyl)-4-tritylthio-2-azetidinone (1.0 g, 2 mmol) in THF (30 ml) was added dropwise, under a nitrogen atmosphere, to a cooled (0°) and stirred suspension of sodium borohydride (0.38 g, 10 mmol) in THF (120 ml). The ice bath was removed and the mixture was stirred at room temperature for 4 h. It was poured into ice-cold hydrochloric acid (1N, pH 6), stirred for 15 min and extracted with ether (3X). The combined ether extracts were dried and concentrated to give an oil (1.04 g) which was crystallized in pentane to give the title compounds as a 70:30 mixture of the C and B isomers. mp 119°-121° C.; 84%.

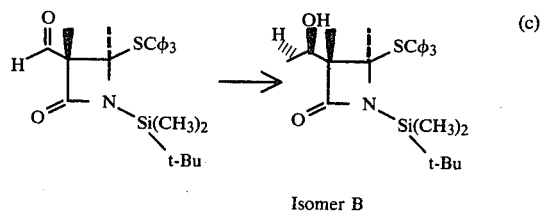

Isomer B

A suspension of cuprous iodide (4.78 g, 15 mmol) in ether (50 ml) was cooled to 0° C. and treated under N$_2$, with a 1.9 M solution of methyl lithium (26 ml, 50 mmol). The brown solution was stirred at 0° C. for 10 min and then cooled to −60° C. and treated dropwise with the trans 1-1(t-butyl dimethylsilyl)-3-formyl-4-tritylthio-2-azetidinone (2.43 g, 5.0 mmol) in a mixture of tetrahydrofuran (10 ml)/ether (40 ml). Stirring was continued for 3 h. The solution was warmed up to −40° C. and treated carefully with a 1 M solution of ammonium chloride. The mixture was filtered over Celite and the organic phase was washed with a 1 M solution of ammonium chloride (3×5 ml) and then brine and dried over sodium sulfate. Filtration and evaporation gave alcohol, isomer B, which crystallized from warm pentane to yield 1.6 g (65%), mp 160°-1° C.; ir (CHCl$_3$) $\nu_{max}$: 1730 cm$^{-1}$;. $^1$Hmr (CDCl$_3$) δ: 7.32 (15H, m), 4.05 (1H, s), 3.4 (1H, d, J=3HZ, 3.25-3.55 (1H, m), 1.6 (1H, s), 0.9 (12H, s) and 0.1 ppm (6H, s).

NOTE:

(a) tetrahydrofuran and ether were distilled over L.A.H.

(b) methyl lithium was titrated with 1 N hydrochloric acid (c) copper (I) iodide was purified by continuous extraction with anhydrous tetrahydrofuran in a Soxhlet extractor for 18 h, then dried under vacuum in a dessicator ($P_2O_5$) for 18 h.

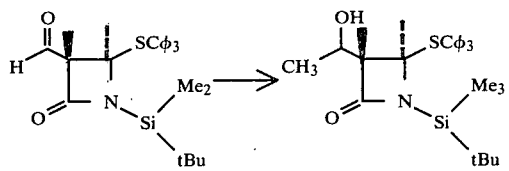   (d)

Methylmagnesium iodide (0.1 ml, 0.1 mmol) was added dropwise to a cooled (0° C.) and stirred solution of trans 1-(t-butyldimethylsilyl)-3-formyl-4-tritylthio-2-azetidinone (25 mg, 0.05 mmol) in THF (2 ml). The solution was stirred 1.5 h at 0° C., poured onto an ammonium chloride solution, acidified with a hydrochloric acid solution (1 N) and extracted with ether. Drying and concentration of the organic extracts left an oil consisting of starting material and a small amount of a mixture of the two trans title compounds with isomer B predominating.

F. Preparation of (1'S,3S,4R and 1'R,3R,4S) 1-(t-Butyldimethylsilyl)-3-(1'-trimethylsilyloxy-1'-ethyl)-4-tritylthio-2-azetidinone (isomer C)

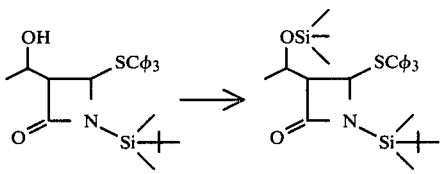

A solution of (1'S,3S,4R and 1'R,3R,4S) 1-(t-butyldimethylsilyl)-3-(1'-hydroxy-1'-ethyl)-4-tritylthio-2-azetidinone (15 mg, 0.3 mmol) and azidotrimethylsilane (35 mg, 0.30 mmol) in dry THF (6 ml) was stirred at room temperature until disappearance of the starting material (15 min). Purification of the reaction mixture by column chromatography (silica gel, $CH_2Cl_2$) gave the desired compound as a white solid (128 mg, 74%) mp 144°–146° C. $^1$Hmr (CDCl$_3$) δ: 7.10–7.60 (15H, m, aromatics), 4.30 (1H, d, J=1.5, H-4), 2.25–2.89 (2H, m, H-3, H-1'), 0.82–1.07 (12H, m, t-Bu, H-2'), 0.27 (6H, s, CH$_3$), −0.10 (9H, s, —O—Si(CH$_3$)$_3$; ir (CHCl$_3$) $\nu_{max}$: 1736 cm$^{-1}$ (C=O).

G. Preparation of (1'S,3R,4R and 1'R,3S,4S) 1'(t-Butyldimethylsilyl)-3-(1'-methoxymethoxy ether-1'-ethyl)-4-tritylthio-2-azetidinone (isomer A).

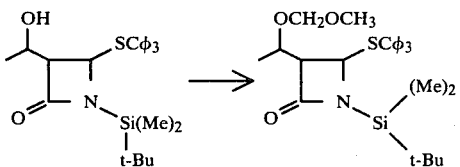

n-Butyllithium (ca 12.5 ml of 1.6 M solution in hexane, 20 mmol; just enough to obtain a permanent pink coloration) was added dropwise to a solution of (1'S,3R,4R and 1'R,3S,4S) 1-(t-Butyldimethylsilyl)-3-(1'-hydroxy-1'-ethyl)-4-tritylthio-2-azetidinone (isomer A) (10.1 g, 20 mmol) in THF (100 ml) maintained at −78°. After a 15 min stirring period a solution of bromomethoxymethyl ether (2 ml, 24 mmol) in THF (30 ml) was added dropwise. The mixture was stirred at 1 hr at −78° and 2 h at room temperature and poured into an ammonium chloride solution (200 ml). Extraction with ethyl acetate (3×200 ml), washing with brine, drying with sodium sulfate and concentration gave the crude title compound which was purified by chromatography on silica gel eluting with increasing amounts of ether in benzene (10.4 g 95%). $^1$Hmr (CDCl$_3$) δ: 7.1–7.5 (15H, m, aromatics), 4.47 (1H, d, H-4), 4.23 (2H, Abq, J=7, O—CH$_2$—O), 3.1–3.4 (2H m, H-3 et H-1'), 3.23 (3H, s, O—CH$_3$), 1.37 (3H, d, J=6.5, CH$_3$), 0.97 (9H, s, Bu) and 0.25 ppm (6H, 2s, CH$_3$).

H. Preparation of (1'S,3S,4R and 1'R,3R,4S) 1-(t-Butyldimethylsilyl)-3-(1'-formyloxy-1'-ethyl)-4-tritylthio-2-azetidinone (isomer C)

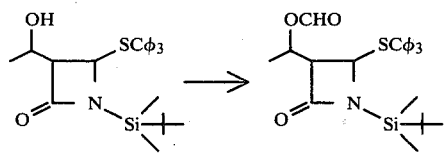

A solution of (1'S,3S,4R and 1'R,3R,4S) 1-(t-butyldimethylsilyl)-3-(1'-hydroxy-1'-ethyl)-4-tritylthio-2-azetidinone (isomer c) (50 mg, 0.1 mmol), p-bromobenzenesulfonylchloride (100 mg, 0.4 mmol) and dimethylaminopyridine (24 mg, 0.2 mmol) in DMF (3 ml) was stirred at room temperature until disappearance of starting material (0.5 h). Then the reaction mixture was diluted with water and extracted with ether. The organic extracts were washed with brine, dried (MgSO$_4$) and evaporated. The title compound was purified by column chromatography. $^1$Hmr (CDCl$_3$) δ: 7.80 (1H, s, CHO), 7.20–7.66 (15H, m, aromatics), 3.90–4.36 (1H, m, H-1'), 4.07 (1H, d, J=2, H-4), 3.22 (1H, broad s, H-3), 1.18 (3H, d, J=6.5, H-2'), 1.0 (9H, s, t-Bu), 0.31 (6H, s, di—CH$_3$).

I. Preparation of (1'R,3S,4R and 1'S,3R,4S) 1'(t-Butyldimethylsilyl)-3-1'-acetoxy-1'-ethyl)-4-tritylthio-2-azetidinone (Isomer B)

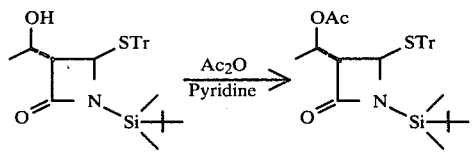

A solution of (1'R,3S,4S and 1'S 3R 4S) 1-(t-butyldimethylsilyl)-3-(1'-hydroxy-1'-ethyl)-4-tritylthio-2-azetidinone (13.85 g, 27.5 mmol) in pyridine (75 ml) acetic anhydride (50 ml) (prepared at 0°) was stirred at room temperature for 40 h. The reagents were evaporated off (the last traces being removed azeotropically with toluene 3 times) leaving a nearly white solid. Crude derivative was crystallized from an ether-petroleum ether mixture to give pure title compound (97.5%). $^1$Hmr (CDCl$_3$ δ: 7.64–7.03 (15H, m, H aromatic), 4.60 (1H, m, J=6, H-1'), 3.92 (1H, d, J=2, H-4), 3.55 (1H, dd, J=2, J=6, H-3), 1.79 (3H, s, CH$_3$CO), 0.98 (3H, d, J=6, CH₃), 0.88 (9H, s, t-butyl), 0.12 (6H, s, CH₃); ir (CHCl₃) $\nu_{max}$: 1775, 1740 cm⁻¹ (C=O)

J. Preparation of 1-(t-Butyldiethylsilyl)-3-(1'-paranitrobenzyldioxycarbonyl)-1'-ethyl)-4-tritylthio-2-azetidinone. (4 isomers)

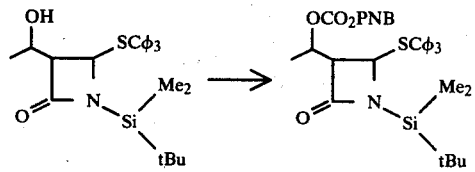

"Isomer C" n-Butyllithium (8.8 ml of 1.6 M solution in hexane, 14 mmol; just enough to obtain a permanent pink coloration) was added dropwise to a solution of "Isomer C" of 1-(t-butyldimethylsilyl)-3-(1'-hydroxy-1'-ethyl)-4-tritylthio-2-azetidinone (6.55 g, 13 mmol) in THF (70 ml) maintained at −78° C. After a 15 min stirring period a solution of paranitrobenzyl chloroformate (3.2 g, 14.8 mmol) in THF (30 ml) was added dropwise. The mixture was stirred 1 h at −78° C. and poured into an ammonium chloride solution (100 ml). Extraction with ethyl acetate (3×100 ml) washing with brine, drying and concentration left 11 g of crude material. The pure title compound was obtained by chromatography on silica gel (220 g) eluting with increasing amounts of ether in benzene. 93%, mp 118°–9° C. (ether); ¹Hmr (CDCl₃) δ: 8.35–7 (19H, m, aromatics), 5.12 (2H, s, benzyl), 4.08 (1H, d, J=1.8, H-4), 4–3.5 (1H, dq, J=6.5, J=2, H-1'), 3.10 (1H, dd, J=2, J=1.8, H-3), 1.2 (3H, d, J=6.5, CH₃), 1.0 (9H, s, Bu) and 0.30 ppm (6H, 2s, CH₃); ir (CHCl₃) $\nu_{max}$: 1745 cm⁻¹ (C=O); Anal. calcd for C₃₈H₄₂N₂O₆SiS: C 66.83, H 6.20, N 4.10, S 4.69; found: C 66.90, H, 6.26, N 4.11, S 4.59.

"Isomer B" The "Isomer B" of 1-(t-butyldimethylsilyl)-3-(1'-hydroxy-1'-ethyl(-4-tritylthio-2-azetidinone, treated as described above gave pure "Isomer B" of 1-(t-butyldimethylsilyl)-3-(1'-paranitrobenzyldioxycarbonyl-1'-ethyl)-4-tritylthio-2-azetidinone as a foam, 95%. ¹Hmr (CDCl₃) δ: 8.32–6.90 (19H, m, aromatics), 5.1 (2H, s, benzyl), 4.65–4.20 (1H, m, H-1'), 3.97 (1H, d, J=1.5, H-4), 3.58 (1H, dd, J=1.5, J=5.8, H-3), 1.1 (3H, d, CH₃), 0.7 (9H, s, Bu and 0.2 ppm (6H, s, CH₃); ir (film) $\nu_{max}$: 1755, 1740 cm⁻¹ C=O.

"Isomer A" The "Isomer A" of 1-(t-butyldimethylsilyl-3-(1'-hydroxy-1'-ethyl)-4-tritylthio-2-azetidinone, treated as described above gave pure "Isomer A" of 1-(t-butyldimethylsilyl)-3-(1'-paranitrobenzyldioxycarbonyl-1'-ethyl)-4-tritylthio-2-azetidinone as an oil. 95% ¹Hmr (CDCl₃) δ: 8.3–6.7 (19H, m, aromatics), 4.95 (2H, ABq, benzyl), 4.53 (1H, p, J=7.5, H-1', 4.31 (1H, d, J=6, H-4), 3.32 (1H, dd, J=6, J=7.5, H-3), 1.44 (3H, d, J=6.5), 0.95 (9H, s, tBu) and 0.2 ppm (6H, 2s, CH₃).

"Isomer D" Likewise "Isomer D" of 1-(t-butyldimethylsilyl-3-(1'-hydroxy-1'-ethyl)-4-tritylthio-2-azetidinone, gave pure "Isomer D" of 1-(t-butyldimethylsilyl)-3-(1'-paranitrobenzyldioxycarbonyl-1'-ethyl)-4-tritylthio-2-azetidinone, 90%. ¹Hmr (CDCl₃) δ: 8.3–6.7 (19H, m, aromatics), 5.20 (2H, ABq, benzyl), 4.72 (1H, d, J=5, H-4), 3.50 (1H, dq, J=6.5, J=0.5, H-1'), 2.85 (1H, dd, J=0.5, J=5, H-3), 1.03 (3H, d, J=6.5, CH₃), 1.0 (9H, s, t-Bu) and 0.35 ppm (6H, s, CH₃); mp 130°–2° C. Anal. calcd for C 66.83, H 6.20, N 4.10, S 4.70; found: C 66.56, H 6.28, N 3.96, S 4.89.

K. Preparation of (1'S,3S,4R and 1'R,3R,4S) 1-(t-Butyldimethylsilyl)-3-(1'-methanesulfonyloxy-1'-ethyl)-4-tritylthio-2-azetidinone (Isomer C)

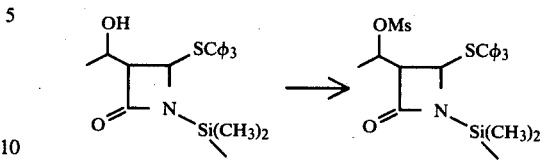

A solution of (1'S,3S,4R and 1'R,3R,4S)-1-(t-butyldimethylsilyl)-3-(1'-hydroxy-1'-ethyl)-4-tritylthio-2-azetidinone (Isomer C) (2.0 g, 4 mmol) in dichloromethane (80 ml) was treated at 5° C., with methanesulfonyl chloride (0.99 g, 8.6 mmol) and triethylamine (0.87 g, 8.6 mmol). After stirring at that temperature for 1 h under N₂, the solution was washed with brine, dried (MgSO₄) and evaporated to dryness. After crystallization from ether-pet-ether, 1.9 g (81.9%) of mesylate was obtained. mp 120°–22° C.; ¹Hmr (CDCl₃) δ: 7.13–7.61 (15H, m, aromatics), 4.50 (1H, d, J=2, H-4), 3.62 (1H, dq, J=6.5, 2, H-1'), 2.96 (1H, dd, J=2, 2, H-3), 2.84 (3H, s, methanesulfonyl), 1.22 (3H, d, J=6.5, H-2'), 0.99 (9H, s, Si-t-Bu) and 0.30 ppm (6H, s, Si-(CH₃)₂); ir $\nu_{max}$ (CHCl₃): 1746 (C=O), 1343 and 1180 cm⁻¹ (SO₂).

L. Preparation of (1'R,3S,4R and 1'S,3R,4S) 1-(t-Butyldimethylsilyl)-3-(1'-methanesulfonyloxy-1'-ethyl)-4-tritylthio-2-azetidinone (Isomer B)

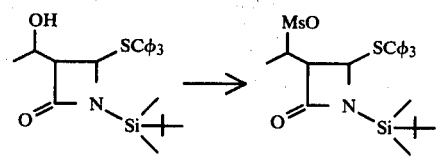

A solution of (1'R,3S,4R and 1'S,3R,4S) 1-(t-butyldimethylsilyl)-3-(1'-hydroxy-1'-ethyl)-4-tritylthio-2-azetidinone (Isomer B) (5.03 g, 10 mmol), methanesulfonylchloride (2.52 g, 22.0 mmol) and triethylamine (2.23 g, 22.0 mmol) in CH₂Cl₂ (200 ml) was stirred at 5° C. for 1 h. Then the solution was washed with brine, dried (MgSO₄) and evaporated to leave a residue which crystallized as a white solid when triturated in ether (5.40 g, 93%) mp 127°–31° C. ¹Hmr (CDCl₃) δ: 7.20–7.63 (15H, m, aromatics), 4.51 (1H, dq, J=5.0–6.2, H-1'), 4.10 (1H, d, J=2.0, H-4), 3.60 (1H, dd, J=5.0–2.0, H-3), 2.03 (3H, s, —CH₃), 1.01 (3H, d, J=6.2, H-2'), 0.90 (9H, s, t-Bu), 0.12 (6H, s, —CH₃); ir (CHCl₃) $\nu_{max}$: 1745 cm⁻¹ (C=O). M. Preparation of (1'S,3S,4R and 1'R,3R,4S) 3-(1'-p-Bromobenzenesulfonyloxy-1'-ethyl)-1-(t-butyldimethylsilyl)-4-tritylthio-2-azetidinone (Isomer C)

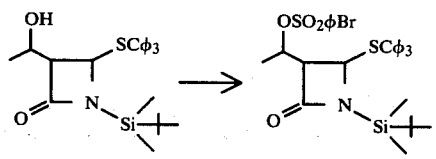

A solution of (1'S,3S,4R and 1'R,3R,4S) 1-(t-butyldimethylsilyl)-3-(1'-hydroxy-1'-ethyl)-4-tritylthio-2-azetidinone (Isomer C) (2.5 g, 5 mmol) in dry THF (100 ml) was cooled to −78° C. and treated with 2.52 M butyllithium/hexane (2.38 ml, 6 mmol). After 3-4 min p-bromobenzenesulfonylchloride (1.53 g, 6 mmol) dissolved in THF was added dropwise. The solution was stirred at −78° C. for 3 h and then allowed to come to room temperature. Then the solvent was evaporated and the desired product purified by column chromatography (silica gel, $CH_2Cl_2$) (3.36 g, 94.6%) mp 142°–44° C.; $^1$Hmr ($CDCl_3$) δ: 7.68 (4H, s, benzenefulsonyl), 7.28–7.60 (15H, m, aromatics), 4.59 (1H, d, J=1.8, H-4), 3.68 (1H, dq, J=6.2, H-1'), 2.99 (1H, dd, J=1.8, 2.0, H-3), 1.18 (3H, d, J=6.2, H-2'), 1.08 (9H, s, t-Bu), 0.40 and 0.38 (6H, 2S, —$CH_3$); ir ($CHCl_3$) $v_{max}$: 1749 cm$^{-1}$ (C=O).

N. Preparation of (1'S,3R,4R and 1'R,3S,4S) 3-(1'-Methoxymethyl-1'-ethyl)-4-tritylthio-2-azetidinone (isomer A).

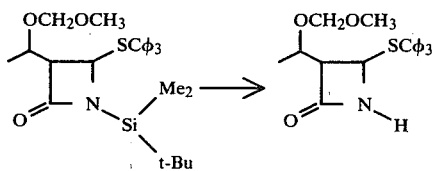

A cold (0° C.) HMPA-$H_2O$ (116 ml-13 ml) solution of Isomer A of 1-(t-butyldimethylsilyl)-3-(1'-methoxymetyl-1'-ethyl)-4-tritylthio-2-azetidinone (11 g, 20 mmol) was treated with sodium azide (2.7 g, 42 mmol). The cold bath was removed and the mixture was stirred for 30 min. It was then poured into cold water (1.3 l) and dried. The title compound recrystallized from ethyl acetate-hexanes (7.2 g, 83%) as a white solid mp 173°–174° C. $^1$Hmr ($CDCl_3$) δ: 7.10–7.0 (15H, m, aromatics), 4.85 (2H, ABq, J=7.4, O—$CH_2$—O), 4.53 (1H, d, J=5.2, H-4), 4.42 (1H, s, N-H), 4.15 (1H, m, H-1'), 3.5 (1H, m, H-3), 3.47 (3H, s, O—$CH_3$), 1.5 (3H, d, J=6, $CH_3$). ir (KBr) $v_{max}$: 3400–3500 (N—H) and 1760 cm$^{-1}$ C=O).

O. Preparation of (1'S,3S,4R and 1'R,3R,4S) 3-(1'-Methoxymethyloxy-1'-ethyl)-4-tritylthio-2-azetidinone (Isomer C)

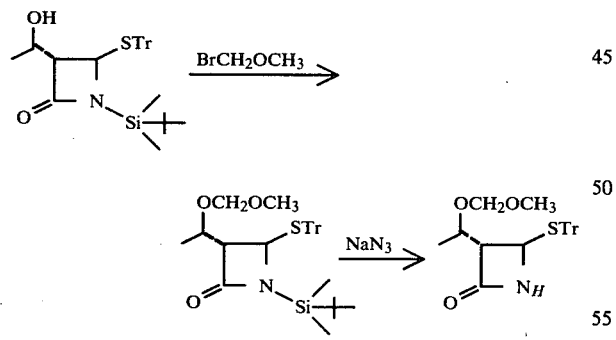

A cold (dry ice-acetone bath) solution of (1'S,3S,4R and 1'R,3R,4S) 1-(t-butyldimethylsilyl)-3-(1'-hydroxy-1'-ethyl)-4-tritylthio-2-azetidinone (5.03 g, 10 mmol) in THF (50 ml, distilled over LAH) was treated dropwise with a 1.6 M solution of n-butyl lithium in hexane (13.0 ml) until a pink coloration persisted. A THF (20 ml) solution of bromomethyl methylether (1.49 g, 0.97 ml, 1.19 mmol) was added dropwise. The mixture was stirred at −78° C. for 30 min and for a 3 h period at 0° C. It.was poured in an ice cold ammonium chloride solution and extracted with ether. The ether extracts were combined, washed with water, dried ($MgSO_4$) and concentrated to give crude (1'S,3S,4R and 1'R,3R,4S) 1-(t-butyldimethylsilyl)-3-(1'-methoxymethyloxy-1'-ethyl)-4-tritylthio-2-azetidinone (5.83 g, 100%) which was deprotected as described below:

A cold (ice bath) solution of the above derivative (5.83 g, 10 mmol) in HMPA-$H_2O$ (90 ml-10 ml) was treated with sodium azide (1.365 g, 21 mmol). The cooling bath was removed and the mixture was stirred at room temperature for a 2 h period. It was then poured slowly into ice cold water (900 ml) and stirred for 30 min. The precipitate was collected by filtration and redissolved in methylene chloride. The solution was washed with water and brine and dried ($MgSO_4$) to give the title compound (3.0 g, 69.3%), mp 172–2.5 (ethyl acetate-hexane); ir ($CHCl_3$) $v_{max}$: 3400 (N—H) and 1760 cm$^{-1}$ (C=O); $^1$Hmr ($CDCl_3$) δ: 7.67–7.12 (15H, m, H aromatics), 4.63 (2H, center of ABq, J=6, O—$CH_2$—O), 4.49 (1H, s, N—H), 4.40 (1H, d, J=3, H-4), 4.25–3.80 (1H, m, H-1'), 3.35–3.15 and 3.26 (4H, s+m, $CH_3$ and H-3) and 1.30 ppm (3H, d, J=6, $CH_3$).

P. Preparation of (1'R,3S,4R and 1'S,3R,4S) 3-(1'-Formyloxy-1'-ethyl)-4-tritylthio-2-azetidinone (Isomer B)

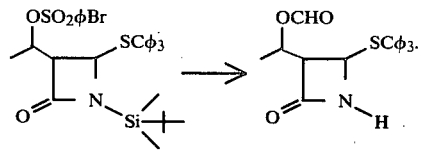

A solution of (1'S,3S,4R and 1'R,3R,4S) 3-(1'-p-bromobenzenesulfonyloxy-1'-ethyl)-1-(t-butyldimethylsilyl)-4-tritylthio-2-azetidinone (Isomer C) in DMF (3 ml) was heated at 50° C. for 48 h and then at 100° C. for 4 h. The reaction mixture was then diluted with $H_2O$ and extracted with ether. The ethereal extracts were washed with brine, dried ($MgSO_4$) and evaporated. The title compound was obtained as white crystals after purification by column chromatography (silica gel, 5% $CH_3CN$—$CH_2Cl_2$) (2 mg, 4.8%) mp 131°–32° C.; $^1$Hmr ($CDCl_3$) δ: 8.07 (1H, s, CHO), 7.24–7.56 (15H, m, aromatics), 5.23 (1H, dq, J=6.4, 7, H-1'), 4.38 (1H, dm J=2.4, H-4), 4.25 (1H, s, NH), 3.20 (1H, dd, J=7, 2.4, H-3), 1.43 (3H, d, J=6.4, H-2'); ir ($CHCl_3$) $v_{max}$: 3400 (NH), 1765 (C=O), 1725 cm$^{-1}$ (C=O).

Q. Preparation of (1'R,3S,4R and 1'S,3R,4S) 3-(1'-Acetoxy-1'-ethyl)-4-tritylthio-2-azetidinone (isomer B)

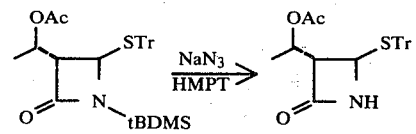

Pure derivative (1'R,3S,4R and 1'S,3R,4S) 1-(t-butyldimethylsilyl)-3-(1'-acetoxy-1'-ethyl)-4-tritylthio-2-azetidinone (5.77 g, 10.57 mmol) was dissolved in warm HMPT-water (60 ml, 10 ml). The solution was cooled down at room temperature and $NaN_3$ (1.2 g was added in. It was stirred for 45 min (reaction progression was followed by tlc) and poured slowly in stirred cold water (800 ml). The mixture was stirred for 20 more min. The crystalline material was collected and washed with water. It was redissolved in $CH_2Cl_2$, washed with water (twice) and brine and dried over MgSO4. Solvent evaporation left a foam which crystallized out from ether-petroleum ether (4.90 g, 96.5%, mp 143°–44.5° C.).

ir (CH2Cl2)$\nu_{max}$: 3395 (N—H), 1772, 1738 cm$^{-1}$ (C=O). $^1$Hmr (CDCl3) δ: 7.9–6.8 (15H, m, H aromatic), 5.12 (1H, center of dq, J=6.5, 7.5, H-1'), 4.33 (1H, d, J=2.8, H-4), 4.20 (1H, bs, N—H), 3.17 (1H, ddd, $J_{3-1'}$=7.5, $J_{3-4}$=2.8, $J_{3-NH}$=1, H-3), 2.1 (3H, s, CH3CO), 1.35 (3H, d, J-6.5, CH3).

R. Preparation of 3-(1'-Hydroxy-1'-ethyl)-4-tritylthio-2-azetidinone. Mixture of four isomers)

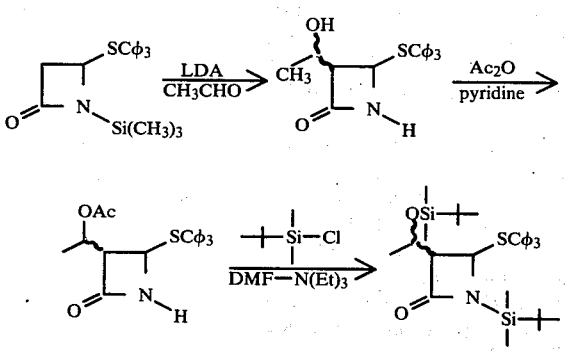

A solution of lithium diisopropyl amide[1] (0.74 mmol) was prepared at −78° C. in dry tetrahydrofuran (5 ml) from diisopropyl amine (0.103 ml, 0.74 mmol) and BuLi (0.29 ml of a 2.52 M in hexane). After 30 min at −78° C., a solution of the (R and S) 1-trimethylsilyl-4-tritylthio-2-azetidinone (0.292 g, 6.99 mmol) in dry tetrahydrofurane (2 ml) was added dropwise. After 5 min, excess of freshly distilled acetaldehyde (0.2 ml) was added all at once. After 20 min at −78° C., tlc indicated complete disappearance of starting materials and the reaction mixture was quenched by adding to a saturated solution of ammonium chloride. Extraction with ethyl acetate (2×25 ml) followed by washing of the combined organic phases with saturated NH4Cl, brine and drying on anhydrous magnesium sulfate gave, after evaporation of the solvent, a yellow oil. Filtration of this oil on silica gel (10 g, elution C6H6:EtOAc, 6:4) gave a mixture of alcohols (0.215 g, 80%). This mixture ($^1$Hmr) cannot be separated either by hplc or by tlc.

a: Acetylation

Acetylation of an aliquot of the mixture (0.065 g) with excess acetic anhydride (1.0 ml) and pyridine (1.4 ml) gave a mixture of acetates. hplc Analysis indicated four components[2]: (a) 34:6%; (b) 17.4%; (c) 30.1%; (d) 17.9%. Compound (a) was identical to the isomer B by direct comparison (hplc).[4]

b: t-Butyldimetyl silyl derivatives

The mixture of alcohols (0.121 g, 0.34 mmol) was treated with t-butyl dimethylchlorosilane (0.117 g, 0.776 mmol) and triethyl amine (0.10 ml, 7.14 mmol) in dry dimethylformamide (1 ml) for 36 h at room temperature. After dilution with ethyl acetate, the solution was washed with saturated ammonium chloride and dried over anhydrous magnesium sulfate. Evaporation gave an oil (0.716 g) which contains 4 components by HPLC. a=3.7%; b=60.6%; c=31.1%; d=4.6% (the identity of each one has not been established)[4]

NOTE:

[1] Butyl lithium and lithium hexamethyl disilazane were ineffective

[2] Order of increasing polarity

[3] Acetylation of the product derived from 1-t-butyldimethylsilyl-4-tritylthio-2-azetidinone gave the following ratio: d=29.5%; c=24.1%; b=33.8%; a=12.6%

[4] Reaction of a mixture of alcohols derived from (R and S) 1-(t-butyldimethylsilyl)-4-tritylthio-2-azetidinone gave the following proportions: a=5.2%; b=41.3%; c=48%; d=4.6%

S. Preparation of (1'R,3S,4R and 1'S,3R,4S) 3-(1'-Benzoxy-1'-ethyl)-4-tritylthio-2-azetidinone (Isomer B)

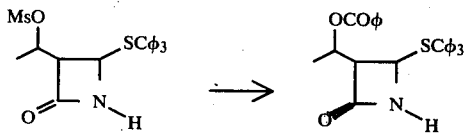

A solution of (1'S,3S,4R and 1'R,3R,4S) 3-(1'-methanesulfonyloxy-1'-ethyl)-4-tritylthio-2-azetidinone (Isomer C) (035 mg, 2 mmol) and sodium benzoate (432 mg, 3 mmol) in 10% H2O-DMF (10 ml) was heated at 90° C. for 7.5 h. Then the reaction mixture was diluted with H2O and extracted with ethyl acetate. The organic extracts were washed with brine, dried (MgSO4) and evaporated. The residue, purified by column chromatography (silica gel, 5% CH3CN —CH2Cl2) gave the title compound as a white solid (108 mg, 23.2%) mp 158° C. $^1$Hmr (CDCl3) δ: 7.03–8.25 (20H, m, aromatics), 5.32 (1H, dq, J=6.1, 9, H-1'), 4.40 (1H, d, J=2.5, H-4), 4.30 (1H, s, N—H), 3.40 (1H, dd, J=9, 2.5, H-3), 1.50 (3H, d, J=6.1, H-2'); ir (CHCl3) $\nu_{max}$: 3400 (N—H), 1765 (C—O), 1715 cm$^-$(C=O).

T. Preparation of 3-(1'-Paranitrobenzyldioxycarbonyl-1'-ethyl)-4-tritylthio-2-azetidinone (4 isomers).

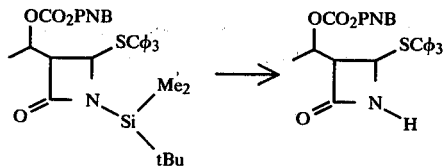

"Isomer C"

(a) A solution of "Isomer C" of 1-(t-butyldimethylsilyl)-3-(1'-paranitrobenzyldioxycarbonyl-1'-ethyl)-4-tritylthio-2-azetidinone (1.3 g) in a mixture of TFA (5 ml), water (5 ml), dichloromethane (20 ml) and methanol (30 ml) was stirred for 2 days at room temperature. The solution was diluted with water and the aqueous phase extracted with dichloromethane. The combined organic phases were washed with sodium bicarbonate and water, dried and concentrated to leave an oil. Crystallization from ether gave the pure title compound (902 mg), mp 78°–80° C.; $^1$Hmr (CDCl3): 8.25–6.75 (19H, m, aromatics), 5.21 (2H, s, benzyl), 5.05 (1H, m, H-1'), 4.40 (1H, s, N—H) 4.27 (1H, d, J=2.8, H-4), 3.37 (1H, dd, J=5.3, 2.8, H-3) and 1.37 ppm (3H, d, J=6.5, CH3); ir (CHCl3) $\nu_{max}$ :3390 (N—H), 1765 and 1745 (shoulder) (C=O, and 1525 cm$^{-1}$ (NO2).

(b) A cold (0° C.) HMPT-H2O (90 ml–19 ml) solution of "Isomer C" of 1-(t-butyldimethylsilyl)-3-(1'-paranitrobenzyldioxycarboxyl-1'-ethyl)-4-tritylthio-2-azetidinone (9.11 g, 13.3 mmol) was treated with sodium azide (1.82 g, 27.9 mmol). The cold bath was removed and the mixture was stirred for 30 min. It was then poured into water (1 l) and extracted with ether (5×200 ml). The ether fractions were combined and washed with water (5×200 ml), brine and dried over MgSO4. Alternatively since the title compound precipitated out on water dilution, it was filtered off and recrystallized from ether; 7.22 g, 89%, mp 78°–80° C.

"Isomer B"

"Isomer B" of 3-(1′-paranitrobenzyldioxycarbonyl-1′-ethyl)-4-tritylthio-2-azetidinone was prepared as described above for the "Isomer C"; 92%; mp 155.5°–6° C. (ether); $^1$Hmr (CDCl3) δ:8.25–6.80 (19H, m, aromatics), 5.20 (2H, s, benzyl), 4.95 (1H, m, H-1′), 4.35 (1H, d, J=2.9, H-4), 4.17 (1H, s, N—H), 3.20 (1H, dd, J=10.8, J=2.9, H-3) and 1.40 ppm (3H, d, J=7.5, CH3); ir (CHCl3)$\nu_{max}$:3480, 3390 (N—H), 1772, 1750 (C=O), and 1525 cm$^{-1}$(NO2). Anal. calcd for C32H28N2O6S: C 67.59, H 4.96, N 5.64; found: C 67.48, H 4.98, N 4.92, S 5.67.

"Isomer A"

"Isomer A" of 3-(1′-paranitrobenzyldioxycarbonyl-1′-ethyl)-4-tritylthio-2-azetidinone was prepared as described above for the "Isomer C"; mp 205°–6° C. $^1$Hmr (CDCl3) δ:8.2–6.7 (19H, m, aromatics), 5.22 (2H, ABq, benzyl), 5.57–4.85 (1H, m, H-1′), 4.65 (1H, N—H), 4.50 (1H, d, J=6.5, H-4), 3.65 (1H, dd, J=6.5, 12, $J_{N—H}$=1, H-3) and 1.52 ppm (3H, d, J=7.5).

"Isomer D"

"Isomer D" of 3-(1′-paranitrobenzyldioxycarbonyl-1′-ethyl)-4-tritylthio-2-azetidinone was prepared as described above for the "Isomer C"; HU 1Hmr (CDCl3) δ:8.15–6.70 (19H, m, aromatics), 5.23 (2H, ABq, benzyl), 5.20 (1H, m, H-1′), 4.75 (1H, NH), 4.52 (1H, d, J=5.5, H-4), 3.42 (1H, J=5.5, 3, H-3 and 1.5 ppm (3H, d, J=6.5, CH3). (J value for H-3 taken after D2O. exchange).

U. Preparation of (1′R,3S,4R and 1′S,3R,4S) 3-(1′-ethanesulfonyloxy-1′-ethyl)-4-tritylthio-2-azetidinone (isomer B)

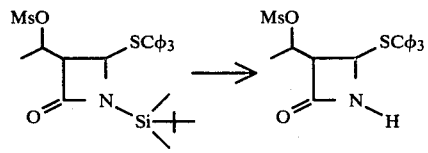

A solution of (1′R,3S,4R and 1′S,3R,4S) 1-(t-butyl-dimethylsilyl)-3-(1′-methanesulfonyloxy-1′-ethyl)-4-trithylthio-2-azetidinone. (Isomer B) (4.95 g, 8.5 mmol) and sodium azide (1.11 g, 17.0 mmol) in 10% H2O-HMPA (50 ml) was stirred at room temperature for 30 min. Then the solution was diluted with water (250 ml) and extracted with ether. The organic extracts were washed with brine, dried (MgSO4) and evaporated. Crystallization of the residue (ether-petether) gave the title compound (3.33 g, 83.8%). mp 130°–31° C. $^1$Hmr (CDCl3) δ:7.20–7.62 (15H, m, aromatics), 4.97 (1H, dq, J=6.4, 6.1, H-1′), 4.56 (1H, d, J=2.8, H-4), 4.22 (1H, m, N—H), 3.27 (1H, dd, J=6.1, 2.8, H-3), 3.0 (3H, s, —CH3), 1.63 (3H, d, J=6.4, H-2′); ir (nujol) $\nu_{max}$:3195 (n-H), 1768 cm$^{-1}$ (C=O).

V. Preparation of (1′S,3S,4 R and 1′R,3R,4S)3-(1′-ethanesulfonyloxy-1′-ethyl)-4-tritylthio-2-azetidinone (Isomer C)

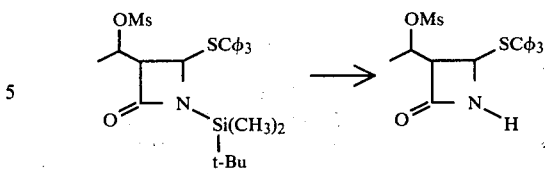

A solution of (1′S,3S,4R and 1′R,3R,4S)1-(t-butyl-dimethylsilyl)-3-(1′-methanesulfonyloxy-1′-ethyl)-4-tritylthio-2-azetidinone (isomer C) (2.85 g; 4.9 mmol) in 10% aqueous HMPA (25 ml) was treated with sodium azide (0.65 g, 10 mmol) and stirred at 25° C. for 0.5 h. By diluting the solution with water (250 ml), the reaction product was forced to crystallize out. The crude mesylate was redissolved in dichloromethane, washed with brine, dried (MgSO4) and evaporated. Trituration in ether gave the title compound as white crystals mp 155°–60° C.; 1.80 g; 78.6%; $^1$Hmr (CDCl3) δ:7.43 (15H, m, aromatic), 5.02 (1H, dq, J=6.9, 4.9, H-1′), 4.55 (1H, s, N—H), 4.95 (1H, d, J=3, H-4), 3.33 (1H, dd, J=4.9, 3, H-3), 1.51 (3H, d, J=6.9, H-2′); ir $\nu_{max}$:3395 (N—H), 1768 cm$^{-1}$ (C=O); Anal. calcd for C25H25NO4S. C 64.22, H 5.39, N 3.00; found: C 63.93, H 5.39, N 3.24%.

W. Preparation of (1′S,3S,4R and 1′R,3R,4S) 3-(1′-p-Bromobenzenesulfonyloxy-1′-ethyl)-4-tritylthio-2-azetidinone (Isomer C)

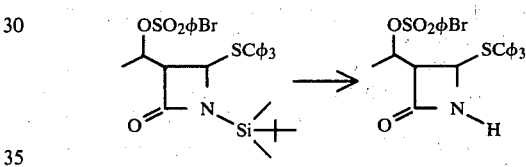

A solution of (1′S,3S,4R and 1′R,3R,4S) 3-(1′-p-bromobenzenesulfoxyloxy-1′-ethyl)-1-(t-butyldimethyl-silyl)-4-tritylthio-2-azetidinone (Isomer C) (1.42 g, 2 mmol) and sodium benzoate (0.865 g, 6 mmol) in 10% H2O-HMPA (40 ml) was stirred at room temperature for 1 h. Then the solution was diluted with H2O (100 ml) and extracted with ether. The ether extracts were washed with brine, dried (MgSO4) and evaporated. The crude crystalline title compound was triturated in a small volume of ether and collected by filtration (0.92 g, 77%) mp 125°–26° C. $^1$Hmr (CDCl3) δ:7.80 (4H, s, benzenesulfonyl), 7.30–7.65 (15H, m, aromatics), 5.13 (1H, dq, J=6.5, 4.0, H-1′), 4.50 (1H, d, J=2.9, H-4), 4.40 (1H, s, N—H), 3.40 (1H, dd, J=4.0, 2.9, H-3), 1.50 (3H, d, J=6.5, H-2′); ir (CHCl3) $\nu_{max}$:3400 cm$^{-1}$ (N—H), 1770 cm$^{-1}$ (C=O).

X. Preparation of (1′R,3S,4R and 1′S,3R,4S) 3-(1′-Hydroxy-1′-ethyl)-4-tritylthio-2-azetidinone (Isomer B)

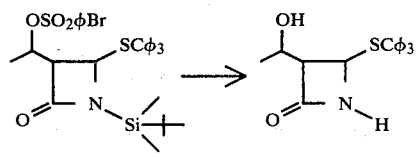

To a warm solution of (1′S,3S,4R and 1′R,3R,4S) 3-(1′-p-bromobenzenesulfonyloxy-1′-ethyl)-1-(t-butyl-dimethylsilyl)-4-tritylthio-2-azetidinone (Isomer C) in HMPA (5 ml) was added dropwise 1 ml of H2O. The reaction mixture was kept at 90° C. for 20 h, then diluted with ether and washed 4 times with brine. The organic solution was dried (MgSO4), evaporated and the crude title compound purified by column chromatography (silica gel, 15% CH3CN—CH2Cl2). A white solid was obtained (122 mg, 44.5%) mp 187°–189° C. which was found to be identical to a sample of the title compound prepared by another method.

Y. Preparation of 3-(1'-Hydroxy-1'-ethyl)-4-tritylthio-2-azetidinone

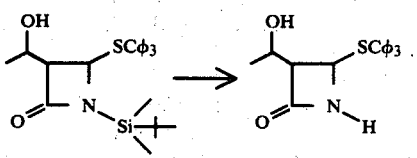

Both isomers, (1'S,3S,4R and 1'R,3R,4S) 3-(1'-hydroxy-1'-ethyl)-4-tritylthio-2-azetidinone (Isomer C) and (1'R,3S,4R and 1'S,3R,4S) 3-(1'-hydroxy-1'-ethyl)-4-tritylthio-2-azetidinone (Isomer B) were prepared by the same method. For example, a solution of (1'S,3S,4R and 1'R,3R,4S) 1-(t-butyldimethylsilyl)-3-(1'-hydroxy-1'-ethyl)-4-tritylthio-2-azetidinone (Isomer C) (1.0 g, 2 mmol) and sodium benzoate (0.865 g, 6 mmol) in 10% H2O—DMF (40 ml) was stirred at room temperature for 18 h. Then the reaction mixture was diluted with H2O and extracted with ether. The organic extracts were washed with brine, dried (MgSO4) and evaporated. The crude title compound was crystallized from cold ether (0.47 g, 61%) mp 134°–35° C. $^1$Hmr (CDCl3) δ: 7.12–7.56 (15H, m, aromatics), 4.48 (1H, s, N—H), 4.28 (1H, d, J=2.8, H-4), 2.94 (1H, dq, J=6.5, 6.2, H-1'), 3.06 (1H, dd, J=6.2, 2.8, H-3), 2.18 (1H, s, —OH), 1.30 (3H, d, J=6.5, H-2'); ir (CHCl3) $\nu_{max}$: 3400 (n-H), 1760 cm$^{-1}$ (C=O). Similarly (1'R,3S,4R and 1'S,3R,4S) 1-(t-butyldimethylsilyl)-3-(1'-hydroxy-1'-ethyl)-4-tritylthio-2-azetidinone (Isomer B) mp 190°–92° C. $^1$Hmr (CDCl3) δ: 7.10–7.55 (15H, m, aromatics), 4.45 (1H, d, J=2.5, H-4), 4.28 (1H, s, NH), 4.10 (1H, dq, J=6.4, 5.3, H-1'), 3.08 (1H, dd, J=5.3, 2.5, H-3), 1.50 (1H, s, —OH), 1.30 (3H, d, J=6.4, H-2'); ir (CHCl3) $\nu_{max}$: 3400 (N—H), 1760 cm$^{-1}$ (C=O)

Z. Preparation of (1'S,3R,4R and 1'R,3S,4S) 3-(1'-Methoxymethyl-1'-ethyl)-1-(paranitrobenzyl 2"-hydroxy-2"-acetate)-4-tritylthio-2-azetidinones (Isomer A)

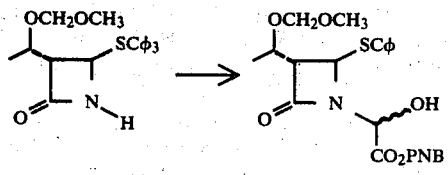

A mixture of Isomer A of 3-(1'-methoxymethyl-1'-ethyl)-4-tritylthio-2-azetidinone (7.5 g, 17.3 mmol), paranitrobenzyl glyoxylate hydrate (4.7 g, 20.8 mmol) and toluene (300 ml) was heated under reflux for 1 h in a Dean and Stark apparatus filled with 3 A molecular sieves. The solution was cooled in ice and triethylamine (0.24 ml, 1.7 mmol) was added dropwise. The mixture was stirred for 1 h, washed with diluted hydrochloric acid, sodium bicarbonate and brine, dried and concentrated to give the title compound as a foam (10.5 g, 94%). $^1$Hmr (CDCl3) δ: 8.25–6.84 (19H, m, aromatics), 5.24 (2H, s, benzyls), 4.67–4.83 (3H, m, O—CH2 and H-4), 4.34–4.55 (1H, m, H-2"), 4.02 (1H, m, H-1'), 3.54 (1H, m, H-3), 3.40 (3H, s, O—CH3), 1.38 (3H, d, J=6.5, CH3); ir (KBr) $\nu_{max}$: 3360 (OH), 1770 (C=O of β-lactam), 1735 (C=O of ester) and 1605 cm$^{-1}$ (aromatics).

AA. Preparation of (1'S,3S,4R and 1'R,3R,4S) 3-(1'-Methoxymethoxy-1'-ethyl)-1-(paranitrobenzyl 2"-hydroxy-2"-acetate)-4-tritylthio-2-azetidinone (Isomer C)

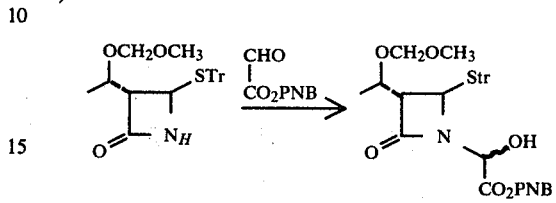

A solution of hydrated paranitrobenzyl glyoxylate (1.73 g, 7.11 mmol) was refluxed in toluene (90 ml) using a Dean Stark condenser filled with 3 A molecular sieves for a 2 h period. To the boiling solution was added (1'S,3S,4R and 1'R,3R,4S) 3-(1'-methoxymethyloxy-1'-ethyl)-4-tritylthio-2-azetidinone (3.0 g, 6.93 mmol) and the mixture was refluxed for 2 h more. The mixture was cooled to room temperature, triethyl amine (70 mg, 97 μl, 0.69 mmol) was added and it was stirred for 2 h. The reaction mixture was diluted with ether, washed with 1% aqueous HCl, water, 1% aqueous NaHCO3, water and brine, dried (MgSO4) and concentrated to give the title compound (4.60 g, 100%); ir (CHCl3) $\nu_{max}$: 3530–3100 (O-H), 1765, 1750 (C=O) and 1525 cm$^{-1}$ (NO2); $^1$Hmr (CDCl3) δ: 8.22, 8.18 (2H, 2d, J=8, Hm aromatics), 7.67–7.0 (17H, m, H-aromatics), 5.3 (2H, bs, CH2-PNB), 5.30–5.02 (m, H-2"), 4.89–4.52 (m, H-1' and O-H), 4.63, 4.59 (1H, 2d, J=2, H-4), 4.33, 4.30 (2H, 2 center of 2 ABq, J=7, J=7, O—CH2—O), 4.1–3.67 (1H, m, H-1'), 3.2 (1H, H-3), 3.1, 3.6 (3H, 2s, CH3—O), and 1.15 ppm (3H, d, J=6.5, CH3).

BB. Preparation of (1'R,3S,4R and 1S,3R,4S) 3-(1'-Acetoxy-1'-ethyl)-1-(paranitrobenzyl-2"-hydroxy-2"-acetate)4-tritylthio-2-azetidinone

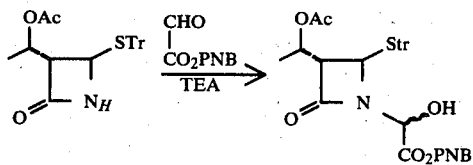

"Isomer B"

A solution of hydrated p-nitrobenzyl glyoxylate (triturated with ether) (1.82 g, 30 mol) was refluxed in benzene through a Dean Stark condenser filled with 3 A molecular sieves for 2 h. To that was added azetidinone (1'R,3S,4R and 1'S,3R,4S) 3-(1'-acetoxy-1'-ethyl)-4-tritylthio-2-azetidinone (10.88 g, 25.2 mmol) and the mixture was refluxed for 1 h more. The solution was cooled at room temperature and triethyl amine (0.35 ml, 2.5 mmol was added. It was then stirred for 2 h; the reaction progression being followed by tlc. *Solvent evaporation afforded a white foam in quantitative yield (100%, mixture of epimers)
*Alternatively the solution can be acid and base washed.

ir (CH3Cl2) $\nu_{max}$: 3520 (OH), 1775, 1745 cm$^{-1}$ (C=O); $^1$Hmr (CDCl3) δ: 8.2, 8.18 (2H, 2d, J=8, Ho aromatic), 7.80–6.90 (17H, m, H-aromatic), 5.28, 5.17 (2H, 24, CH2-PNB), 4.89 (0.67H, d, J=7.2, CHO), 4.80

(center of m, H-1'), 4.38 (0.33H, 2d, J=8.8, CHO), 4.22 (D.33H, d, J₄₋₃=2.5, H-4), 4.09 (0.67H, d, J₄₋₃=2.1, H-4), 3.65 (D.67H, dd, J₃₋₁'=5.8, J₃₋₄=2.1, H-3), 3.47 (0.33H, dd, J₃₋₁'=5.5 J₃₋₄=2.5, H-3), 3.33 (0.33H, d, J=8.8, OH), 3.23 (0.67H, d, J=7.5, OH), 1.88, 1.86 (3H, 2s, CH₃CD), 1.10, 1.06 (3H, 2d, J=5.8, 6.3, CH₃).

CC. Preparation of 3-(1'-Paranitrobenzyldioxycarbonyl-1'-ethyl)-1-(paranitrobenzyl 2''-hydroxy-2''-acetate)4-tritylthio-2-azetidinone (4 isomers).

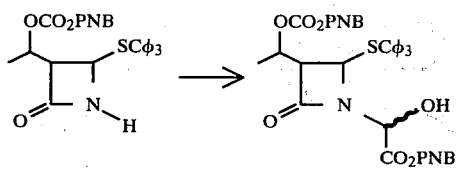

"Isomer C"

A mixture of "Isomer C" of 3-(1'-paranitrobenzyldioxycarbonyl-1'-ethyl)-4-tritylthio-2-azetidinone (1.70 g, 0.3 mmol), paranitrobenzyl glyoxylate hydrate (815 mg, 3.6 mmol) and toluene (50 ml) was heated under reflux 7 days in a Dean and Stark apparatus filled with 3 A molecular sieves. The cooled solution was washed with dilute hydrochloric acid, sodium bicarbonate and brine, dried and concentrated to give the title compound (2.1 g) as an epimeric mixture at carbon-2''. Purification was effected by chromatography over silica gel. Alternatively the title compound could be prepared by using a catalytic amount of triethyl amine. Less polar epimer at 2'': ¹Hmr (CDCl₃) δ: 8.25–6.80 (23H, m, aromatics), 5.30 and 3.12 (4H, 2s, benzyls), 4.65 (1H, d, J=9, H-2''), 4.45 (1H, d, J=2.5, H-4), 4.45–4.10 (1H, m, H-1'), 3.50 (1H, d, J=9, 2''-OH), 3.28 (1H, dd, J=2.5, J=2.5, H-3) and 1.23 ppm (3H, d, J=6.5, CH₃); ir (CHCl₃) $v_{max}$: 3530 to 3200 (D-H), 1765, 1750 (C=O) and 1525 cm⁻¹ (NO₂). More polar isomer at C-2'': ¹Hmr (CDCl₃) δ: 8.25–6.85 (23H, m, aromatics), 5.25 and 5.08 (4H, 2s, benzyls), 5.05 (1H, d, J=7, H-2''), 4.35 (1H, d, J=2.5, H-4), 4.40–4.05 (1H, m, H-1'), 3.42 (1H, J=7, 2''-OH), 3.33 (1H, dd, J=2.5, 2.5, H-3), 1.23 (3H, d, J=6.5, CH₃); ir (CHCl₃) $v_{max}$: 3520 to 3200 (O-H), 1755 (C=O) and 1525 cm⁻¹ (NO₂).

"Isomer B"

A mixture of hydrated paranitrobenzylglyoxylate (1.74 g, 7.66 mmol) and (1'R,3S,4R and 1'S,3R,4S) 3-(1'-paranitrobenzyldioxycarbonyl-1'-ethyl)-4-tritylthio-2-azetidinone (3.63 g, 6.38 mmol) was refluxed in toluene (70 ml) on a Dean Stark condenser filled with 3 A molecular sieves for 3 h. The solution was cooled down to room temperature and triethyl amine (64.5 mg, 89 ml, 0.639 mmol) was added. It was then stirred for 4 h, diluted with ether and washed with 2% aqueous HCl, water, 2% aqueous NaHCO₃, water and brine. It was dried and concentrated to give pure title compound (5.02 g, 100%). Separation of the 2 epimers was effected on preparative silica gel plate. Less polar epimer at 2'': ir (CHCl₃) $v_{max}$: 3500 (O-H), 1772, 1750 (C=O) 1525 cm⁻¹ (NO₂); ¹Hmr (CDCl₃) δ: 8.30–8.00 and 7.65–6.80, (23H, m, aromatics), 5.27 and 5.13 (4H, 2s, benzyls), 4.71 (1H, m, J=6.5, 6.5, H-1'), 4.28 (1H, d, J=2.2, H-4), 4.23 (1H, d, J=8.7, H-2''), 3.50 (1H, dd, J=2.2, 6.5, H-3), 3.28 (1H, d, J=8.7, O-H) and 1.18 ppm (3H, d, J=6.5, CH₃). More polar epimer: ir (CHCl₃) $v_{max}$: 3480 (O-H) 1772, 1750 (C=O) and 1525 cm⁻¹ (NO₂); ¹Hmr (CDCl₃) δ: 8.35–6.90 (23H, m, aromatics), 5.15 (4H, benzyls), 4.72 (1H, d, J=7.5, H-2''0), 4.90–4.50 (1H, m, J=6.5, 6.5, H-1'), 4.10 (1H, d, J=2, H-4), 3.68 (1H, dd, J=2, 6.5, H-3), 3.28 (1H, d, J=6.5, O-H) and 1.15 ppm (3H, d, J=6.5, CH₃).

"Isomer A"

The "Isomer A" of 3-(1'-paranitrobenzyldioxycarbonyl-1'-ethyl)-4-tritylthio-2-azetidinone likewise gave a mixture of "Isomer A" of 3-(1'-paranitrobenzyldioxycarbonyl-1'-ethyl)-1-(paranitrobenzyl 2''-hydroxy-2''-acetate)-4-tritylthio-2-azetidinones. ¹Hmr (CDCl₃) δ: 8.3–6.7 (23H, m, aromatics), 5.17 (2H, benzyls), 5.0 (1H, m, H-1'), 4.9 and 4.8 (1H, 2d, J=6, H-4, two epimers), 4.32 and 3.96 (1H, 2s, H-2'', two epimers), 3.68 (1H, dd, J=6, 6, H-3 (and 1.47 ppm (3H, 2d, J=6.5, CH₃, two epimers).

"Isomer D"

The "Isomer D" of 3-(1'-paranitrobenzyldioxycarbonyl-1'-ethyl)-4-tritylthio-2-azetidinone likewise gave a mixture of "Isomer D" of 3-(1'-paranitrobenzyldioxycarbonyl-1'-ethyl)-1-(paranitrobenzyl 2''-hydroxy-2''-acetate)-4-tritylthio-2-azetidinones. ¹Hmr (CDCl₃) δ: 8.30–6.60 (23H, m, aromatics), 5.20 (4H, m, benzyls), 4.83 (1H, 2d, J=5, H=4), 5.50–4.30 (2H, m, H-1' and H-2''), 3.48 (1H, m, H-3), 3.15 (1H, m, O-H), 1.37 and 1.30 ppm (3H, 2d, CH₃).

DD. Preparation of (1'S,3S,4R and 1'R,3R,4S)3-(1'-Methanesulfonyloxy-1'-ethyl)-1-(paranitrobenzyl 2''-hydroxy-2''-acetate)-4-tritylthio-2-azetidinone (isomer C) (epimers at C₂'').

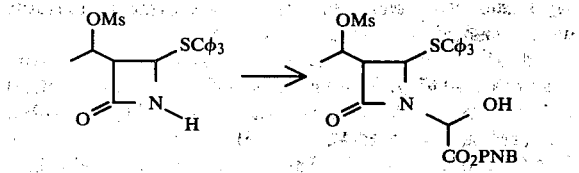

A solution of paranitrobenzylglyoxylate hydrate (9.72 g; 42.6 mmol) in benzene (350 ml) was refluxed for 2 h, removing the water azeotropically in a Dean-Stark trap. To that solution was added the (1'S,3S,4R and 1'R,3R,4S)3-(1'-methanesulfonyloxy-1'-ethyl)-4-tritylthio-2-azetidinone (16.62 g, 35.5 mmol) and the reflux maintained for an additional 0.5 h. Then the reaction mixture was cooled to room temperature, treated with triethylamine (0.5 ml; 3.5 mmol) and stirred for 3 h in order to complete the reaction. Evaporation of the solvent left a white foam which was used as such in the next step: ¹Hmr (CDCl₃) δ: 8.12 (2H, d, J=9, Hm aromatic), 7.28 (17H, part of d, Ho aromatic, trityl), 5.28 (2H, s, —CH₂— PNB), 4.88 (0.5 H, s, H-1''), 4.62 (1.5H, m, H-2'' and H-4), 4.00 (2H, m, H-1', —OH), 3.15 (1H, m, H-3), 2.73 (3H, s, mesylate and 1.30 ppm (3H, d, J=6 Hz, H-2'); ir $v_{max}$: 3520 (O-H), 1775 (C=O) and 1765 cm⁻¹ (C=O).

EE. Preparation of (1'S,3R,4R and 1'R,3S,4S) 3-(1-Methoxymethyl-1'-ethyl)-1-(paranitrobenzyl 2''-chloro-2''-acetate)-4-tritylthio-2-azetidinone (Isomer A)

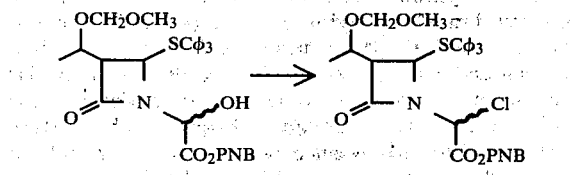

Pyridine (1.1 ml, 14.2 mmol) was added dropwise to a solution of Isomer A of 3-(1'-methoxymethyl-1'- ethyl)-1-(paranitrobenzyl-2''-hydroxy-2''-acetate)-4-tritylthio-2-azetidinone (7 g, 10.9 mmol) in THF (350 ml) cooled to −15° C. Immediately after thionyl chloride (1.0 ml, 14.0 mmol) was added dropwise and the mixture was stirred at −15° for 0.5 h. The precipitate was removed by filtration and washed with benzene. The combined filtrates were concentrated, the residue dissolved in fresh benzene and the solution treated with activated charcoal, filtered and concentrated to leave to title compound as an oil (6.5 g, 90%), $^1$Hmr (CDCl$_3$) δ: 6.65-8.35 (19H, m, aromatics), 5.24 (2H, s, benzyl), 3.43 (3H, s, OCH$_3$) and 1.42 ppm (3H, d, J=6, CH$_3$).

FF. Preparation of (1'S,3S,4R and 1'R,3R,4S) 3-(1'-ethoxymethoxyloxy-1'-ethyl)-1-(paranitrobenzyl 2''-chloro-2''-acetate)-4-tritylthio-2-azetidinone (Isomer C)

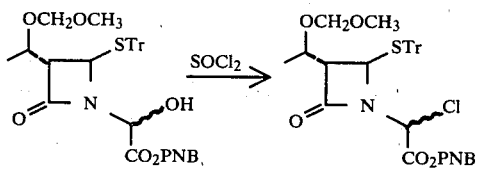

A cold (ice-MeOH bath) THF (60 ml, distilled over LAH) solution of (1'S,3S,4R and 1'R,3R,4S) 3-(1'-methoxymethyloxy-1'-ethyl)-1-paranitrobenzyl 2''-hydroxy-2''-acetate)-4-tritylthio-2-azetidinone (4.25 g, 6.62 mmol) was treated dropwise with pyridine (0.696 ml, 8.61 mmol) and thionyl chloride (0.530 ml, 8.61 mmol). The mixture was stirred for 30 min at −15° C. The precipitate was collected by filtration and washed with benzene. The THF-benzene solution was concentrated and the residue was dissolved again in benzene. The resulting solution was treated with charcoal. Removal of charcoal on a Celite pad and subsequent benzene evaporation afforded the title compound (4.86 g, 100%); ir (CHCl$_3$) $v_{max}$: 1770 (C=O) and 1525 cm$^{-1}$ (NO$_2$); $^1$Hmr (CDCl$_3$) δ: 8.15, 8.12 (2H, 2d, H-aromatics), 7.70-7.00 (17H, m, H-aromatics), 5.62, 5.02 (1H, 2s, H-2''), 5.27 (2H, s, CH$_2$-PNB), 4.7 (1H, d, H-4), 4.7-3.7 (m, O—CH$_2$—O, H-1'), 3.5-2.8 (m, H-3), 3.12, 3.08 (3H, 2s, O—CH$_3$), and 1.30-0.96 ppm (3H, m, CH$_3$).

GG. Preparation of (1'R,3S,4R and 1'S,3R,4S) 3-(1'-Acetoxy-1'-ethyl)-1-(paranitrobenzyl 2''-chloro-2''-acetate)-4-tritylthio-2-azetidinone

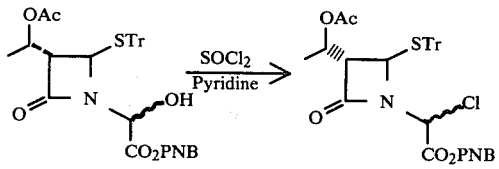

"Isomer B"

A THF (distilled over LAH) solution of (1'R,3S,4R and 1'S, 3R,4S) 3-(1'-acetoxy-1'-ethyl)-1-(paranitrobenzyl-2''-hydroxy-2''-acetate)-4-tritylthio-2-azetidinone (from 10.88 g of N—H) was treated at −15° C. (ice-methanol bath) under nitrogen atmosphere with pyridine (2.19 g, 2.24 ml, 27.7 mmol) and thionyl chloride (3.3 g, 2.02 ml, 27.7 mmol) and thionyl chloride (3.3 g, 2.02 ml, 27.7 mmol). The mixture was stirred for 20 min at −15°. The salt was filtered off and washed with benzene. Solvent (THF+benzene) evaporation afforded a residue which was taken up in benzene (warm) and treated with charcoal. The suspension was filtered through a celite pad and solvent evaporation left a foam; ir (CH$_2$Cl$_2$) $v_{max}$: 1780, 1740 cm$^{-1}$ (C=O) $^1$Hmr (CDCl$_3$) δ: 8.17, 8.21 (2H, 2d, J=8, Ho aromatic) 7.76-6.88 (17H, m, H-aromatic), 5.31, 5.16, 5.12, 4.73 (3H, 4s, CH$_2$-PNB, CHCl), 5.12-4.55 (1H, m, H-1'), 4.35-4.25 (1H, m, H-4), 3.80-3.45 (1H, m, H-3) 1.90 (3H, s, CH$_3$CO), 1.12 1.07 (3H, J=6.5, CH$_3$).

HH. 3-(1'-Paranitrobenzyldioxycarbonyl-1'-ethyl)-1-(paranitrobenzyl 2''-chloro-2''-acetate)-4-tritylthio-2-azetidinones (mixture of epimers at C2'').

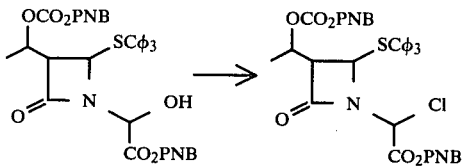

"Isomer C"

Pyridine (58 mg, 0.73 mmol) was added dropwise to a solution of "Isomer C" of 3-(1'-paranitrobenzyldioxycarbonyl-1'-ethyl)-1-(paranitrobenzyl 2''-hydroxy-2''-acetate)-3-tritylthio-2-azetidinones (470 mg, 0.6 mmol; mixture of epimers at C-2'') in THF (15 ml) cooled to −15''C. Immediately after thionyl chloride (86.5 mg, 0.73 mmol) was added dropwise and the mixture was stirred at −15° C. for 0.5 h. The precipitate was removed by filtration and washed with benzene. The combined filtrates were concentrated, the residue dissolved in fresh benzene and the solution treated with activated charcoal, filtered and concentrated to leave the title compound as an oil. 530 mg; 100%. $^1$Hmr (CDCl$_3$) δ: 8.7-6.8 (23H, m, aromatic), 5.53 (1H, s, H-2''), 5.30 and 5.17 (4H, 2s, benzyls), 4.52 (1H, d, J=2, H-4), 4.20-3.70 (1H, m, H-1'), 3.31 (1H, dd, H-3), 1.27 and 1.21 ppm (3H, 2d, J=6.5); ir (CHCl$_3$) $v_{max}$: 1780, 1750 (C=O) and 1525 cm$^{-1}$ (NO$_2$).

"Isomer B"

"Isomer B" of 3-(1-paranitrobenzyldioxycarbonyl-1'-ethyl)-1-(paranitrobenzyl 2''-chloro-2''-acetate)-4-tritylthio-2-azetidinones (mixture of C-2'' epimers) was prepared as described above for the "Isomer C" in quantitative yield. $^1$Hmr (CDCl$_3$) δ: 8.25-6.90 (23H, m, aromatics), 5.40-5.0 (4H, m, benzyls), 5.40-4.45 (1H, m, H-1'), 4.82 and 4.57 (1H, 2s, H-2''), 4.36 and 4.31 (1H, 2d, J=2.5, H-4), 3.63 (1H, m, J=2.5, J=6.5, H-3), 1.25 and 1.18 ppm (3H, 2d, J=6.5, CH$_3$); ir (CHCl$_3$) $_{max}$: 1780, 1750 (C=O), and 1525 cm$^{-1}$ (NO$_2$).

"Isomer A"

"Isomer A" of 3-(1'-paranitrobenzyldioxycarbonyl-1'-ethyl)-1'-(paranitrobenzyl 2''-chloro-2''-acetate)-4-tritylthio-2-azetidinones (mixture of C-2'' epimers). $^1$Hmr (CDCl$_3$) δ: 8.30-6.80 (23H, m, aromatics), 5.45-4.80 (1H, m, H-1'), 5.18 and 5.21 (4H, 2s, benzyls), 4.87 (1H, 2d, H-4), 4.22 and 3.87 (1H, 2s, H-2''), 4.05-3.40 (1H, m, H-3), 1.57 and 1.50 ppm (3H, 2d, CH$_3$).

"Isomer D"

"Isomer D" of 3-(1'''-paranitrobenzyldioxycarbonyl-1'-ethyl-1'-(paranitrobenzyl 2''-chloro-2''-acetate)-4-tritylthio-2-azetidinones (mixture of C-2'' epimers). $^1$Hmr (CDCl$_3$) δ: 8.30-6.70 (23H, m, aromatics), 5.32-5.10 (4H, m, benzyls), 5.48 and 5.30 (1H, 2s, H-2''), 4.82 (1H, d, J=5, H-4), 5.30-5.20 (1H, m, H-1'), 3.15 (1H, m, H-3), 1.40 and 1.30 ppm (3H, 2d, J=6.5, CH$_3$); ir CHCl$_3$) $v_{max}$: 1780, 1750 (C=O) and 1525 cm$^{-1}$ (NO$_2$)

II. Preparation of (1'S,3S,4R and 1'R,3R,4S)3-(1'-Methanesulfonyloxy-1'-ethyl)-1-(paranitrobenzyl 2''-chloro-2''-acetate(-4-tritylthio-2-azetidinone (isomer C) (epimers at C₂'').

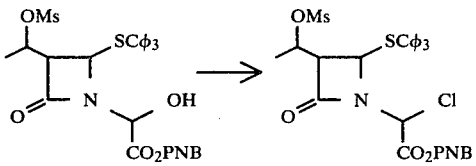

To a cold solution (5° C.) of (1'S,3S,4R and 1'R,3R,4S)3-(1'-methanesulfonyloxy-1'-ethyl)-1-(paranitrobenzyl 2''-hydroxy-2''-acetate)-4-tritylthio-2-azetidinone (24.0 g, 35.5 mmol) in dry tetrahydrofuran (350 ml) was added pyridine (3.65 g, 46.2 mmol) and thionyl chloride (5.5 g, 46.2 mmol) dropwise. After stirring for 45 min, ether (100 ml) was added to precipitate the hydrochloride salt which was filtered off. The filtrate was evaporated and the residue redissolved in benzene (200 ml) and treated with charcoal. Evaporation of the solvent left a nearly white foam which was used as such in the next step. ¹Hmr (CDCl₃) δ: 8.18 (2H, d, J=9, Hm aromatic), 7.72 (17H, m, part of d, Ho aromatic, trityl), 5.57 and 5.12 (1H, s, H-2''), 5.28 (2H, s, —CH₂PNB), 4.73 (1H, 2d, H-4), 3.21 (1H, 2dq, H-3), 2.78 (3H, 2s, mesylate and 1.21 ppm (3H, 2d, H-6H₂; H-2'); ir $\nu_{max}$ 1779 cm⁻¹ (C=O)

JJ. Preparation of (1'S,3R,4R and 1'R,3S,4S) 3-(1'-Methoxymethoxy-1'-ethyl)-1-(paranitrobenzyl 2''-triphenylphosphoranylidene-2''-acetate)-4-tritylthio-2-azetidinone (Isomer A)

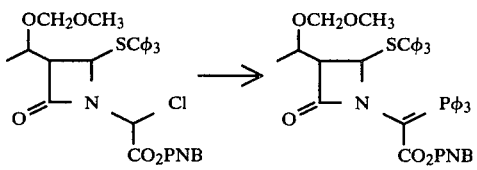

A mixture of Isomer A of 3-(1'-methoxymethoxy-1'-ethyl)-1-(paranitrobenzyl-2''-chloro-2''-acetate)-4-tritylthio-2-azetidinone (6.6 g, 10 mmol), triphenylphosphine (3.3 g, 12.5 mmol), 2,6-lutidine (1.3 ml, 11 mmol) and dioxane (140 ml) was heated under reflux for 2 days. The solution was diluted with ether, washed with dilute acid (5% HCl), water, dilute sodium bicarbonate solution and brine, dried and concentrated. The residue was purified by chromatography on silica gel eluting with 10% ether in benzene. Concentration of the pertinent fractions left the title compound as a foam (1.4 g, 13.7%) ir (KBr) $\nu_{max}$: 1750 (C=O) and 1660–1650 cm⁻¹ (C=C, aromatics).

KK. Preparation of (1'S,3S,4R and 1'R,3R,4S) 3-(1'-Methoxymethyloxy-1'-ethyl)-1-(paranitrobenzyl 2''-triphenylphosphoranylidene-2''-acetate)-4-tritylthio-2-azetidinone (Isomer C).

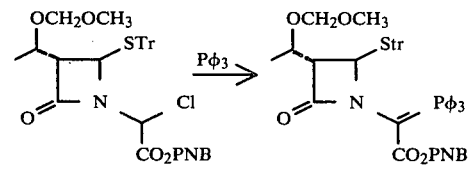

A dioxane (100 ml, distilled over LAH) solution of (1'S, 3S,4R and 1'R,3R,4S) 3-(1'-methoxymethyloxy-1'-ethyl)-1-(paranitrobenzyl-2''-chloro-2''-acetate)-4-tritylthio-2-azetidinone (4.86 g, 6.62 mmol), triphenylphosphine (2.60 g, 9.93 mmol) and 2,6-lutidine (770 mg, 0.837 ml, 7.20 mmol) was heated under reflux for 4 h and kept in a hot bath (100° C.) for 16 h. The mixture was diluted with ether, washed with 1% aqueous HCl, water, 10% aqueous NaHCO₃, water and brine and dried (MgSO₄). The solution was concentrated and the residue filtered through a silica gel (65 g) column (5%, 10% and 20% ether-benzene) to give the title compound (2.8 g, 48%). ir (CHCl₃) $\nu_{max}$: 1795 (C=O), 1620 and 1605 (phosphorane) and 1515 cm⁻¹ (NO₂).

LL. (1'R,3S,4R and 1'S,3R,4S) 3-(1'-Acetoxy-1'-ethyl)-1-(paranitrobenzyl-2''-triphenylphosphoranylidene-2''-acetate)-4-tritylthio-2-azeditinone (Isomer B)

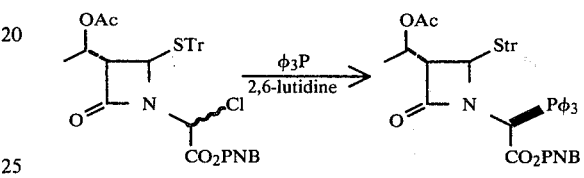

A dioxane (100 ml, freshly distilled over LAH) solution of crude (1'R,3S,4R and 1'S,3R,4S) 3-(1'-acetoxy-1'-ethyl)-1-(paranitroresidue which was passed through a silica gel (10 times its weight) column (10% ether-benzene, ether, and ethyl acetate). The title compound was obtained as a crystalline solid (3.1 g, 49%), mp 189°–190° (ether); ir (CHCl₃) $\nu_{max}$: 1750 (C=O), 1620, 1605 (phosphorane) and 1522 cm⁻¹ (NO₂).

ISOMER C

Isomer C of 3-(1'-paranitrobenzyldioxycarbonyl-1'-ethyl)-1-(paranitrobenzyl-2''-triphenylphosphoranylidene-2''-acetate)-4-tritylthio-2-azetidinone was prepared as described above for isomer B. ir (CHCl₃) $\nu_{max}$: 1750 (C=O), 1610, 1620 (phosphorane) and 1520 cm⁻¹ (NO₂); ¹Hmr (CDCl₃) δ: 8.6=6.7 (H, aromatics), 5.22 and 4.95 (benzyls), 4.70 (H-4), 2.6 (H-3), 1.19 and 1.07 ppm (CH₃).

ISOMER D

A mixture of Isomer D of 3-(1'-p-nitrobenzyldioxycarbonyl-1'-ethyl)-1-(p-nitrobenzyl 2''-chloro-2''-acetate)-4-tritylthio-2-azetidinone (4.598 g, 4.45 mmol; purity 77%, mixture of epimers at C-2''), triphenylphosphine (1.425 g, 5.44 mmol; Aldrich) and 2,6-lutidine (0.63 ml, 580 mg, 5.40 mmol; Anachemia) in dioxane (65 ml; distilled from LAH) was heated at gentle reflux under N₂ and 41 h, monitoring the reaction by tlc (benzene:ether=3:1). The dark reaction mixture was cooled, diluted with EtOAc and washed successively with 0.1 NHCl, water, 2% NaHCO₃ and then brine. Drying (Na₂SO₄) and evaporation of the solvents gave 4.18 g of a dark coloured oil which was purified by column chromatography (SiO₂, 88 g; eluent 10–25% ether in benzene), yielding 1.108 g (1.08 mmole, yield 24.3%) of the title compound as a yellowish foam: ¹Hmr (CDCl₃) δ: 1.08 (d, J=6 Hz, 1'-CH₃); ir (neat) $\nu_{max}$: 1745 cm⁻¹ (s, C=O). benzyl 2''-chloro-2''-acetate)-4-tritylthio-2-azetidinone was treated with 2,6-lutidine (2.97 g, 3.23 ml, 27.72 mmol) and triphenyl phosphine (9.91 g, 37.8 mmol). The mixture was refluxed (oil bath 130°) for 18 h. The solvent was evaporated and the residue was redissolved in methylene chloride. The resulting solution was successively washed with diluted HCl, H₂O, diluted aqueous NaHCO₃, H₂O and brine. Drying and solvent evaporation left the title compound as a solid which was triturated with ether and collected by filtration (14.6 g, 65.9%); ir (CH₂Cl₂) $v_{max}$: 1750 (C=O) and 1620, 1610 cm⁻¹ (phosphorane).

MM. 3-(1'-Paranitrobenzyldioxycarbonyl-1'-ethyl)-1-(paranitrobenzyl-2"-triphenylphosphoranylidene-2"-acetate)-4-tritylthio-2-azetidinone.

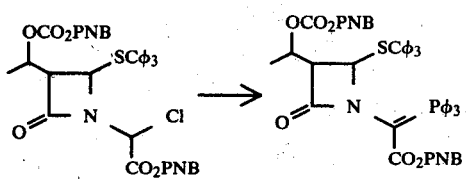

Isomer B

A mixture of (1'R,3S,4R and 1'S,3R,4S) 3-(1'-paranitrobenzyl-dioxycarbonyl-1'-ethyl)-1-(paranitrobenzyl-2"-chloro-2"-acetate)-4-tritylthioazetidinone (isomer B) (4.96 g, 6.22 mmol, mixture of epimers at C-2"), triphenyl phosphine (2.47 g, 9.42 mmol) and 2,6-lutidine (740 mg, 0.80 ml, 6.91 mmol) was refluxed in dioxane (freshly distilled over LAH) for 30 h. The solution was diluted with ether and ethyl acetate, washed with 5% aqueous HCl, water, 10% aqueous NaHCO₃, water and brine and dried (MgSO₄). Solvent evaporation afforded a NN. Preparation of (1'S,3S,4R and 1'R,3R,4S)3-(1'-Methanesulfonyloxy-1'-ethyl)-1-(pananitrobenzyl 2"-triphenylphosphoranylidene-2"-acetate)-4-tritylthio-2-azetidinone (isomer C)

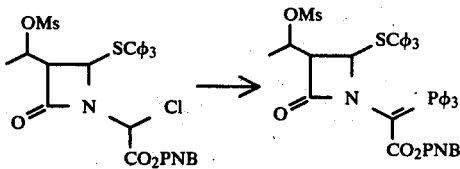

A solution of (1'S,3S,4R and 1'R,3R,4S)3-(1'-methanesulfonyloxy-1'-ethyl)-1-(paranitrobenzyl 2"-chloro-2"-acetate)-4-tritylthio-2-azetidinone (24.7 g, 35.5 mmol), triphenylphosphine (11.2 g, 42.7 mmol) and 2.6-lutidine (4.2 g, 39.1 mmol) in dry dioxane (350 ml) was refluxed under nitrogen for 19 h. The solvent was evaporated and the crude product redissolved in ethyl acetate and washed successively with dilute HCl, NaHCO₃ and brine. Purification was completed by chromatography on a silica gel column (8.5×12 cm). Elution with 10% ether-dichloromethane (1.5 l) and then ether (1.5 l) gave the purified phosphorane; 12.36 g (40%). ¹Hmr (CDCl₃) δ: 2.53 and 2.93 ppm (3H, 2s, mesylate); ir $v_{max}$: 1749 and 1620 cm⁻¹ (C=O)

OO. Preparation of (1'R,3S,4R and 1'S,3R,4S) 3-(1'-Hydroxy-1'-ethyl)-1-(paranitrobenzyl-2"-triphenylphosphoranylidene-2"-acetate) 4-tritylthio-2-azetidinone (Isomer B).

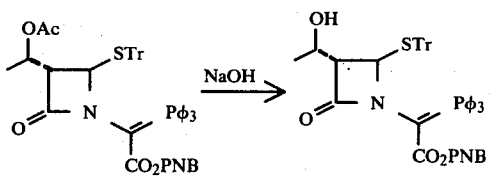

A solution of phosphorane (1'R,3S,4R and 1'S,3R,4S) 3-(1'-acetoxy-1'-ethyl)-1-(paranitrobenzyl 2"-triphenylphosphoranylidene-2"-acetate)-4-tritylthio-2-azetidinone (4.43 g, 5.00 mmol) in methanol (10 ml) THF (60 ml) was treated at room temperature with 1% aqueous NaOH (1 eq, 200 mg in 20 ml H₂O). The reaction progression was followed by tlc*. The mixture was diluted with ether-ethyl acetate and washed with HCl, H₂O, aqueous NaHCO₃, H₂O and brine. Solvent evaporation afforded a residue which was crystallized from benzene-ether (3.7 g, 87.7%) mp 169.5°-170.5° C. ir (CH₂Cl₂) $v_{max}$: 1745 (C=O) and 1620 cm⁻¹ (phosphorane).

*Heating the mixture increased the reaction rate.

PP. Preparation of (1'S,3R,4R and 1'R,3S,4S) Silver 3-(1'-methoxymethyl-1'-ethyl)-1-(paranitrobenzyl 2"-triphenylphosphoranylidene-2"-acetate)-2-azetidinone-4-thiolate (Isomer A)

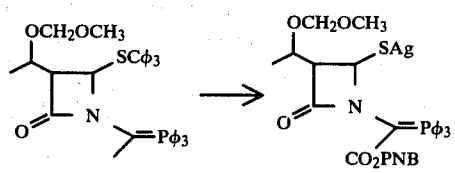

Silver 3-(1'-methoxymethyl-1'-ethyl)-1-(paranitrobenzyl-2"-triphenylphosphoranylidene-2"-acetate)-3-tritylthio-2-azetidinone (isomer A), was prepared as described elsewhere for the isomer C of the paranitrobenzyldioxy carbonyl derivative. Yield 50%. ir (neat $v_{max}$: 1745 cm⁻¹ (C=O).

QQ. Preparation of 1'S,3S,4R and 1'R,3R,4S) Silver 2-(1'-methoxymethyloxy-1'-ethyl)-1-(paranitrobenzyl 2"-triphenylphosphoranylidene-2"-acetate)-2-azetidinone-4-thiolate (Isomer C)

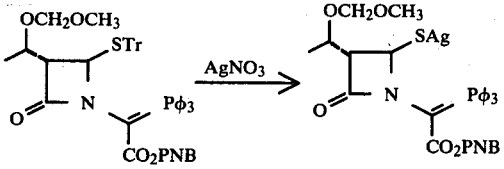

(1'S,3S,4R and 1'R,3R,4S) 3-(1'-methoxymethyloxy-1'-ethyl)-1-(paranitrobenzyl 2"-triphenylphosphoranylidene-2"-acetate)-4-tritylthio-2-azetidinone (887 mg, 1.0 mmol) was first dissolved in hot (40° C.) methanol (30 ml), treated with pyridine (103 mg, 0.105 ml, 1.3 mmol) and, after cooling, was treated with a 0.15 M methanol solution of silver nitrate (8.7 ml, 1.3 mmol). The mixture was stirred for 1 h at 23° C., cooled (ice bath) and stirred for 20 min. The salt was filtered and washed successively with cold methanol and ether (3 times, 671 mg, 87%). ir (CHCl₃) $v_{max}$: 1745 (C=O), 1605 (phosphorane) and 1520 cm⁻¹ (NO₂).

RR. Preparation of Silver 3-(1'-paranitrobenzyldioxycarbonyl-1'-ethyl)-1-(paranitrobenzyl 2"-triphenylphosphoranylidene-2"-acetate)-2-azetidinone-4-thiolate

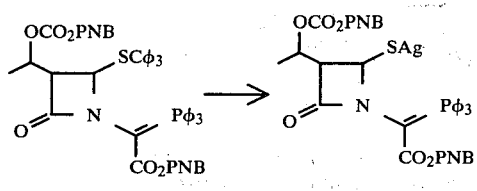

"Isomer B"

(1,'R,3S,4R and 1'S,3R,4S) 3-(1'-paranitrobenzylcarbonyldioxy-1'-ethyl)-1-(paranitrobenzyl-2"-triphenylphosphoranylidene-2"-acetate)-4-trithio-2-azetidinone (1.02 g, 1 mmol) was first dissolved in CH$_2$Cl$_2$ (3 ml) and diluted with hot (55° C.) MeOH (20 ml). The hot solution was treated first with pyridine (120 ml, 117 mg, 1.48 mmol) and a hot (55° C.) 0.15 M methanolic solution of silver nitrate (8 ml, 1.2 mmol). The mixture was stirred at room temperature for 15 min, then at 0° C. for 2 h. It was then concentrated to a 10% solution on the rotary evaporator (no bath). The mercaptide was filtered and washed twice with cold (−15° C.) methanol and three times with ether. (917 mg, 100%). ir (nujol mull) $\nu_{max}$: 1745 (C=O), 1600 (phosphorane) and 1517 cm$^{-1}$ (NO$_2$).

"Isomer C"

Silver 3-(1'-paranitrobenzyldioxycarbonyl-1'-ethyl)-1-(paranitrobenzyl 2"-triphenylphosphoranylidene-2"-triphenylphosphoranylidene-2"-acetate)-2-azetidinone-4-thiolate, "Isomer C", was prepared as described above for the "Isomer B"; ir (nujol) $\nu_{max}$: 1745 (C=O) and 1600 cm$^{-1}$ (phosphorane).

· "Isomer D"

A solution of Isomer D of 3-(1'-p-nitrobenzylcarbonyldioxy-1'-ethyl)-1-(p-nitrobenzyl 2"-triphenylphosphoranylidene-2"-acetate)-4-tritylthio-2-azetidinone (145 mg, 0.142 mmol) was prepared by first dissolving it in CH$_2$Cl$_2$ (5 ml), removing the CH$_2$Cl$_2$ at 55°-60° and adding hot MeOH (4 ml). To the above solution was added a hot solution of AgNO$_3$ in MeOH (0.15 M, 1.14 ml, 0.17 mmol, 1.2 eq), followed by pyridine (14 μl, 0.17 mmol, 1.2 eq). The silver mercaptide started to precipitate immediately. The mixture was stirred 2 h at room temperature and 1 h at 0°. The mercaptide was collected by filtration and washed with ice-cold MeOH and ether, yielding 99 mg (0.11 mmol, 78%) of the title compound as a brownish solid: ir (Nujol) $\nu_{max}$: 1750 cm$^{-1}$ (s, C=O).

SS. Preparation of (1'R,3S,4R and 1'S,3R,4S) Silver 3-(1'-hydroxy-1'-ethyl)-1-)paranitrobenzyl-2"-triphenylphosphoranylidene-2"-acetate)-2-azetidinone-4-thiolate (Isomer B)

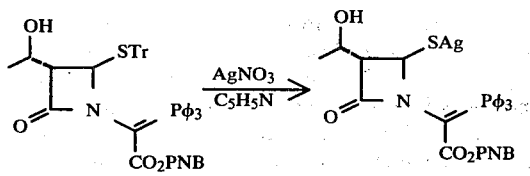

A solution* of (1'R,3S,4R and 1'S,3R,4S) 3-(1'-hydroxy-1'-ethyl)-1-(paranitrobenzyl-2"-triphenylphosphoranylidene-2"-acetate)-4-tritylthio-2-azetidinone (1 g, 1.19 mmol) in MeOH (10 ml), was treated with pyridine (124 μl, 121.3 mg, 1.53 mmol) and at 10° C. with a 0.15 M solution of silver nitrate in MeOH (15 ml, 2.25 mmol—or until no more precipitation of the silver mercaptide occurred). The mixture was stirred for 1 h and concentrated on the rotary evaporator (no bath) to approximately 10% concentration. The solvent was filtered off. The cake was washed once with MeOH and 3 times with ether, and pumped under high vacuum (954 mg, 100%). ir (Nujol mull) $\nu_{max}$: 3500–3400 (O—H), 1752 (C=O) 1595 (phosphorane) and 1525 cm$^{-1}$ (NO$_2$)

*The crystalline material was first dissolved in CH$_2$Cl$_2$. with water and the white solid was filtered and dried over P$_2$O$_5$ under high vacuum for 5 h, 84 mg, 40%; $^1$Hmr (D$_2$O) δ: 1.34 (d, $J_{H-2''-H-1''}$=6.3 Hz, 3H, H-2"-, 2.3–2.7 (m, 4H, H-2', H-4'), 3.90 (dd, $J_{H-6-H-5}$=1.5 Hz, $J_{H-6-H-1''}$=6.1 Hz, 1H, H-6) and 5.68 (d, $J_{H-5-H-6}$=1.5 Hz, 1H, H-5); uv (H$_2$O, 23° C.) $\lambda_{max}$: 258 (ε 4738) and 306 (ε 6318). The filtrate was purified by hplc, 58 mg; uv (H$_2$O, 23° C.) $\lambda_{max}$: 257 (ε 3580) and 306 (ε 5033).

EXAMPLE 6

(1'R,5R,6S and 1'S,5S,6R) 6-(1'-Hydroxyethyl)-2-(2-aminoethoxymethyl)penem-3-carboxylic Acid (isomer B)

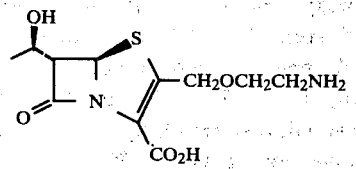

(1'R,3S,4R and 1'S,3R,4S) 4-(2-Azidoethoxy)acetylthio-3-(1'-hydroxyethyl)-1-(p-nitrobenzyl 2"-triphenylphosphoranylidene-2"-acetate)-2-azetidinone (Isomer B)

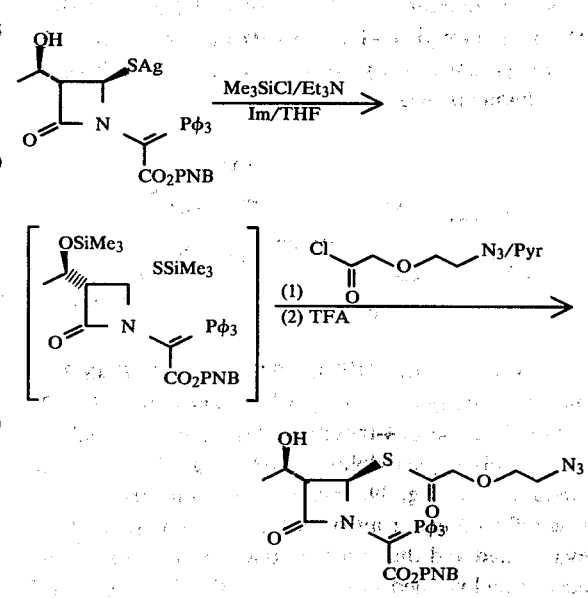

To a stirred solution of (1'R,3S,4R and 1'S,3R,4S) silver 3-(1'-hydroxyethyl)-1-(p-nitrobenzyl 2"-triphenylphosphoranylidene-2"-acetate)-2-azetidinone-4-thiolate (Isomer B) (820 mg, 1.16 mmol) in THF (20 ml) was added at −15° (MeOH-ice bath) under N$_2$ atmosphere successively triethylamine (01648 ml, 4.66 mmol, 4.02 eq), chlorotrimethyl silane (0.589 ml, 4.64 mmol, 4.00 eq) and imidazole (81.2 mg, 1.12 mmol). The mixture was stirred at room temperature for 18 h (overnight) and then cooled to −10°∼−15°. To this was added pyridine (0.220 ml, 2.72 mmol) and then a solution of 2-azidoethoxyacetyl chloride (372 mg, 2.27 mmol, 1.96 eq) in CH$_2$Cl$_2$ (20 ml). It was stirred at room temperature for 1 h. After filtration of the precipitate, the filtrate, diluted with EtOAc, was washed successively with 1 N HCl, brine, saturated NaHCO$_3$ and brine, dried (Na$_2$SO$_4$) and evaporated yielding 748 mg an oil. This oil dissolved in wet CH$_2$Cl$_2$ (20 ml with 3 drops of water) was treated with trifluoroacetic acid (2 drops) at room temperature for 30 min. The mixture was washed with saturated NaHCO$_3$ and then brine, dried (Na$_2$SO$_4$) and evaporated yielding 695 mg of a crude oil. This oil was purified by column chromatography (SiO$_2$ 15 g, eluent EtOAc: CH$_2$Cl$_2$=1:1) collecting 538 mg (0.739 mmol, yield 63.7%) of the title compound as a yellowish oil: $^1$Hmr (CDCl$_3$) δ: 1.22 (d, J=6 Hz, CH$_3$-1'), 5.6 (2d, H-4) and 7.3=8.4 ppm (aromatic Hs); ir (neat) ν$_{max}$: 3420 (OH), 2100 (—N$_3$), 1750 (C=O) and 1690 cm$^{-1}$ (thioester); Rf 0.20 (CH$_2$Cl$_2$:EtOAc=1:1).

(1'R,5R,6S and 1'S,5S,6R) p-Nitrobenzyl 6-(1'-hydroxyethyl)-2-(2-azidoethoxymethyl)penem-3-carboxylate (Isomer B)

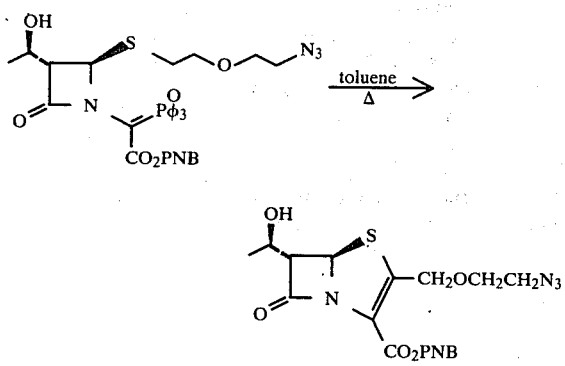

A solution of (1'R,3S,4R and 1'S,3R,4S) 4-(2-azidoethoxy)acetylthio-3-(1'-hydroxyethyl)-1-(p-nitrobenzyl 2''-triphenylphosphoranylidene-2''-acetate)-2-azetidinone, (Isomer B) (490 mg, 0.673 mmol) in toluene (80 ml) was heated at gentle reflux for 3 h. Evaporation of the solvent in vacuo gave an oily residue which was purified by column chromatography (SiO$_2$, 10 g; eluent 5-10% EtOAc in CH$_2$Cl$_2$) followed by crystallization from CH$_2$Cl$_2$-ether to obtain 202 mg (0.449 mmol, yield 66.8%) of the title compound as light yellow crystals: $^1$Hmr (CDCl$_3$) δ: 1.35 (3H, d, J=6.5 Hz, CH$_3$-1'), 2.18 (1H, br, OH), 3.2-3.9 (5H, m, —CH$_2$— and H-6), 3.9-4.5 (1H, m, H-1'), 4.45-4.72-4.75-5.02 (2H, AB type, CH$_2$—2), 5.02-5.25-5.35-5.57 (2H, AB type, —CH$_2$Ar), 5.62 (1H, d, J=1 Hz, H-5) and 7.42-7.65-8.13-8.28 ppm (4H, A$_2$'B$_2$', aromatic Hs); ir (nujol) ν$_{max}$: 3460 (—OH), 2110 (—N$_3$), 1765 (β-lactam) and 1680 cm$^{-1}$ (ester). An analytical sample was obtained by further crystallization: mp 107°-8° C. (CH$_2$Cl$_2$-ether uv (EtOH) λ$_{max}$: 264 (ε 12000) and 323 mμ (ε 9200); Rf 962 (CH$_2$Cl$_2$:EtOAc=1:1); Anal.calcd for C$_{18}$H$_{19}$N$_5$O$_7$S: C 48.10, H 4.26, N 15.88, S 7.13; found: C 47.81, H 4.18, N 15.00, S 7.16

(1'R,5R,6S abd 1'S,5S,6R) 6-1'-hydroxyethyl)-2-(2-azidoethoxymethyl)penem-3-carboxylic acid (Isomer B)

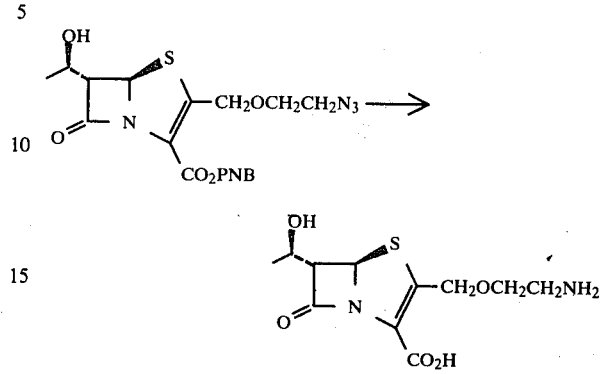

A solution of (1'R,5R,6S and 1'S,5S,6R) p-nitrobenzyl 6-(1'-hydroxyethyl)-2-(2-azidoethoxymethyl)-penem-3-carboxylate (Isomer B) (180 mg, 0.400 mmol) in THF (18 ml) was mixed with ether (19 ml), H$_2$O (18 ml) and 10% Pd-C (180 mg). It was hydrogenated (H$_2$, 55 psi) at room temperature for 2.5 h. After filtering off the catalyst the aqueous filtrate was washed with EtOAc and lyophilized to yield 84.4 mg (0.293 mmol, crude yield 73.2%) of the title compound as a crude yellowish powder: uv (H$_2$O) λ$_{max}$: 305.5 (ε 4800) and 255 mμ (ε 3800). This powder was purified by hplc (Waters C$_{18}$ Micro Bondapack Reverse Phase 30 cm×10 mm; eluent 1% CH$_3$CN in H$_2$O) to give 44.7 mg (0.155 mmol, yield 38.8%) of the title compound as white powder: $^1$Hmr (D$_2$O) δ: 1.34 (3H, d, J=6.4 Hz, CH$_3$-1'), 3.26 (2H, m, —CH$_2$N), 3.82 (2H, m, —OCH$_2$CH$_2$—), 3.94 (1H, dd, J$_{6-1'}$=6.2 Hz, J$_{6-5}$=1.4 Hz, H-6), 4.2-4.4 (1H, m, H-1'), 4.52-4.60-4.84-5.02 (2H, AB type, CH$_2$—2) and 5.71 ppm (1H, d, J=1.3 Hz, H-5); ir (KBr disc) ν$_{max}$: 3420 (OH), 3000-2600 (br, CO$_2$H), 1765 (β-lactam) and 1575 cm$^{-1}$ (—CO$_2$H); uv (H$_2$O) λ$_{max}$: 306 (ε 5300) and 258 mμ (ε 3600).

EXAMPLE 7

2-(2-Aminoethoxymethyl)penem-3-carboxylic Acid (via mercaptide intermediate)

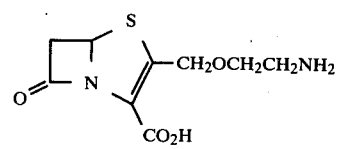

Ethyl 2-chloroethoxyacetate

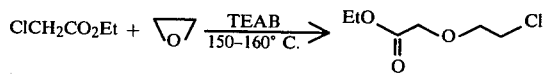

A mixture of ethyl chloroacetate (24.5 g, 0.200 mol), ethyleneoxide (8.80 g, 0.300 mol) and tetraethylammonium bromide (0.40 g, 1.9 mmol; dried in vacuo) was heated in a bomb at 150°-160° C. for 6 h. After cooling, the reaction mixture was distilled under reduced pressure collecting 6.66 g (54.4 mmol, 27.2%) of ethyl chloroacetate, bp 22°-24° C. (0.5 mmHg) and 8.39 g (50.4 mmol, 25.2%) of ethyl 2-chloroethoxyacetate as a colourless oil; bp 49°–53° C. (0.1 mmhg); $^1$Hmr (CDCl$_3$) δ: 1.28 (3H, t, J=7 Hz, —CH$_3$), 3.5–4.0 (4H, m, A$_2$B$_2$, —CH$_2$CH$_2$—Cl), 4.15 (2H, s, —COCH$_2$O—), 4.25 ppm (2H, q, J=7 Hz, —OCH$_2$CH$_3$); ir (neat) $\nu_{max}$: 1740 cm$^{-1}$ (C=O ester). Procedure of D. Klamann et al., Jastus Liebig Ann., 710, 59 (1967) (Reported: yield 42%, bp 55.5°/0.35 mmHg).

Ethyl 2-azidoethoxyacetate

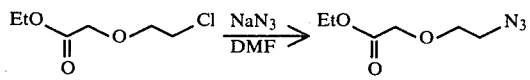

A mixture of ethyl 2-chloroethoxyacetate (7.71 g, 36.3 mmol) and sodium azide (3.31 g, 50.9 mmol) in DMF (100 ml) was heated at 80°–90° C. for 3.5 h by which time tlc (hexane; ether 1:1) indicated that the reaction was complete. The cooled mixture was poured into H$_2$O (1 l) and extracted with ether (250 ml×3). The extracts washed with H$_2$O (×2) and brine (×1) were dried (MgSO$_4$) and evaporated yielding 7.16 g (41.4 mmol 89.4%) of ethyl 2-azidoethoxyacetate as a yellowish oil: $^1$Hmr (CDCl$_3$) δ: 1.30 (3H, t, J=7 Hz, —OCH$_2$CH$_3$), 3.3–4.0 (4H, m, —OCH$_2$ CH$_2$N$_3$), 4.13 (2H, s, —COCH$_2$O—), 4.23 ppm (2H, q, J=7 Hz, —OCH$_2$CH$_3$); ir (neat) $\nu_{max}$: 2100 (N$_3$) and 1750 cm$^{-1}$ (C=O ester). This material was used in the next step without further purification.

2-Azidoethoxyacetic acid

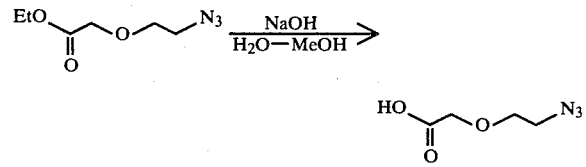

To a solution of ethyl 2-azidoethoxyacetate (6.56 g, 37.9 mmol) in MeOH (80 ml) was added 1 N aq. NaOH (80 ml) and the mixture was stirred at room temperature overnight (17 h). After removing the insoluble material, the methanol was evaporated in vacuo and this was saturated with sodium chloride and washed with ether (30 ml×3). The aqueous layer acidified with 3 N HCl (30 ml) was extracted with ether (40 ml×4). The ether extracts were washed with brine, dried (MgSO$_4$) and evaporated to yield 4.25 g (29.3 mmol, 77.3%) of 2-azidoethoxyacetic acid as a colourless oil: $^1$Hmr (CDCl$_3$) δ: 3.3–4.0 (4H, m, —OCH$_2$CH$_2$N$_3$), 4.22 (2H, s, —COCH$_2$O—), 9.52 ppm (1H, s, —CO$_2$H, exchanged with D$_2$O); ir (neat) $\nu_{max}$: 2600–3300 (br, —CO$_2$H) 2100 (azide) and 1740 cm$^{-1}$ C=O—CO$_2$H). This material was used in the next step without further purification.

2-Azidoethoxyacetyl chloride

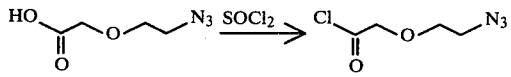

A solution of 2-azidoethoxyacetic acid (2.09 g, 14.4 mmol) in thionyl chloride (5 ml) was stirred at room temperature for 4 h. The excess thionyl chloride was removed under the vacuum of the water aspirator and the residue dissolved in benzene (10 ml, dried over molecular sieves) was evaporated in vacuo. The oil so obtained was dried in vacuo (water pump) over NaOH for 1 h yielding 2.23 g (13.6 mmol, 94.4%) of 2-azidoethoxyacetyl chloride as a colourless oil: $^1$Hmr (CDCl$_3$) δ: 3.43 (2H, br. t, J=5 Hz, —CH$_2$O—) 3.78 (2H, br. t, J=5 Hz, —CH$_2$N$_3$) and 4.50 ppm (2H, s, —COCH$_2$O—); ir (neat) $\nu_{max}$: 2100 (azide) and 1800 cm$^{-1}$ (—COCl). This material was used in the next reaction without any purification.

4-(2'-azidoethoxyacetylthio)-1-(paranitrobenzyl 2''-triphenylphosphoranylidene-2''-acetate)-2-azetidinone

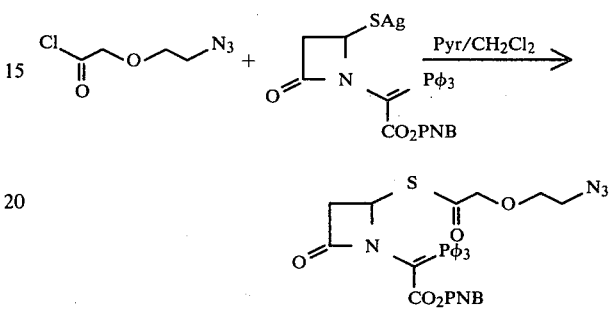

To a stirred solution of silver 1(paranitrobenzyl-2'-triphenylphosphoranylide-2'-acetate)-2-azetidinone-4-thiolate (7.96 g, 12.0 mmol) in CH$_2$Cl$_2$ (100 ml) containing pyridine (1.94 ml, 24.0 mmol) was added at 0°–5° C. under a nitrogen atmosphere a solution of 2-azidoethoxyacetyl chloride (2.23 g, 13.6 mmol) in CH$_2$Cl$_2$ (20 ml) and the mixture was stirred at room temperature for 2 h. After filtration of the precipitate, the filtrate was evaporated and the residual oil was purified by column chromatography (SiO$_2$, 160 g; eluent, EtOAc:CH$_2$Cl$_2$=1:1) collecting 4.216 g (6.17 mmol, 51.4%) of the title phosphorane as a yellowish foam. This foam was used in the next step. An analytical sample was obtained by crystallization from CH$_2$Cl$_2$-ether (1:9): mp 128°–9° C. (dec.); ir (nujol) $\nu_{max}$: 2090 (—N$_3$), 1755 (β-lactam) and 1690 cm$^{-1}$ (thioester); Anal. calcd for C$_{34}$H$_{30}$N$_5$O$_7$PS: C 59.74, H 4.42, N 10.26, S 4.69; found: C 59.33, H 4.49, N 9.69, S 5.19; tlc (EtOAc) Rf=0.55.

p-Nitrobenzyl 2-(2-azidoethoxy)methyl-penem-3-carboxylate

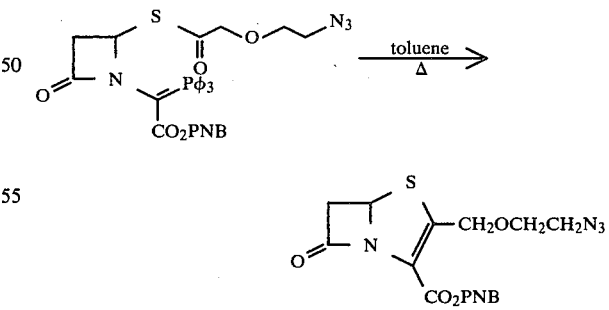

A solution (cloudy) of the above phosphorane (4.13 g, 6.04 mmol) in toluene (200 ml) was heated under reflux under a nitrogen atmosphere for 1.5 h. After removal of the insoluble material, the solvent was evaporated in vacuo and the residual oil was purified by column chromatography (SiO$_2$, 80 g, eluent 5% ether in benzene) collecting 2.44 g (6.02 mmol, 99.6%) of title compound as a yellowish oil. This oil was used in the next step. Crystallization from CH$_2$Cl$_2$-ether (1:9) gave an analytical sample: mp 88°-89.5° C.; $^1$Hmr (CDCl$_3$) δ: 3.35 (2H, t, J=5 Hz, —OCH$_2$—), 3.47 (1H, dd, J$_{gem}$=16 Hz, J$_{trans}$2 Hz, 3.67 (2H, t, J=5 Hz, —CH$_2$N$_3$), 3.65 (1H, dd, J$_{gem}$16 Hz, J$_{cis}$=3.5 Hz, C$_6$-H), 4.73 (2H, ABq, J=16, 19 C$_2$—CH$_2$), 5.30 (2H, ABq, J=13.5, 9, —OCH$_2$Ar), 5.63 (1H, dd, J$_{trans}$=2 Hz, J$_{cis}$=3.5 Hz, C$_5$-H), 7.50-7.63-8.12-8.27 ppm (4H, A$_2'$B$_2'$, aromatic Hs); ir (nujol) ν$_{max}$: 2100 (—N$_3$), 1785 (β-lactam) and 1695 cm$^{-1}$ (ester) uv (EtOH) λ$_{max}$: 263 mμ (ε12000), 320.5 mμ (ε9600) tlc (benzene:ether=1:1) Rf=0.60.

2-(2-Aminoethoxy)methyl-penem-3-carboxylic acid

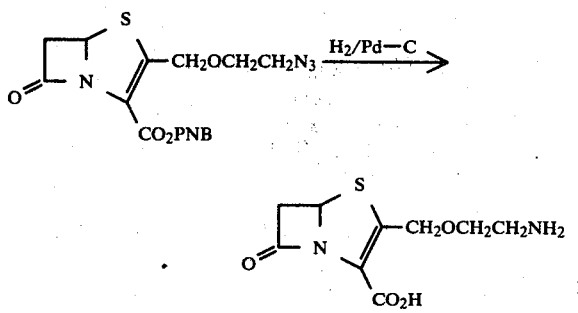

A solution of the above azido ester (1.62 g, 4.00 mmol) in dimethoxyethane (50 ml) was mixed with ether (50 ml), H$_2$O (50 ml) and 10% Pd-C (1.62 g; Engelhard) and hydrogenated at room temperature (H$_2$: 55 psi) for 2.5 h. After filtration of the catalyst, the aqueous layer was washed with ether (50 ml×2) and then EtOAc (50 ml×1). The aqueous solution was lyophilized to give 817 mg (3.34 mmol, 83.6%) of the title amino-acid as a yellowish powder: uv (H$_2$O) λ$_{max}$: 304 mμ (ε5000). This material was purified by hplc (Waters, C$_{18}$ Micro Bondapak Reverse Phase 30 cm×10 mm; eluent 1% CH$_3$CN in H$_2$O) to give 432 mg (1.77 mmol, 44.2%) of the title amino-acid as a white powder: $^1$Hmr (D$_2$O) δ: 3.19-3.9 (4H, m, —OCH$_2$CH$_2$NH$_2$), 3.54 (1H, dd, J$_{gem}$=16.9 Hz, J$_{trans}$=1.9 Hz, C$_6$-H), 3.88 (1H, dd, J$_{gem}$=16.8 Hz, J$_{cis}$=3.7 Hz, C$_6$-H), 4.52-4.70-4.83-5.01 (2H, AB type, C$_2$—CH$_2$O—) and 5.77 ppm (1H, dd, J$_{cis}$=3.6 Hz, J$_{trans}$=1.9 C$_5$-H); ir (KBr disc) ν$_{max}$: 1770 (β-lactam) and 1580 cm$^{-1}$ (—CO$_2$H); uv (H$_2$O) λ$_{max}$: 304 mμ (ε5400), 256 mμ (ε3100).

EXAMPLE 8

2-(2-Aminoethylthiomethyl)penem-3-carboxylic Acid (via mercaptide intermediate)

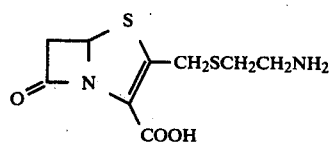

2-Azidoethyl methanesulfonate

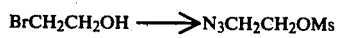

A solution of bromoethanol (7.5 g, 60.0 mmol) and sodium azide (5.0 g, 76.9 mmol) in HMPT (30 ml) was heated at 115° C. for 2.5 h. The reaction mixture was cooled to 23° C. and diluted with CH$_2$Cl$_2$ (100 ml). The solids were removed by filtration and the CH$_2$Cl$_2$ was evaporated on the rotary evaporator leaving a yellow liquid which was cooled to 0° C. and successively treated with mesylchloride (5.57 ml, 72.0 mmol) and triethylamine (10.0 ml, 72.0 mmol). The reaction mixture was stirred at 0° C. for 1 h, then at 23° C. for 6 h, and poured into H$_2$O (300 ml). The aqueous solution was extracted with ether (1×200 ml, 4×100 ml); the ether extracts were combined, washed with 1 N HCl solution, H$_2$O saturated NaHCO$_3$ solution and H$_2$O, dried over anhydrous MgSO$_4$ and concentrated on a rotary evaporator to an orange liquid which was distilled under high vacuum bp 95°-100° C. 0.3 torr, 5.8 g, 58.5%; ir (neat) ν$_{max}$: 2005 (s, N$_3$), 1345 (s, SO$_2$—O), 1175 (m, SO$_2$—O) cm$^{-1}$. $^1$Hmr (CDCl$_3$) δ: 3.03 (s, 3H, OCH$_3$), 3.43-3.76 (m, 2H, H-2) and 4.2-4.46 ppm (m, 2H, H-1).

2'-Azidoethylthioglycolic acid

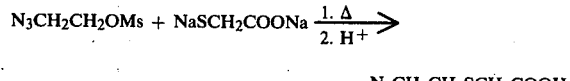

Thioglycolic acid (3.14 g, 34.1 mmol) was treated with 1 N NaOH solution (68 ml, 68.0 mmol) and the resulting solution was stirred at 23° C. for 0.5 h and treated with a solution of 2'-azidoethyl methanesulfonate (5.3 g, 32.1 mmol) in dimethoxyethane (15 ml). The reaction mixture was stirred at 45° C. for 22 h, cooled to 23° C., washed with CH$_2$Cl$_2$ (3×20 ml), acidified with 6 N HCl solution and extracted with CH$_2$Cl$_2$ (7×40 ml). The CH$_2$Cl$_2$ extracts were combined, dried over anhydrous Na$_2$SO$_4$ and concentrated on a rotary evaporator to an oil which was distilled under high vacuum bp 117°-22° C./0.27 torr, 4.2 g, 81.2%. ir (neat) ν$_{max}$: 2100 (s, N$_3$), 1708 (s, C=O) cm$^{-1}$. $^1$Hmr (CDCl$_3$) δ: 2.7-3.07 (m, 2H, H-1'), 3.35 (s, 2H, H-1), 3.30-3.73 (m, 2H, H-2') and 11.81 ppm (s, 1H, COOH).

2'-Azidoethylthioacetyl chloride

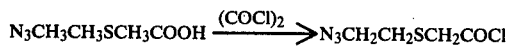

To a solution of 2-azidoethylthio glycolic acid (3.33 g, 20.7 mmol) in CH$_2$Cl$_2$ (50 ml) was added oxalyl chloride (3.9 ml) and DMF (one drop). The reaction mixture was stirred at 23° C. for 1.5 h and the solvent was removed on a rotary evaporator leaving a yellow liquid. ir(neat) ν$_{max}$: 2100 (s, N$_3$), 1785 (bs, C=O). $^1$Hmr (CDCl$_3$) δ: 2.6-3.0 (m, 2H, H-1'), 3.37-3.73 (m, 2H, H-2'), and 3.82 ppm (s, 2H, H-1).

4-(2'-azidoethylthioacetylthio)-1-(paranitrobenzyl 2'''-triphenylphosphoranylidene-2''-acetate)-2-azetidinone

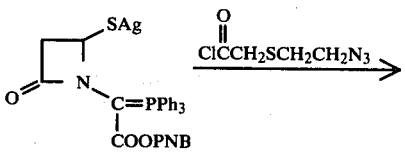

-continued

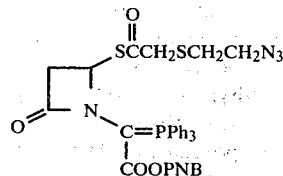

A solution of silver 1-(paranitrobenzyl 1'-triphenylphosphoranylidene-1'-acetate)-2-azetidinone-4-thiolate (15.7 mmol) and pyridine (1.6 ml, 19.8 mmol) in CH₂Cl₂ (200 ml) was treated dropwise (0.25 h) with a solution of 2'-azidoethylthioacetyl chloride (3.64 g, 20.3 mmol) in CH₂Cl₂ (50 ml). The reaction mixture was stirred at 23° C. for 1.5 h and filtered; the solids were washed with CH₂Cl₂. The filtrate and washings were combined and washed with 0.1 N HCl solution, H₂O, saturated NaHCO₃ solution and H₂O, dried over anhydrous Na₂SO₄ and concentrated on a rotary evaporator to an orange syrup. A column chromatography (300 g of silica gel G-60, eluent: EtOAc in CH₂Cl₂, 0–40%) of crude compound gave after evaporation of solvent a white powder, 7.7 g, 70%. An analytical sample was obtained after a recrystallization from CH₂Cl₂-ether-pet. ether, mp 150°–1° C. dec. Anal. calcd for $C_{34}H_{30}N_5O_6S_2P$: C 58.36, H 4.32, N 10.01, S 9.17; found: C 58.64, H 4.36, N 10.03, S 9.25. ir. (KBr) $\nu_{max}$: 2100 (s, N₃), 1750 (s, C=O of β-lactam), 1675 (s, C=O), 1655 (s, C=O), 1610 (s, aromatics), and 1440 cm⁻¹ (s, P-Ph).

paraNitrobenzyl 2-aminoethylthiomethylpenem-3-carboxylate

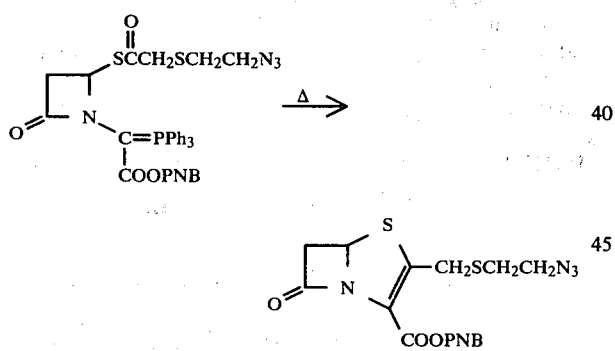

A suspension of 4-(2'-azidoethylthioacetylthio)-1-(paranitrobenzyl 2''-triphenylphosphoranylidenylacetate)-2-azetidinone (4.5 g, 6.43 mmol) in toluene (375 ml) was stirred at 110° C. for 2.25 h under a nitrogen atmosphere. The reaction mixture was cooled to 23° C. and the evaporation of solvent on a rotary evaporator gave an orange syrup. The purification of crude material was done on a silica gel column (90 g of silica gel G-60, eluent: ether-pet-ether, 1:1—3:2); the pure material was obtained as a yellow syrup, 2.2 g, 81%). ir (neat) $\nu_{max}$: 2100 (s, N₃), 1785 (s, C=O of β-lactam), 1705 cm⁻¹ (s, C=O of PNB); ¹Hmr (CDCl₃) δ: 2.53–2.90 (m, 2H, H-1''), 3.30–3.67 (m, 3H, HO2'', H-6 trans), 3.98 (ABq, $J_{a-b}$=14.8 Hz, 2H, H-1'), 5.32 (ABq, $J_{a-b}$=13.0 Hz, 2H, CH₂-PhNO₂), 5.66 (dd, $J_{H-5,H-6 cis}$=3.6 Hz, $J_{H-5,H-6 trans}$=1.9 Hz, 1-H, H-5), 7.58 (d, $J_{Ho-Hm}$=8.8 Hz, 2H, Ho PNB) and 8.19 ppm (d, $J_{Hm-Ho}$=8.8 Hz, 2H, Hm PNB).

2-Aminoethylthiomethylpenem-3-carboxylic acid

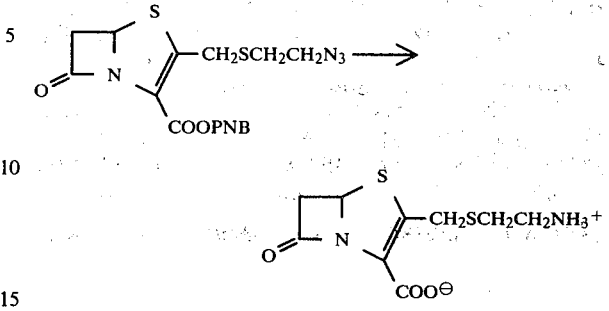

To a solution of p-nitrobenzyl 2-azidoethylthiomethylpenem-3-carboxylate (45 mg, 0.11 mmol) in dimethoxyethane (5 ml) were added ether (5 ml), water (5 ml) and 10% Pd/C (45 mg, 0.11 mmol). The reaction mixture was hydrogenated at 23° C. under 45 psi of hydrogen for 3.0 h and filtered over a Celite pad. The pad was washed with water and the filtrate and washings were combined and diluted with ether. The water phase was separated and washed with ether and lyophylized. The crude compound (20 mg) was purified by hplc: 5 mg, 18%; ir (KBr) $\nu_{max}$: 1765 (C=O), 1600 cm⁻¹ (b, COO⁻); ¹Hmr (D₂O) δ: 2.70–3.00 (m, 2H, H-1''), 3.15–3.45 (m, 2H, H-2''), 3.49 (dd, $J_{gem}$=16.8 Hz, $J_{6,5 trans}$=1.7 Hz, H-6 trans), 3.85 (dd, $J_{gem}$=16.8 Hz, $J_{6 cis}$=3.4 Hz, H-6 cis), 4.05 (ABq, $J_{a-b}$=14.6 Hz, 2H, H-1) and 5.74 ppm (dd, $J_{5-6 cis}$=3.4 Hz, $J_{5-6 trans}$=1.7 Hz, 1H, H-5); uv $\lambda_{max}$: 307 (ε4330), 250 (ε3282).

EXAMPLE 9

2-(2-Aminoethylsulfinylmethyl) penem-3-carboxylic Acid

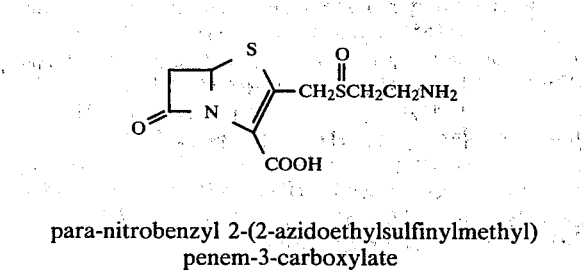

para-nitrobenzyl 2-(2-azidoethylsulfinylmethyl) penem-3-carboxylate

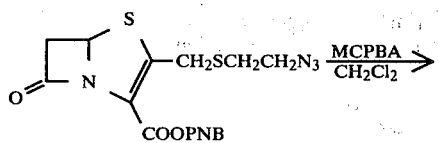

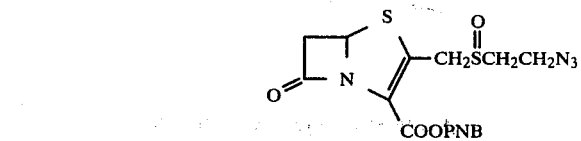

A solution of p-nitrobenzyl 2-azidoethylthiomethylpenem-3-carboxylate (0.36 g, 0.85 mmol) in CH₂Cl₂ (30 ml) was cooled to −20° C. under a nitrogen atmosphere and treated dropwise (2 h) with a solution m-chloroperbenzoic acid (0.147 g, 0.85 mmol) in CH₂Cl₂ (90 ml). The reaction mixture was stirred at −20° C. for 0.5 h, warmed up to room temperature and washed with a saturated NaHCO₃ solution and H₂O. The organic solution was dried over anhydrous Na₂SO₄ and concentrated under reduced pressure to an orange residue which was chromatographed over silica gel (silica gel G 60; 9 g; eluent; 25% EtOAc in CH₂Cl₂, fraction size: 7 ml). Concentration of the appropriate fractions gave a white solid; 0.27 g, mp 128°–31° C., 72.6%. Recrystallization from acetone-ether-pet-ether mixture gave an analytical sample; mp 142° C. dec; calcd for $C_{16}N_5O_6S_2$: C 43.93, H 3.46, N 16.01, S 14.66; found: C 43.79, H 3.44, N 16.02, S 14.63. ir (KBr) $\nu_{max}$: 2110 (N₃), 1785 (C=O of β-lactam), 1690 (C=O of PNB ester), 1600, 1560 (C=C), 1520, 1355 cm⁻¹ (NO₂); uv $\lambda_{max}^{CHCl_3}$: 265 (ε12884), 333 (ε8764); ¹Hmr (CDCl₃) δ: 2.95 (2H, m, CH₂CH₂N₃), 3.58 (dd, $J_{H-6-H-5\ trans}=2.0$ Hz, $J_{gem}=16.6$ Hz, H-6 trans), 4.33 (center of ABq, $J_{a,b}=13.4$ Hz, H-1'), 4.32 (center of ABq, $J_{a,b}=13.2$ Hz, H-1'), 5.33 (center of ABq, $J_{a,b}=13.7$ Hz, 2H, CH₂ of PNB ester), 5.75 (dd, $J_{H-5-H-6cis}=3.6$ Hz, $J_{H-5-H-6\ trans}=2.1$ Hz, 1H, H-5), 7.60 (d, $J_{Ho-Hm}=8.8$ Hz, 2H, Ho of PNB ester) and 8.22 (d, $J_{Hm-Ho}=8.8$ Hz, 2H, Hm of PNB ester).

2-(2-aminoethylsulfinylmethyl) penem-3-carboxylic acid

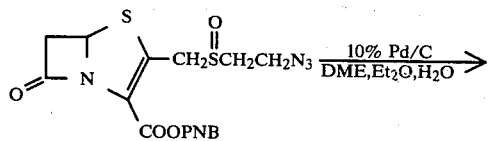

To a solution of paranitrobenzyl 2-(2-ethylsulfinylmethyl) penem-3-carboxylate (57 mg, 0.13 mmol) in dimethoxyethane (20 ml) was successively added Et₂O (10 ml), H₂O (10 ml) and 10% Pd on charcoal (57 mg). The reaction mixture was hydrogenated under 55 psi for 1.25 h and filtered over a Celite pad. The filtrate was diluted with Et₂O; the organic phase was separated and the aqueous solution was washed with Et₂O (twice) and lyophylized. The crude orange powder (30 mg) was purified by hplc; lyophylization of appropriate fractions gave the title compound as a white powder; 10.4 mg, 29%, uv $\lambda_{max}^{H_2O}$: 313 (ε4877); ir (KBr) $\nu_{max}$: 1720 (C=O of β-lactam) and 1590 (carboxylate); ¹Hmr (D₂O)δ: 3.0–3.7 (5H, H-6 trans, CH₂CH₂NH₃⁺), 3.90 (dd, $J_{H-6-H-5\ cis}=3.6$ Hz, $J_{gem}=16.9$ Hz, 1H, H-6 cis), 5.45 (center of ABq, $J_{a,b}=13.6$ Hz, H-1'), 4.50 (center of ABq, $J_{a,b}=13.6$ Hz, H-1') and 5.8 (m, 1H, H-5).

EXAMPLE 10

Silver 1-(β-Trimethylsilylethyl-2'-triphenylphosphoranylidene-2'-acetate)-2-azetidinone-4-thiolate

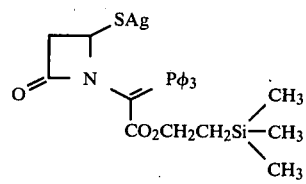

di-β-trimethylsilylethyl fumarate

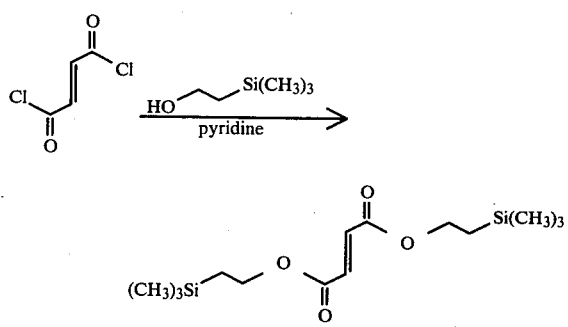

To a cold (−10° C.) ether (20 ml) solution of 2-trimethylsilyl ethanol (4.73 g, 0.04 mmol) [H. Gerlach Helv. Chim. Acta 60, 3039 (1977)] and pyridine (5.66 ml, 0.07 mol), under nitrogen, was added dropwise (15 min) fumaryl chloride (3.78 ml, 0.035 mol) dissolved in ether (10 ml). The black mixture was stirred five minutes at −10° C. and ten at room temperature. Charcoal was added and the reaction mixture filtered on a Celite pad. The filtrate was washed with sodium bicarbonate 1%-brine (1:1, 150 ml). The aqueous phase was back extracted with ether (30 ml). The ether solutions were combined, washed with brine, dried over sodium sulfate, filtered and concentrated under reduced pressure to give a brown solid. This compound was purified on a silica gel pad (30 g, 4×5 cm) with benzene (300 ml) as eluent to give an oil (4.855 g, 77%) which solidified on standing: mp 33°–34° C. Anal. calcd for $C_{14}H_{28}O_4Si_2$: C 53.12, H 8.91; found: C 53.35, H 8.91. ¹Hmr (CDCl₃)δ: 6.78 (2H, s, C=CH), 4.26 (4H, m, CH₂—O), 1.03 (4H, m, CH₂—Si) and 0.06 ppm (18H, s, (CH₃)₃Si); ir (CHCl₃) $\nu_{max}$: 1710 (C=O of ester), 1643 (C=C), 1267, 1258, 862 and 840 cm⁻¹ (Si —C).

Trimethylsilylethyl glyoxylate hydrate

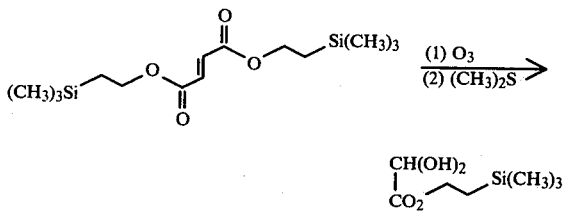

A solution of di-β-trimethylsilylethyl fumarate (37 g, 0.117 mmol) in methylene chloride (1.1 l) was ozonized at −78° C. until a blue color persisted. The excess ozone was purged with nitrogen and dimethyl sulfide (2.57 ml, 0.351 mol) was added. The solution was allowed to gradually warm to 23° C. The reaction mixture was diluted with carbon tetrachloride to 2 liters and washed with 1% aqueous solution of sodium carbonate (500 ml). The organic phase was dried over sodium sulfate, filtered on Celite and evaporated (~25° C.) to dryness to give 43.9 g of the title compound (97%); ir (neat) $v_{max}$: 3450 (—OH), 1740 (ester, 1255, 860 and 840 cm$^{-1}$ (Si—C).

1-(β-trimethylsilylethyl
2'-hydroxy-2'-acetate)-4-tritylthio-2-azetidinone

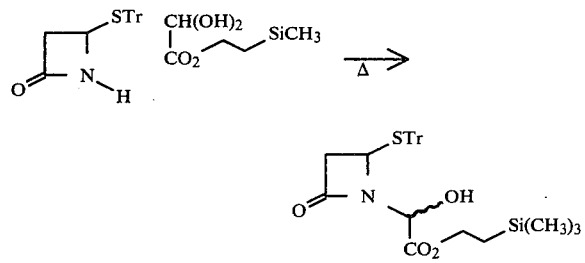

Trimethylsilylethyl glyoxylate hydrate (4.000 g, 11.6 mmol) and the 4-tritylthio-2-azetidinone (4.8 g, 24.96 mmol) were refluxed in benzene (25 ml) through a Dean Stark condenser, under nitrogen for 24 h. The solvent was evaporated under a vacuum. The produce was chromatographed on a silica gel column (450 g, 8.5×14.5 cm) and eluted with ethyl acetate: methylene chloride (1:19) until the title compound started to come out (~1.5 l) and then with ethylacetate:methylene chloride (1:9, 2 l). The fractions containing the title compound were combined and evaporated to dryness to give 5.415 g (89%) of the title compound. $^1$Hmr (CDCl$_3$)δ: 7.80 to 6.70 (15H, m, trityl), 5.23 and 4.90 (1H, 2s, H—C—O), 4.50 to 4.10 (3H, m, H-3 and O—CH$_2$), 2.60 (2H, m, H-2), 0.95 (2H, m, CH$_2$—Si and 0.1 ppm (9H, s, Si—CH$_3$); ir (CHCl$_3$) $v_{max}$: 3520 (—OH), 1765 (C=O of β-lactam), 1740 (C=O of ester), 1595 (C—H, aromatic), 1257, 860 and 840 cm$^{-1}$ (C—Si)

1-(β-trimethylsilylethyl
2'-chloro-2'-acetate)-4-tritylthio-2-azetidinone

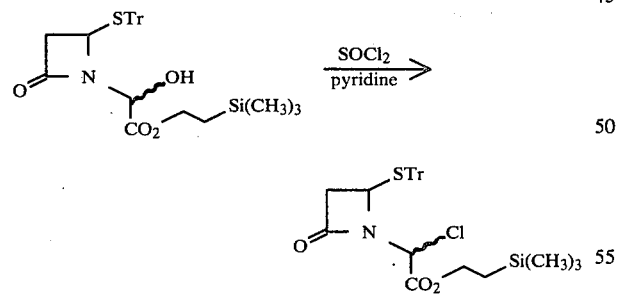

A solution of thionyl chloride (0.74 ml, 10.37 mmol) in dry THF (9 ml) was added dropwise with stirring to a solution of 1-(β-trimethylsilylethyl 2'-hydroxy-2'-acetate)-4-tritylthio-2-azetidinone (4.9 g, 9.37 mmol), pyridine (0.84 ml, 10.38 mmol) and dry THF (40 ml) at −15° C. under a nitrogen atmosphere. The mixture was stirred at −15° C. for 2 h. The precipitate was removed by filtration on a Celite pad and washed with benzene (50 ml). The filtrate was evaporated in vacuo at 30° C. The residue was dissolved in benzene (100 ml), treated with charcoal and filtered through a Celite pad. Evaporation of the solvent gave a residue which was purified through a silica gel pad (100 g, 4.7×11 cm): hexane-benzene (1:1, 400 ml), ether-benzene (1:19, 1 l). Evaporation of the pertinent fractions gave 4.64 g of the title compound (92%). $^1$Hmr (CDCl$_3$)δ: 7.30 (15H, m, aromatic H), 5.77 and 5.43 (1H, 2s, CH—Cl), 4.7 to 4.2 (3H, m, H-4 and CH$_2$—O), 2.85 to 2.50 (2H, m, H-3), 1.15 (2H, m, CH$_2$—Si) and 0.06 ppm (9H, s, Si—CH$_3$); ir (neat) $v_{max}$: 1760 (C=O), 860 and 840 cm$^{-1}$ (C—Si).

1-(β-trimethylsilylethyl-2'-triphenylphosphoranylidene-2'-acetate)-4-tritylthio-2-azetidinone

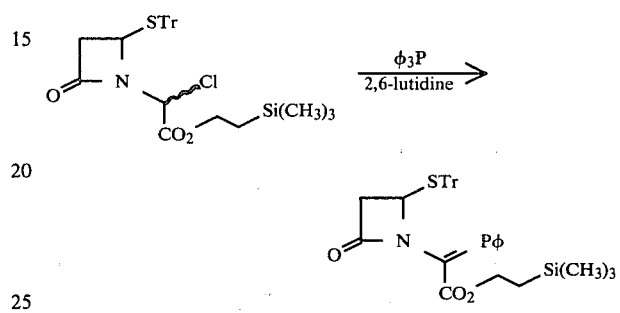

A dioxane (20 ml) solution of the above chloroazetidinone (4.12 g, 7.568) was treated with triphenylphosphine (2.209 g, 8,424 mmol) and 2,6-lutidine (0.98 ml, 8.424 mmol). The mixture was refluxed for 3.5 h. The cooled solution was filtered and the white solid washed with THF. The filtrate was evaporated to dryness. The residue was purified on a silica gel column (200 g, 4×31 cm) using ethylacetate-hexane (3:7, 1 l; 7:3, 1 l) to give the title phosphorane (4.836 g, 83%). ir (film) $v_{max}$: 1755 (C=O), 1615 (phosphorane), 850 and 830 cm$^{-1}$ (Si—C). Anal. calcd for C$_{47}$H$_{46}$NO$_3$PSSi: C 73.89, H 6.07, N 1.81; found: C 72.18, H 6.08, N 1.83

Silver
1-(β-trimethylsilylethyl-2'-triphenylphosphoranylidene-2'-acetate)-2-azetidinone-4-thiolate

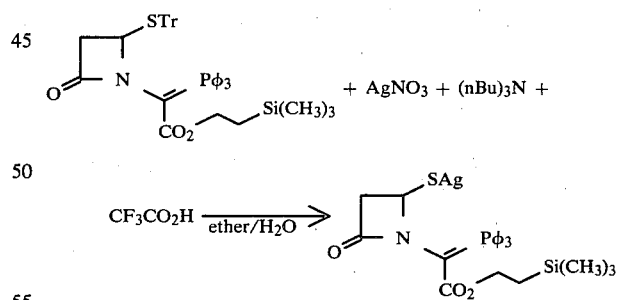

1-(β-trimethylsilylethyl-2'-triphenyl phosphoranylidene-2'-azetate)-2-azetidinone (7.64 g, 10 mmol) was dissolved in ether (60 ml). An aqueous solution of silver nitrate (0.5 M, 80 ml, 40 mmol) was added followed by a rapid addition (1 min) of a solution of tributylamine (3 ml, 12.58 mmol) and trifluoroacetic acid (0.154 ml, 0.2 mmol) in ether (20 ml). The mixture was mechanically stirred for 19 min. The precipitate was filtered, rinsed with ether (200 ml), triturated in water (70 ml), filtered again and rinsed with ether (100 ml). The light brown solid was dried under vacuum (water aspirator 10 min and pump 65 min) to give the title compound (6.42 g). ir (CHCl$_3$) $\nu_{max}$: 1862 (C=O), 1630 (phosphorane), 860 and 840 cm$^{-1}$ (Si—C).

EXAMPLE 11

Silver 3-(1'-Hydroxy-1'-ethyl)-1-($\beta$-trimethylsilylethyl 2''-triphenylphosphoranylidene-2''-acetate)-2-azetidinone-4-thiolate

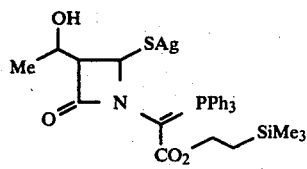

trans 3-acetyl-1-($\beta$-trimethylsilylethyl 2'-triphenylphosphoranylidene-2'-acetate)-4-tritylthio-2-azetidinone

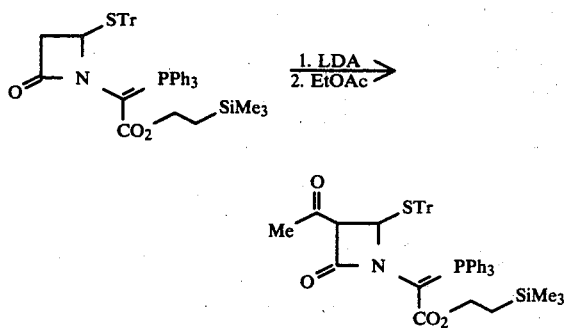

To a solution of diisopropylamine (0.80 ml, 5.5 mmol) in tetrahydrofuran (25 ml) at −78° C. was added n-butyl lithium (4.0 ml, 6.0 mmol) with stirring. After 3 min, a solution of 1-($\beta$-trimethylsilylethyl 2'-triphenylphosphoranylidene-2'-acetate)-4-tritylthio-2-azetidinone (3.82 g, 5.00 mmol) in tetrahydrofuran (40 ml) was added dropwise over 20 min with stirring. After 2 min, 2.5 ml (25 mmol) of ethyl acetate was added and the solution was stirred for 10 min. The cooling bath was removed and 0.2 M hydrochloric (58 ml) acid was added with vigorous stirring. Water and ethyl acetate were added (65 ml each), shaken and separated. The organic phase was washed with water and saturated sodium chloride (60 ml each), dried and the solvent was evaporated in vacuo to give the crude product, 4.1 g. The product was absorbed from methylene chloride onto 20 g of silica gel and placed (dry) on a 120 g silica gel column. The column was eluted with ether/hexane 1:1 (200 ml) then with ether (500 ml). Evaporation of the solvent from the appropriate fractions gave partially purified title compound, 2.17 g (53%); ir $\nu_{max}$: 1755 ($\beta$-lactam and ester) and 1710 cm$^{-1}$ (ketone); $^1$Hmr (CDCl$_3$)$\delta$: 1.67 and 1.87 peaks for

CH$_3$C—, trimethylsilyl and aromatic peaks; remainder poorly resolved.

3-(1'-hydroxy-1'-ethyl)-1-($\beta$-trimethylsilylethyl 2''-triphenylphosphoranylidene-2''-acetate)-4-tritylthio-2-azetidinone.

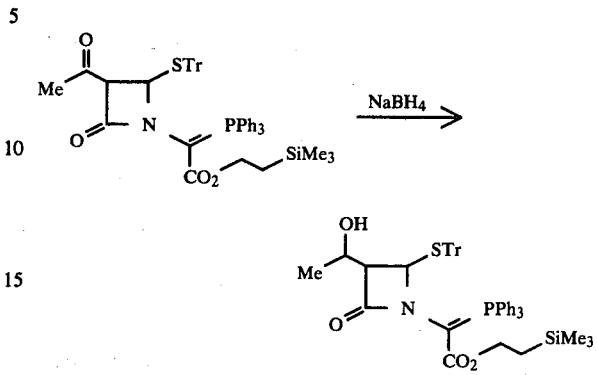

A solution of the above compound (2.10 g, 2.60 mmol) in tetrahydrofuran (20 ml) was added to a slurry of sodium borohydride (160 mg, 4.3 mmol) in tetrahydrofuran (10 ml). The mixture was stirred at 23° C. for 4 h. Water (30 ml) was added followed by the slow addition of 1 M hydrochloric acid until pH 3 was reached. The mixture was extracted with ethyl acetate (50 ml). The organic phase was washed with 50 ml each of 0.1 M sodium bicarbonate, diluted sodium chloride and saturated sodium chloride then dried and the solvent was evaporated in vacuo to give the crude product, 2.22 g. The product was absorbed from methylene chloride onto 11 g of silica gel and placed (dry) on a 44 g silica gel column. The column was eluted with ether. Evaporation of the solvent from the appropriate fractions gave partially purified title compound, 1.43 g (68%); $^1$Hmr (CDCl$_3$): peaks around $\delta$1 for

OH
|
CH$_3$CH—, trimethylsilyl and aromatic peaks; remainder poorly resolved.

Silver 3-(1'-hydroxy-1'-ethyl)-1-($\beta$-trimethylsilylethyl 2''-triphenylphosphoranylidene-2''-acetate)-2-azetidinone-4-thiolate

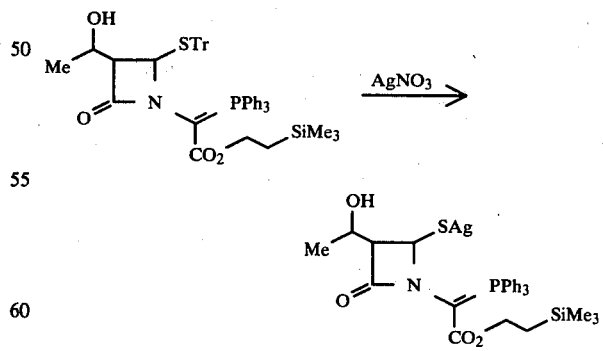

A solution of silver nitrate (1.42 g, 8.4 mmol) in water (40 ml) and a solution of pyridine (0.27 ml, 3.35 mmol) and the above phosphorane (1.35 g, 1.67 mmol) in ether (40 ml) were stirred together vigorously at 23° C. for 1 h. The precipitate was collected by filtration, washed with water and ether and dried to give crude title compound 1.24 g (100%); ir $v_{max}$: 3420 (OH) and 7150 cm$^{-1}$ ($\beta$-lactam and ester).

EXAMPLE 12

(1'R,5R,6S and 1'S,5S,6R)
6-(1'-Hydroxyethyl)-2-(2-aminoethoxymethyl)penem-3-carboxylic Acid (isomer B)—Alternate Procedure

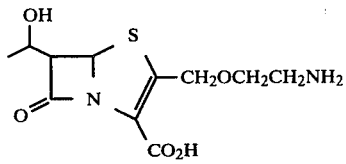
(Isomer B)

(1'R,3S,4R and 1'S,3R,4S)
4-(2-azidoethoxyacetylthio)-3-(1'-hydroxyethyl)-1-($\beta$-trimethylsilylethyl 2''-triphenylphosphoranylidene-2''-acetate)-2-azetidinone

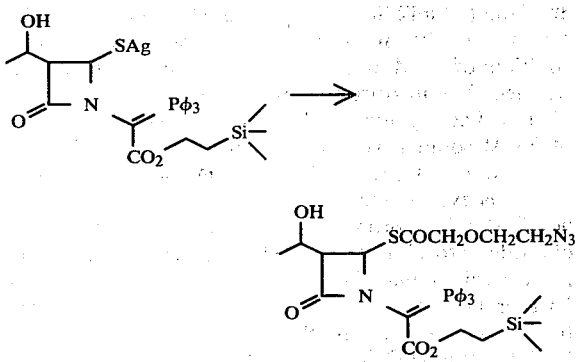

Trimethylsilyl chloride (1.54 ml, 11.8 mmol) was added to a stirred slurry of silver 3-(1'-hydroxyethyl)-1-($\beta$-trimethylsilylethyl 2''-triphenylphosphoranylidene-2''-acetate)-2-azetidinone-4-thiolate (isomer B) (2.48 g, 3.34 mmol), imidazole (136 mg, 2.0 mmol) and triethylamine (1.64 ml, 11.8 mmol) in THF (60 ml) at 0° C. The mixture was stirred at 23° for 18 h. Methylene chloride (60 ml) was added, the mixture cooled to −15° C., pyridine (1.32 ml, 16.4 mmol) and $\beta$-azidoethoxyacetyl chloride (1.43 g, 8.70 mmol) added and the mixture stirred at −15° C. for 0.5 h. Ether (60 ml), ethyl acetate (60 ml) and 1 M hydrochloric acid (20 ml) were added. The precipitate was removed by filtration and the organic phase was washed with 0.1 M hydrochloric acid (100 ml), 1% sodium bicarbonate (100 ml), and saturated sodium chloride. Concentration of the dried solution gave crude title compound as an oil. 85%. ir $v_{max}$: 1755 and 1695 cm$^{-1}$.

(1'R,5R,6S and 1'S,5S,6R) $\beta$-trimethylsilylethyl 2-$\beta$-azidoethoxymethyl-6-(1'-hydroxyethyl)-penem-3-carboxylate (Isomer B)

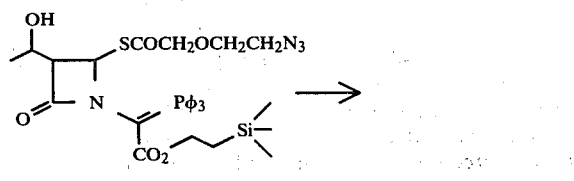

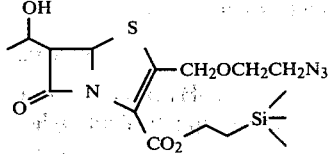

A solution of the above phosphorane (1.3 g) in toluene (200 ml) was heated under reflux for 3 h. Concentration of the solvent on a rotary evaporator gave the crude title compound. Chromatography on silica gel (40 g) eluting with increasing proportions of ether in hexane gave crystalline title compound, 65%. ir $v_{max}$: 1760 and 1700 cm$^{-1}$; $^1$Hmr indicated contamination with a second isomer.

(1'R,5R,6S and 1'S,5S,6R)-2-$\beta$-azidoethoxymethyl-6-(1'-hydroxyethyl)-penem-3-carboxylic acid (Isomer B).

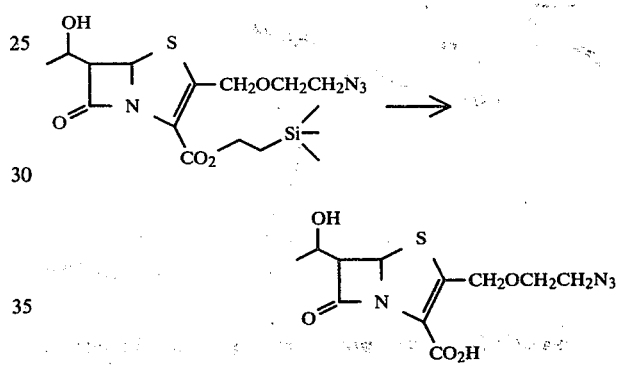

A solution of anhydrous tetrabutylammonium fluoride (3 ml, 1.5 mmol) in THF was added to a solution of the above ester (155 mg, 0.37 mmol) in THF (2 ml) at 0° C. After 5 min at 0° C., water (10 ml) and ethyl acetate (10 ml) were added, the mixture was acidified to pH 3 (1 M hydrochloric acid) and the phases separated. The organic phase was extracted with 0.05 M sodium bicarbonate, the aqueous extracts acidified to pH 3 with hydrochloric acid and extracted with ethyl acetate. The organic extracts were washed with saturated sodium chloride, dried, concentrated on the rotary evaporator and the residue triturated in ether to give the crude title compound as a solid, 27 mg, 28%. ir $v_{max}$: 3500, 1785, 1670 cm$^{-1}$; $^1$Hmr (CDCl$_3$)δ: 1.30 (3H, d, J=6.5, CH$_3$-1'), 2.22 (1H, OH), 3.1–3.9 (5H, m, CH$_2$ and H-6), 3.9–4.4 (1H, m, H-1'), 5.60 (1H, d, J=1, H-5).

(1'R,5R,6S and 1'S,5S,6R)
6-(1'-Hydroxyethyl)-2-(2-aminoethoxymethyl)-penem-3-carboxylic acid (Isomer B)

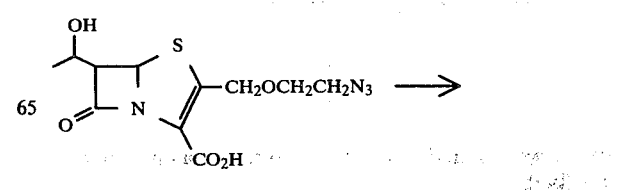

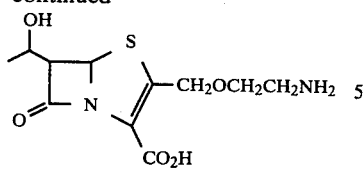

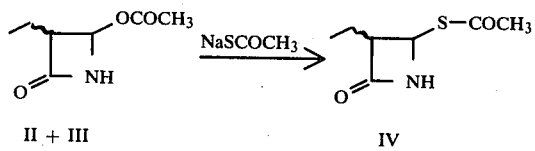

A solution of the above azidocompound (150 mg) in THF (15 ml), ether (15 ml) and water (15 ml) was hydrogenated in a Parr shaker in the presence of 10% Pd/C (150 mg) at an initial $H_2$ pressure of 60 psi. After 3 h the catalyst was removed by filtration over Celite and the aqueous phase was washed with ethyl acetate and lyophilized to give the crude title compound. Purification by hplc (Waters, $C_{18}$ Micro Bondapack Reverse Phase) gave 46.7 mg of pure title compound identical to a previously prepared sample prepared by hydrogenation/hydrogenolysis of the corresponding azido p-nitrobenzyl derivative.

EXAMPLE 13

6-Ethyl-2-(2-aminoethoxymethyl)penem-3-carboxylic Acid

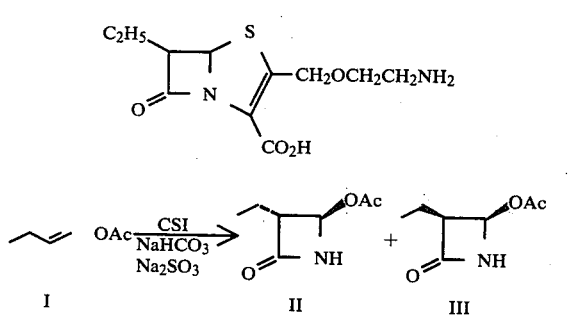

The 1-butenylacetate (about 1:1 mixture of cis and trans isomers) was prepared according to P. Z. Bedoukian, *J. Am. Chem. Soc.* 66 1325(1944).

To cooled ($-15°$ C.) I (50 ml) was added dropwise 10 ml (11 g, 78 mmoles) of CSI. The mixture was allowed to warm up gradually during 30 min. to 0° C. It was cooled to $-20°$ C. and poured carefully onto a mixture of water (8 ml) ice (35 g), $NaHCO_3$ (18.4 g) and $Na_2SO_3$ (6.4 g). This was stirred vigorously at 0° C. for 30 min., treated with pet. ether (250 ml) and cooled to $-40°$ C. The solvent was decanted and the residue was treated with another 100 ml of pet. ether in the same way. The combined pet. ether extracts were washed with water (30 ml) and dried ($Na_2SO_4$) for recycling of I.

The aqueous phases were combined and extracted with ethylacetate (5×40 ml). The extract was dried ($Na_2SO_4$) and concentrated in vacuo to give 7.0 g (57%) of a mixture of 28% II and 72% III, b.p. 82°–85° C. (0.01 mm); n.m.r. δ(ppm, $CDCl_3$) 7.3 (1H,NH) 5.92 (0.72 H, d, J=4.4, II-H-3), 3.3 (0.28 H, d, J=1.4, III-H-4), 3.3 (1H, m, H-3), 2.24 (3H, s), 2.72 (2H, two q, J=7), 1.1 (3H, two t, J=7). $v_{c=o}$ 1775, 1755 cm$^{-1}$ Anal. calcd. for $C_7H_{11}NO_3$ C 53.49, H 7.05, N 8.91. Found C 53.12, H 6.93, H 8.85.

Sodium thioacetate was prepared by addition of thioacetic acid (0.8 ml, 850 mg, 11.2 mmoles) to a cooled (ice-bath) 1N sodium hydroxide solution (11.2 ml) under nitrogen. This was added to a cooled solution of II and III (1.57 g 10 mmoles) in water (5 ml) under $N_2$. The mixture was stirred for 1 h at room temperature. Since an oil was separating, acetone (9 ml) was added and stirring continued for 1.5 h. The mixture was concentrated in vacuo to remove acetone and then extracted with methylene chloride. The extract was dried and concentrated in vacuo to give 1.65 g (95%) of crude mixture of 85% trans IV and 15% cis IV bp 105°–110° (0.02 mm), 7.1 (1H,NH) 5.53 (0.24H, d, J=4.5, cis-H-4), 5.12 (0.8H, d, J=2.4 trans-H-4) 3.34 (1H, two t, J=7) 2.48 (3H) 1.9 (1H, two q, J=7) 1.15 (3H, two T, J=7. $v_{c=o}$ 1700, 1765 cm$^{-1}$. Anal. calcd for $C_7H_{11}N$ C 48.53, H 6.40, N 8.07. Found C 48.18, H 6.47, N 7.77

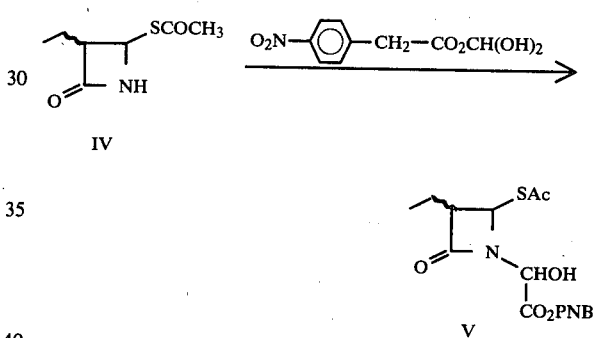

A mixture of IV (1.25 g, 7.2 mmole) and p-nitrobenzyl glyoxylate (1.6 g, 7.5 mmole) in benzene (80 ml) was refluxed 20 h under a Dean Stark water collector followed by concentration in vacuo to give 3.01 g of crude product. This was filtered over a small amount of silica in chloroform to give 2.8 g (quantitative yield) of slightly yellow oil V containing some solvent, δ7.9 (4H, m) 5.3 (4H,m) 4.8 (1H, OH) 3.2 (1H, m) 3.37 and 3.33 (3H, two s) 1.8 (2H, m) 1.05 (3H, m) $v_{c=o}$ 1765,1700 cm$^{-1}$. This product was used in the next step without further purification.

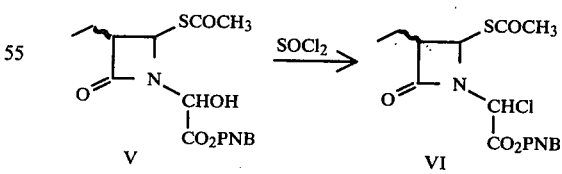

To a cooled (ice-bath) stirred solution of V (2.1 g, 5.5 mmole) in dry benzene (10 ml) was added thionyl chloride (3 ml) and the mixture kept at 5° C. for 2 h followed by evaporation in vacuo at room temperature. The excess thionyl chloride was removed by repeated addition and evaporation of benzene and the product was purified by filtration of the benzene solution over a small amount of silica gel, to give after concentration in vacuo 1.7 g (77%) of crude slightly yellow oil VI, δ7.9 (4H, m) 6.0 (1H, s) 5.3 (3H, m) 3.3 (1H, m) 2.7 and 2.3 (3H, two s) 1.75 (3H, m) 1.0 (3H, m) $\nu_{c=o}$ 1700, 1775 cm$^{-1}$. The product was used in the next step without further purification.

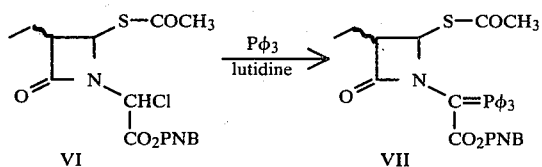

A mixture of VI (1.7 g, 4.2 mmoles), triphenylphosphine (1.57 g 6.0 mmoles) and 2,6-lutidine (5.35 mg, 5 mmoles) in dry dioxane (20 ml) was heated at 55° for 19 h, followed by concentration in vacuo. The dark-red residue was chromatographed on a silica gel column (35 g). Elution with benzene-ether gave 2.3 g (87%) of crude VII as light red oil, which was used in the next step without further purification.

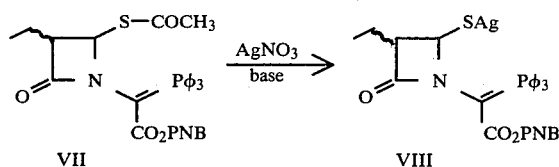

Mercaptide VIII is prepared from VII by the general procedure of Example 3.

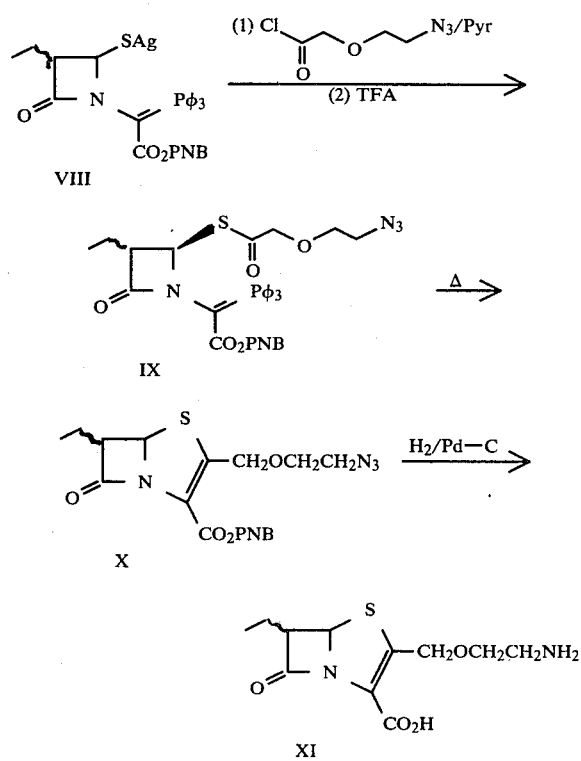

Reaction of mercaptide VIII with 2-azidoethoxyacetyl chloride according to the procedure of Example 6 gives intermediate IX which may be cyclized and reduced as in Example 6 to give the title product.

BIOLOGICAL DATA

Representative compounds of the present invention were subjected to in vitro antibiotic screening against a variety of microorganisms. Samples of the indicated compounds after solution in water and dilution with Nutrient Broth were found to exhibit the following Minimum Inhibitory Concentration (MIC) in mcg./ml. versus the indicated microorganisms as determined by overnight incubation at 37° C. by the tube dilution method.

| | M.I.C. in mcg/ml | | | |
| --- | --- | --- | --- | --- |
| | Compound (Example No.) | | | |
| Organism | 6 | 7 | 8 | 9 |
| Streptococcus pneumoniae A9585 | .03 | .13 | .13 | .5 |
| Streptococcus pyogenes A9604 | .03 | .13 | .13 | .5 |
| Stapylococcus aureus A9537 | .06 | .13 | .13 | .5 |
| Staph aureus +50% Serum A9537 | .5 | 1 | .5 | 4 |
| Staphylococcus aureus A9606 | .25 | 32 | 16 | 4 |
| Staphylococcus aureus A15097 | .1 | 125 | 16 | 63 |
| Streptococcus faecalis A20688 | 4 | 32 | 63 | >63 |
| Escherichia coli A15119 | .5 | 2 | 4 | 8 |
| Escherichia coli A20341-1 | .5 | 8 | 16 | 32 |
| Klebsiella pneumoniae A15130 | 2 | 4 | 8 | 32 |
| Klebsiella species A20468 | 2 | >125 | >63 | >63 |
| Proteus mirabilis A9900 | 1 | 2 | 4 | 8 |
| Proteus vulgaris A21559 | 1 | 8 | 16 | 16 |
| Proteus morganii A15153 | 4 | 8 | 8 | 16 |
| Proteus rettgeri A21203 | 2 | 2 | 8 | 16 |
| Serratia marcescens A20019 | 2 | 2 | 8 | 32 |
| Enterobacter cloacae A9659 | 8 | 8 | 32 | 32 |
| Enterobacter cloacae A9656 | 2 | 4 | 32 | 63 |
| Pseudomonas aeruginosa A9843A | 16 | 63 | 63 | 63 |
| Pseudomonas aeruginosa A21213 | 8 | 125 | >63 | 63 |
| Hemophilus influenzae A9833 | — | — | — | — |
| Haemophilus influenzae A21522 | — | — | — | — |
| Bacteroides fragilis A20931 | — | — | — | — |
| Bacteroides fragilis A20929 | — | — | — | — |

The compounds of Examples 6 and 7 were also tested in vivo in mice and their PD$_{50}$ (dose of compound in mg/kg required to protect 50% of the treated mice against an otherwise lethal infection of a microorganism) values determined with respect to S. aureus A9537.

| Compound | # of infecting organisms of S. aureus A9537 | # of treatments | Treatment route | PD$_{50}$ (mg/kg/ treatment) |
|---|---|---|---|---|
| Compound of Ex. 6 | 1.1 × 10$^6$ | 2 | IM | 0.12 |
| Compound of Ex. 7 | 1 × 10$^6$ | 2 | IM | 1.9 |

We claim:

1. An intermediate having the formula

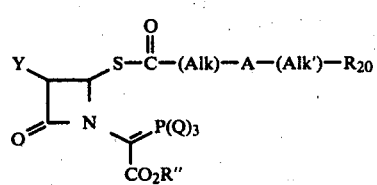

wherein Q is phenyl or (lower)alkyl; R" is a conventional carboxyl protecting group; Alk is a $C_1$-$C_2$ alkylene group optionally substituted by a $C_1$-$C_4$ alkyl radical; A is O, S, SO, SO$_2$ or NR$_{21}$ in which R$_{21}$ is hydrogen, (lower)alkyl, phenyl or phenyl(lower)alkyl; Alk' is a $C_2$-$C_4$ alkylene group; R$_{20}$ is —NHOH, —NR$_{22}$R$_{23}$ in which R$_{22}$ and R$_{23}$ are each independently hydrogen or (lower)alkyl, —N$_3$ or NO$_2$; and Y is hydrogen; or a pharmaceutically acceptable salt thereof.

2. An intermediate having the formula

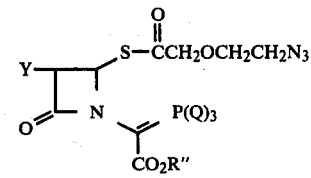

wherein Q is phenyl or (lower)alkyl, R" is a conventional carboxyl protecting group and Y is hydrogen.

3. An intermediate having the formula

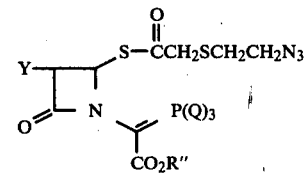

wherein Q is phenyl or (lower)alkyl; R" is a conventional carboxyl protecting group and Y is hydrogen.

* * * * *